US008741862B2

(12) United States Patent
Carmeliet et al.

(10) Patent No.: US 8,741,862 B2
(45) Date of Patent: Jun. 3, 2014

(54) PHD2 INHIBITION FOR BLOOD VESSEL NORMALIZATION, AND USES THEREOF

(75) Inventors: Peter Carmeliet, Blanden (BE); Massimiliano Mazzone, Kessel-Lo (BE)

(73) Assignees: VIB VZW, Ghent (BE); Life Science Research Partners VZW, Leuven (BE)

(*) Notice: Subject to any disclaimer, the term of this patent is extended or adjusted under 35 U.S.C. 154(b) by 0 days.

(21) Appl. No.: 13/138,224

(22) PCT Filed: Jan. 20, 2010

(86) PCT No.: PCT/EP2010/050645
§ 371 (c)(1),
(2), (4) Date: Oct. 7, 2011

(87) PCT Pub. No.: WO2010/084134
PCT Pub. Date: Jul. 29, 2010

(65) Prior Publication Data
US 2012/0022135 A1  Jan. 26, 2012

Related U.S. Application Data

(60) Provisional application No. 61/145,789, filed on Jan. 20, 2009.

(30) Foreign Application Priority Data

Feb. 13, 2009 (EP) .................................. 09152807

(51) Int. Cl.
A61K 48/00 (2006.01)
A61K 31/7088 (2006.01)
C12N 15/113 (2010.01)

(52) U.S. Cl.
USPC .......... 514/44; 435/6.1; 435/91.1; 435/91.31; 435/455; 536/23.1; 536/24.5

(58) Field of Classification Search
USPC ......... 435/6, 6.1, 91.1, 91.31, 455; 514/44, 1, 514/2; 536/23.1, 24.3, 24.5
See application file for complete search history.

(56) References Cited

U.S. PATENT DOCUMENTS

2003/0166584 A1    9/2003  Hu
2009/0004668 A1*   1/2009  Chen et al. .................. 435/6
2010/0004325 A1    1/2010  Yang

FOREIGN PATENT DOCUMENTS

KR   2008 0069384 A      7/2008
WO   WO 02/44321    *    6/2002
WO   WO 2010/084134 A1   7/2010

OTHER PUBLICATIONS

Takeda et al, Circulation, Vo. 116, pp. 774-781 (2007).*
Nangaku et al, Arteriosclerosis Thrombosis and Vascular Biology, Vo. 27, pp. 2548-2554 (2007).*
Takeda et al, Hypertension, vol. 49, pp. 178-184 (2007).*
Doench et al., Genes & development, vol. 18, No. 5, pages 504-511 (2004).*
Holen et al, Vucleic Acids Res., vol. 30, No. 8, pages 1757-1766 (2002).*
Opalinska et al., Nature Rev., vol. 1, pp. 503-514 (2002).*
Peracchi et al., Rev. Med. Virol., vol. 14, pp. 47-64 (2004).*
Lee et al., Mol. Cancer Res., vol. 6, No. 5, pp. 829-842 (2008).*
Dettori et al., Heterozygous deficiency of the oxygen sensor PHD2 prevents metastasis by inducing vessel normalization, European Journal of Cancer, Jul. 1, 2008, p. 16, vol. 6, No. 9, Pergamon, Oxford, GB.
Cho et al., Baicalein induces functional hypoxia-inducible factor-1 alpha and angiogenesis, Molecular Pharmacology, Jul. 2008, pp. 70-81, vol. 74, No. 1.
Lee et al., The biphasic role of the hypoxia-inducible factor prolyl-4-hydroxylase, PHD2, in modulating tumor-forming potential, Molecular Cancer Research, May 2008, pp. 829-42, vol. 6, No. 5.
PCT International Search Report, PCT/EP2010/050645, dated Apr. 9, 2010.
Bumcrot et al., RNAi Therapeutics: A Potential New Class of Pharmaceutical Drugs, Nature Chemical Biology, Dec. 2006, pp. 711-19, vol. 2, No. 12.
Bergers et al., Modes of Resistance to Anti-Angiogenic Therapy, Nature Reviews, Cancer, Aug. 2008, pp. 592-603, vol. 8, Macmillan Publishers Limited.
Carmeliet, Peter, Angiogenesis in health and disease, Nature Medicine, Jun. 2003, pp. 653-660, vol. 9, No. 6.
Chan et al., Tumor Vasculature is Regulated by PHD2-mediated Angiogenesis and Bone Marrow-Derived Cell Recruitment, Cancer Cell, Jun. 2, 2009, pp. 527-538, vol. 15, No. 6, Elsevier Inc.
Gerhardt et al., VEGF Guides Angiogenic Sprouting Utilizing Endothelial Tip Cell Filopodia, Journal of Cell Biology, Jun. 2003, pp. 1163-1177, The Rockefeller University Press, vol. 161, No. 6.
Hamzah et al., Vascular Normalization in RgsS-deficient Tumours Promotes Immune Destruction, Nature, May 15, 2008, pp. 410-415, vol. 453.
Jain, Rakesh K., Normalization of Tumor Vasculature: An Emerging Concept in Antiangiogenic Therapy, Science, Jan. 7, 2005, pp. 58-62, vol. 307.
Kashiwagi et al., Perivascular nitric oxide gradients normalize tumor vasculature, Nature Medicine, Mar. 2008, pp. 255-257, vol. 14, No. 3.

(Continued)

Primary Examiner — Jane Zara
(74) Attorney, Agent, or Firm — TraskBritt, P.C.

(57) ABSTRACT

A key function of blood vessels, to supply oxygen, is impaired in tumors because of abnormalities in their endothelial lining. PHD proteins serve as oxygen sensors and may regulate oxygen delivery. Therefore the role of endothelial PHD2 in vessel shaping by implanting tumors in PHD2$^{+/-}$ mice was studied. Haplodeficiency of PHD2 did not affect tumor vessel density or lumen size, but normalized the endothelial lining and vessel maturation. This resulted in improved tumor perfusion and oxygenation, and inhibited tumor cell invasion, intravasation and metastasis. Haplodeficiency of PHD2 redirected the specification of endothelial tip cells to a more quiescent phenotype of a filopodia-lacking "phalanx" cell type. Without being bound to a particular mechanism, this transition could at least in part be explained by upregulation of (soluble) VEGFR-1 and VE-cadherin. Thus, decreased activity of an oxygen sensor in hypoxic conditions prompts endothelial cells to readjust their shape and phenotype to restore oxygen supply. Inhibiting PHD2 may offer alternative therapeutic opportunities for anti-cancer therapy, or other therapies where vascular normalization is beneficial.

19 Claims, 31 Drawing Sheets

(56) References Cited

OTHER PUBLICATIONS

Stockmann et al., Deletion of Vascular Endothelial Growth Factor in Myeloid Cells Accelerates Tumorigenesis, Nature, Dec. 11, 2008, pp. 814-819, vol. 456.

Takeda et al., Prolyl Hydroxylase Domain 2 Protein Suppresses Hypoxia-Induced Endothelial Cell Proliferation, Hypertension, 2007, pp. 178-184, vol. 49.

* cited by examiner

A

P=0.0034

B

P=0.0032

C

P=0.0377

D

E

F

B

A

B

C

G    WT                           PHD2[+/-]

perfused vessel number
    Thigh  10484.5 ± 3403.2         11430.5 ± 914.6
    Calf    5905.0 ± 1594.5         11491 ± 993.5

H     I

PHD2 INHIBITION FOR BLOOD VESSEL NORMALIZATION, AND USES THEREOF

CROSS-REFERENCE TO RELATED APPLICATIONS

This application is a national phase entry of PCT International Patent Application No. PCT/EP2010/05645, filed on Jan. 20, 2010, designating the United States of America, and published, in English, as PCT International Publication No. WO 2010/084134 A1 on Jul. 29, 2010, which application claims the benefit under 35 U.S.C. §119(e) of U.S. Provisional Application No. 61/145,789 filed Jan. 20, 2009, and under Article 8 of the PCT to European Application No. 09152807.5 filed Feb. 13, 2009.

STATEMENT ACCORDING TO 37 C.F.R. §1.52(e)(5)

Sequence Listing Submitted on Compact Disc

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "V306_ST25.txt" which is 9 KB and created on Jul. 19, 2011.

TECHNICAL FIELD

The invention relates to the field of blood vessels and perfusion of tissues. It explores how perfusion may be modified not by angiogenesis (generation of new blood vessels) or anti-angiogenesis (inhibition of new blood vessel generation) but by normalization of existing vessels.

BACKGROUND

Numerous studies have examined how blood vessels arise, branch and elongate, but little is known concerning how morphogenesis of the endothelial layer is regulated. This is, nonetheless, critical, since a leaky misshaped endothelium in for instance tumor vessels impairs perfusion and oxygenation (Jain, 2005). Indeed, to obtain nutrients for their growth and to metastasize to distant organs, cancer cells co-opt host vessels, sprout new vessels from existing ones (angiogenesis), and/or recruit endothelial cells from the bone marrow (postnatal vasculogenesis). The resulting vasculature is structurally and functionally abnormal. Blood vessels are leaky, tortuous, dilated, and saccular and have a haphazard pattern of interconnection. The endothelial cells lining these vessels have aberrant morphology, pericytes (cells that provide support for the endothelial cells) are loosely attached or absent, and the basement membrane is often abnormal—unusually thick at times, entirely absent at others.

These structural abnormalities contribute to spatial and temporal heterogeneity in tumor blood flow. In addition, solid pressure generated by proliferating cancer cells compresses intratumoral blood and lymphatic vessels, which further impairs not only the blood flow but also the lymphatic flow. Collectively these vascular abnormalities lead to an abnormal tumor microenvironment characterized by interstitial hypertension (elevated hydrostatic pressure outside the blood vessels), hypoxia, and acidosis. The resultant hypoxia promotes invasion, metastasis and malignancy (Gatenby and Gillies, 2004; Sullivan and Graham, 2007). Tumor hypoxia, together with hypoperfusion and increased interstitial tumor pressure, impede the delivery and efficacy of anti-cancer drugs (Teicher, 1994). Hypoxia renders tumor cells resistant to both radiation and several cytotoxic drugs. Independent of these effects, hypoxia also induces genetic instability and selects for more malignant cells with increased metastatic potential. Hypoxia and low pH also compromise the cytotoxic functions of immune cells that infiltrate a tumor. Unfortunately, cancer cells are able to survive in this abnormal microenvironment. In essence, the abnormal vasculature of tumors and the resulting abnormal microenvironment together pose a formidable barrier to the delivery and efficacy of cancer therapy. Vessel normalization has therefore gained interest as a therapeutic option to improve drug delivery and anti-cancer treatment (Jain, 2005). Nonetheless, current antiangiogenic agents induce tumor hypoxia by pruning vessels or by inducing the formation of hypoperfused vessels; since hypoxia is a stimulus for angiogenesis, it may limit the therapeutic success of these drugs (Bergers and Hanahan, 2008; Casanovas et al., 2005; Franco et al., 2006). Increasing doses of drugs and/or oxygen has not shown much success in the clinic. One reason for this failure is that tumor vessels have large holes in their walls. As stated earlier, this leakiness leads to interstitial hypertension as well as spatially and temporally non-uniform blood flow. If the delivery system is flawed, it does not matter how much material is pumped into it. The drugs and oxygen will become concentrated in regions that already have enough and will still not reach the inaccessible regions.

Endothelial cells at the forefront of a sprouting vessel acquire a unique "tip cell" specification, which shares similarities with a navigating growth cone of axons; this fate is distinct from the "stalk cell", which trails behind the tip cell (Gerhardt et al., 2003). Tip cells navigate by extending filopodia, which sense environmental cues when homing to avascular targets (Gerhardt et al., 2003; Hellstrom et al., 2007). Both cell types are characterized by distinct molecular signatures (Gerhardt et al., 2003; Hellstrom et al., 2007). Much less is known about the more quiescent endothelial cell type in non-growing vessels, which survive for years, maintain lumen patency and form a tightly aligned, orderly shaped, smooth endothelial layer with a typical cobblestone appearance.

Since supply of oxygen is an ancestral function of vessels, we hypothesized that vessels should possess mechanisms to sense and adapt to changes in oxygen supply and, hence, perfusion in case of oxygen shortage. The oxygen sensing prolyl hydroxylase domain proteins (PHD1-3) target hypoxia-inducible transcription factors (HIFs) for degradation (Epstein et al., 2001; Kaelin and Ratcliffe, 2008). When oxygen tension drops, PHDs become less active, upon which HIFs may mount an adaptive response, such as angiogenesis. Hypoxic activation of HIF-1 induces angiogenesis by upregulating angiogenic factors (Forsythe et al., 1996; Semenza, 2003). However, severe hypoxia in tumors causes excessive release of angiogenic cytokines and, thereby, tumor vessel abnormalization (Bergers and Hanahan, 2008; Jain, 2005).

The role of the oxygen sensors in angiogenesis has not been extensively studied so far. Pharmacological inhibition of PHDs, silencing of PHD2 or generalized inactivation of PHD2 after birth stimulates angiogenesis, e.g., through upregulation of angiogenic factors in parenchymal cells (Milkiewicz et al., 2004; Nangaku et al., 2007; Takeda et al., 2007; Wu et al., 2008). The role of PHD2 in endothelial cells remains, however, more enigmatic. One study documented that overexpression of PHD2 in immortalized endothelial cells suppresses proliferation via hydroxylase-independent mechanisms (Takeda and Fong, 2007). It is, however, unknown whether PHDs regulate endothelial morphogenesis, vessel normalization or oxygen delivery. Here, we studied the role of PHD2 in this process, using tumor vessel abnormalization as a model. Since PHD2 influences tumor growth and indirectly thus also tumor angiogenesis (Lee et al., 2008), we selectively dissected the role of PHD2 in stromal cells in chimeric tumors, generated by implanting wild type (PHD2+/+) tumor cells in mutant (PHD2+/−) mice.

BRIEF SUMMARY OF THE INVENTION

As stated above, abnormal vasculature and the accompanying lack in perfusion, e.g., as encountered in solid tumors, is a major reason why drugs do not reach their target tissues or target sites. While this is certainly true for tumors, it applies to all cases where correct vasculature is compromised (by growth or excessive growth of aberrantly shaped vessels, e.g., in tumors, as well as by lack of vessel formation, e.g., in blood vessel ischemic disease or ischemic vascular disease). By fixing the vasculature that delivers drugs to target tissues or target sites, more cells are likely to encounter an effective concentration of drugs and oxygen. This is the rationale for developing therapies that normalize the (e.g., tumor) vasculature. These therapies do not merely increase the total uptake of drugs and oxygen but also distribute these molecules to a larger fraction of the (e.g., tumor) cells by fixing the delivery system.

According to one aspect, a method is provided of increasing perfusion in a tissue comprising inhibition of PHD2. In particular, the inhibition of PHD2 is only partial inhibition (e.g., from 25-75% inhibition). Concomitantly or alternatively, PHD2 inhibition may be specific to endothelial cells. As it was found that inhibition of PHD2 increases perfusion in blood vessels, it follows that agents transported through the blood vessels can be more efficiently delivered. This is beneficial for all agents, but it is particularly beneficial for those agents that are toxic.

Thus, according to a further particular aspect, inhibition of PHD2 is used in combination with an agent, or a therapy, that causes iatrogenic effects. Iatrogenic effects refer to inadvertent adverse effects or complications caused by or resulting from the medical treatment (agent or therapy). In particular embodiments, the iatrogenic effects include or are iatrogenic tissue damage. As many agents are known to have iatrogenic effects (toxicity accompanying a beneficial effect), in better perfused vessels, lower concentrations of the agents can be administered to achieve a same level of penetration (and thus a similar beneficial effect), while resulting in less side effects. Alternatively, the same concentration can be administered, resulting in higher efficacy, but without increasing side effects.

In principle, all tissues or organs can be affected by iatrogenic damage, depending on the nature of the agent or therapy and the mode of administration. Particular tissues/organs known to be affected by iatrogenic damage include heart, kidney and liver. The latter two organs are indeed involved in clearance of agents from the body, which may account for an increased susceptibility to toxic effects. According to specific embodiments, the agent causing iatrogenic effects such as tissue damage is a contrast agent or a chemotherapy agent, or the therapy causing tissue damage is radiotherapy or chemotherapy. Contrast media, while very useful in diagnostics, are known to cause contrast (medium)-induced nephropathy (CIN or CMN) because of their nephrotoxicity, and are a major cause of acute renal failure especially in hospitalized patients or patients with previous renal impairment (Sterling et al., 2008; ten Dam et al., 2008). Radiotherapy and chemotherapy are among the most well-known causes of iatrogenic tissue damage, as they often destroy healthy cells as well as tumor cells. When administering agents (such as contrast media or chemotherapy or other drugs), it can easily be understood that increased perfusion in blood vessels will help with delivery of the agent. However, the beneficial effects also apply for therapies that do not involve direct delivery of an agent. For instance, it has been well established that tumor hypoxia can reduce the effects of, e.g., radiotherapy (see, e.g., Vaupel et al., 2004). By increasing perfusion, hypoxia will be reduced. Thus, also for therapies that do not involve direct administration of an agent through blood vessels, such as radiotherapy, PHD2 inhibition has beneficial effects.

The methods provided herein can be used for the treatment of cancer, in particular for treatment of metastatic cancer or cancer at increased risk for metastasis (such as larger cancers with increased hypoxia). It is indeed well documented that hypoxia is accompanied with an increased risk of metastasis, thus reducing hypoxia by improving perfusion will reduce metastasis (as also shown in the examples). PHD2 inhibition may also be used in combination with an anti-cancer therapy selected from radiotherapy or chemotherapy in order to reduce organ damage as compared to treatment with the anti-cancer therapy alone. The combination may entail PHD2 inhibition before, during or after the other therapy, or they may, e.g., be intermittently changed or alternated. Particularly prior inhibition and/or concomitant inhibition of PHD2 is envisaged, as the change in blood vessel architecture induced by PHD2 inhibition allows a more efficient administration of the other therapy, or results in better effects. The combination of radiotherapy with PHD2 inhibition is particularly envisaged, as PHD2 inhibition decreases hypoxia, and hypoxia is known to reduce effectiveness of radiotherapy. The combination of chemotherapy with PHD2 inhibition is particularly useful as antineoplastic agents are by their nature cytotoxic for, inter alia, healthy dividing cells as well as tumor cells. Increasing perfusion by PHD2 inhibition results in more efficient delivery of these agents, thus requiring less of the cytotoxic agent(s) to reach therapeutic effects—by reducing the amount of cytotoxic or iatrogenic drugs, the risk of cytotoxic or iatrogenic effects is also reduced. Particularly envisaged forms of chemotherapy comprise treatment with a platinum-based chemotherapeutic drug such as cisplatin or a family member (known for its nephrotoxic effects) and/or an anthracycline antibiotic such as doxorubicin (known for its cardiotoxic effects).

Alternatively, the methods presented herein can be used in any disease or condition in which blood vessel architecture has gone awry, and/or in which blood vessel normalization is beneficial and/or in which increased perfusion is desired. Thus, the methods may for instance also be used for the treatment of macular degeneration, for treatment of ischemia or to induce vascular remodeling. It is envisaged that PHD2 inhibition will be beneficial for all disorders characterized by ischemia: as ischemia is characterized by a restriction in blood supply, the increase in perfusion following PHD2 inhibition treats the ischemia itself and not particular features of a given ischemic disorder. Nevertheless, particularly envisaged disorders in which ischemia occurs include, but are not limited to: limb ischemia or critical limb ischemia, chronic obstructive pulmonary disease, ischemia-reperfusion injury, post-operative ischemia, diabetic ischemic disease such as diabetic retinopathy, ischemic cardiovascular disease, restenosis, acute myocardial infarction, chronic ischemic heart disease, atherosclerosis, ischemic stroke, ischemic cerebral infarction, or ischemic bowel disease.

Notably, the increase in perfusion is normally due to a change in morphogenesis or shape of blood vessels, but not due to change in number of vessels. Thus, PHD2 inhibitors may be used to increase perfusion. One example of a PHD2 inhibitor is a siRNA specific to PHD2, such as for instance the shRNA described by Chan et al. (2009).

DETAILED DESCRIPTION OF THE INVENTION

Definitions

Figure 1:
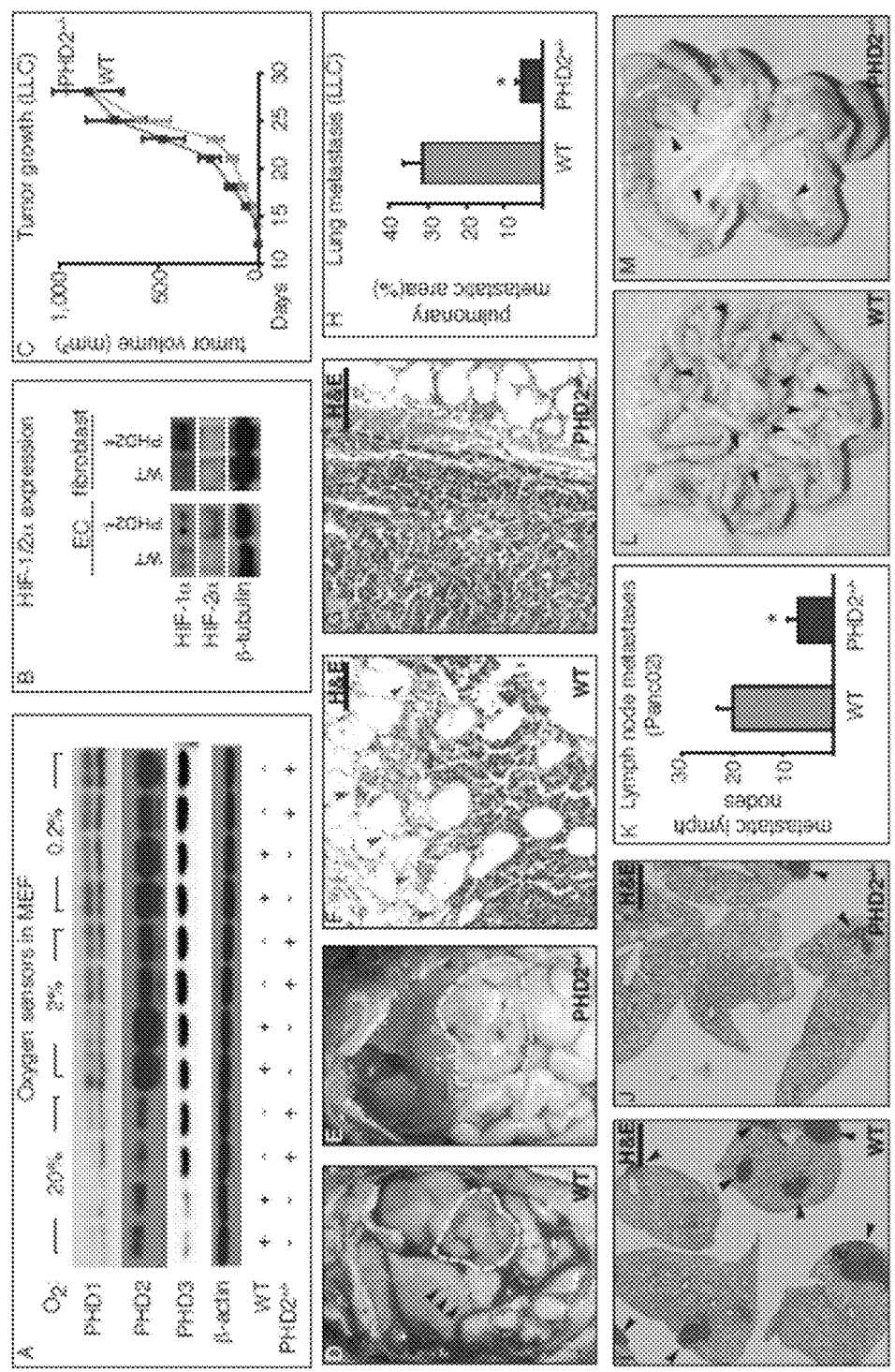
FIG. 1: REDUCED TUMOR INVASION AND METASTASIS IN PHD2+/− MICE. A,B, Immunoblot of PHDs in mouse embryonic fibroblasts (MEF) (A) and of HIFs in ECs and fibroblasts (B). C, Growth of LLC tumors (N=8; P=0.33). D,E, Panc02 tumors (yellow line) are more invasive and metastatic in WT than PHD2+/− mice, evidenced by hemorrhagic ascites, metastatic nodules (blue line), jaundiced liver and liver metastases (arrowheads). F,G, H&E staining, showing infiltrative B16 tumor foci in WT mice (F; arrowheads) but encapsulated borders in PHD2+/− mice (G; dashed line). H, Reduced metastasis of LLC tumors in PHD2+/− mice (N=8; P<0.0001). I,J, H&E staining, revealing fewer pulmonary metastatic LLC tumor nodules in PHD2+/− mice (arrowheads). K, Reduced metastasis of Panc02 tumor cells in PHD2+/− mice (N=27; P=0.0001). L,M, Macroscopic view, showing more metastatic mesenteric lymph nodes (arrowheads) in WT (L) than PHD2+/− (M) mice. Bar: 50 μm in F,G,I,J. Asterisks in H,K denote statistical significance. Error bars in C,H,K show the standard error of the mean (SEM); all subsequent error bars are defined similarly.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

As used herein, the term "perfusion" refers to the process of nutritive delivery of (arterial) blood to a capillary bed in the biological tissue. Nutritive delivery particularly relates to delivery of oxygen, nutrients and/or agents carried in the blood stream.

The term "to increase" or "increasing" as used herein, especially in relation to perfusion or perfusion-related effects in the context of PHD2 inhibition, means that levels of the variable under study are higher (i.e., increased) compared to the levels of this variable in a situation where such inhibition does not take place. This does not automatically imply that the levels of this variable are increased when compared to baseline levels, as it is particularly also envisaged that better preservation of baseline levels falls under this definition. For instance, when administering a cardiotoxic drug such as doxorubicin, the perfusion in the heart will drop in WT animals, but remains largely preserved in PHD2 heterozygous animals (see, Examples). While perfusion in this case is not higher than baseline, perfusion is increased as it is higher than the same situation where no PHD2 inhibition occurs. The same applies mutatis mutandis for the term "decrease" in the context of perfusion or perfusion-related effects in PHD2 inhibition.

The term "partial inhibition of PHD2" as used throughout the application refers to inhibition that takes place but is not complete. Inhibition, and partial inhibition, can occur at different levels, e.g., at the DNA, RNA or protein level, for example using genetic knock-out, siRNA or antibodies, but regardless the mode of inhibition, it should ultimately result in less functional PHD2 activity being present. Partial inhibition of PHD2 then typically relates to a 5 to 95% decrease in functional PHD2 activity (as compared to the non-inhibited situation), a 10 to 90% decrease, a 20 to 80% decrease, a 25 to 75% decrease, a 30 to 70% decrease in PHD2 activity. According to specific embodiments, a 40 to 60% decrease in PHD2 activity, a 45 to 55% decrease in PHD2 activity or even a 50% decrease in PHD2 activity is envisaged.

"Endothelial cells" as used herein are cells that are part of the endothelium, the thin layer of cells that line the interior surface of blood vessels. Cells can be characterized as endothelial cells by the expression of specific markers, such as CD31.

The term "iatrogenic effects" as used herein refers to inadvertent adverse effects or complications caused by or resulting from medical or diagnostic treatment. Colloquially this can also be referred to as side effects, but it is to be understood that the term iatrogenic implies that the compound or therapy causing these effects is actually intended to heal or diagnose the patient receiving the compound/therapy (the Greek "iatros" meaning 'healer'), and iatrogenic effects are often quite harmful—'adverse effects of a therapy' could in some instances be used as a synonym.

An "agent or therapy causing iatrogenic effects" thus are agents (or therapies) that are in first instance intended to benefit the patient receiving them (by treating or diagnosing an existing condition or disorder), but may in doing so provoke unwanted effects. Many examples of such agents and therapies exist, including but not limited to, nonsteroidal anti-inflammatory drugs (NSAIDs), antibiotics, amphotericin B, antiviral agents, angiotensin-converting enzyme (ACE) inhibitors, calcineurin inhibitors, radiocontrast media, and cytostatics. Particular therapies that are also envisaged within the definition include therapies that are cytotoxic by nature, such as radiotherapy or chemotherapy. Chemotherapy drugs (or agents) that cause iatrogenic effects include, but are not limited to, alkylating agents, antimetabolites, anthracyclines, platinum analogues, plant alkaloids, antimitotics, and topoisomerase inhibitors. Other agents well known to cause iatrogenic effects include contrast media, including but not limited to, hyperosmolar contrast agents typically composed of relatively small, negatively charged iodinated molecules, such as diatrizoate; lower osmolar nonionic contrast agents, typically monomers of iodinated benzene rings (e.g., iohexyl, iopamidol); iso-osmolar contrast medium, e.g., a nonionic dimer such as iodixanol.

"Platinum-based chemotherapeutic drugs" or "platinum analogues" as used herein refer to drugs containing a platinum molecule that damage DNA by permanently coordinating to DNA to interfere with DNA repair. These include, but are not limited to, platinum, cisplatin, carboplatin, nedaplatin, oxaliplatin, satraplatin and triplatin tetranitrate.

An "anthracycline antibiotic" as used throughout the application refers to a class of drugs derived from *Streptomyces* bacteria used in cancer chemotherapy. These include, but are not limited to, doxorubicin, daunorubicin, epirubicin, idarubicin and valrubicin.

The term "ischemia" as used herein refers to a restriction in blood supply due to a blood vessel related factor. An ischemic disorder is any disorder characterized by ischemia.

With the term "vascular remodeling" as used in the application, the remodeling of blood vessels is meant. "Remodeling" should be understood as changing the morphogenesis or shape of the blood vessels, without affecting the number of vessels, in such a way that the vessels become more functional. Functional in this context implies that they are less leaky, less tortuous, allow more blood flow (perfusion), have an increased diameter, or are characterized by other parameters of PHD2+/− vessels as described herein. "Vascular remodeling" as used herein thus refers the process of forming functional vessels from non-functional vessels (e.g., resulting from non-productive angiogenesis).

This study identifies a novel basic biological role for endothelial PHD2 in oxygen delivery by regulating vessel morphogenesis. Our data suggest a model, whereby a decrease in the activity of PHD2 in ECs in hypoxia counteracts abnormalization of the EC layer. This involves a shift from an endothelial tip to a distinct phenotype, referred to here as the "phalanx phenotype", and relies in part on HIF-mediated upregulation of (soluble) Flt1 and VE-cadherin. EC normalization provides a feedback mechanism for vessels to readjust their shape, not number, in order to optimize oxygen supply when the latter is insufficient.

Figure 7:
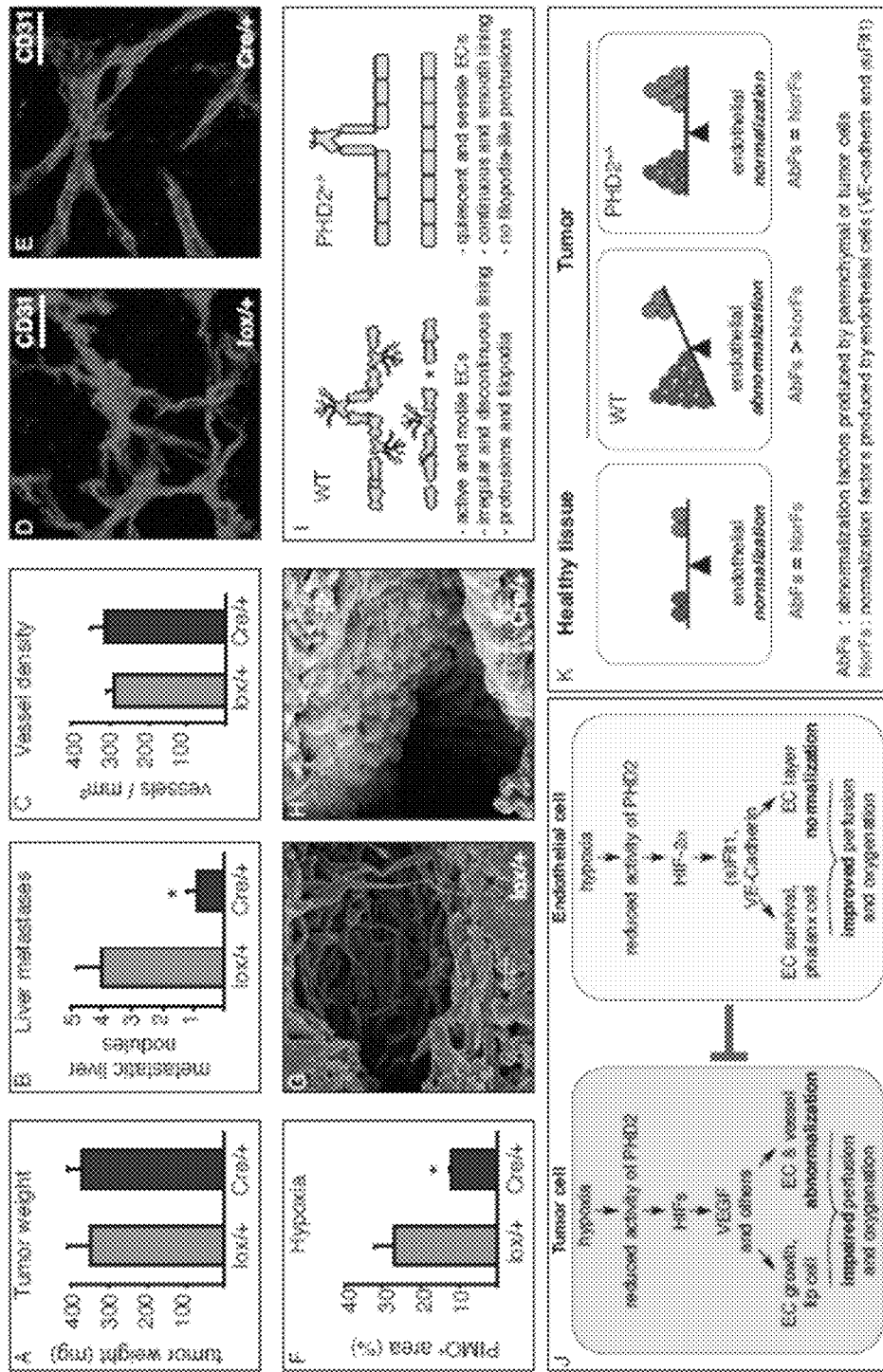
FIG. 7: PHENOTYPIC CHARACTERIZATION OF PHD2CRE/+MICE. A-F, Phenotype of PHD2Cre/+ mice with endothelial PHD2 haplodeficiency (Cre/+) and PHD2lox/+ (lox/+) littermates. Panc02 tumor weight (A), vessel density (C) and microvascular architecture (D,E) are comparable, but metastasis (B) and hypoxia (F) are reduced in PHD2Cre/+ mice (N=10; P<0.05). Whole mount CD31 staining and SEM reveal that, in contrast to PHD2lox/+ mice (D,G), the tumor endothelial layer is normalized in PHD2Cre/+ mice (E,H) (see FIG. 4F-H for comparison). I, Scheme of key EC phenotypes. In abnormalized tumor vessels in WT mice, hypermotile endothelial tip-like cells protrude filopodia in the lumen and perivascular stroma, and abnormally shaped ECs (irregular cell border) form a pseudostratified, loosely attached layer, while other vessel areas become denuded (asterisk). In more normalized tumor vessels in PHD2+/− mice, ECs shift to a phalanx-like phenotype (smooth, regular cell border), characterized by EC survival, tightness and quiescence, which improves tissue perfusion and oxygen delivery. For reasons of clarity and simplicity, not all phenotypic features (such as for instance, coverage by mural cells) are depicted. J, PHD2 model. Left: hypoxic tumor cells induce endothelial abnormalization by release of VEGF and other abnormalization factors, which impairs perfusion and causes hypoxia. Right: ECs counteract this abnormalization switch, in part through upregulation of (s)Flt1 and VE-cadherin, thereby improving vessel perfusion and oxygenation. This pathway is more effective in PHD2+/− mice, because endothelial PHD2 haplodeficiency resets oxygen sensing and makes them better (pre)-adapted to hypoxia. K, Scheme of the endothelial abnormalization switch. Left: In healthy tissues, the production of abnormalization factors (AbFs) by (non-endothelial) parenchymal cells is in balance with the production of normalization factors (NorFs) by ECs, resulting in EC normalization. Middle: In tumors in WT mice, excess production of tumor cell-derived AbFs over EC-derived NorFs tilts the balance in favor of EC abnormalization. Right: In tumors in PHD2+/− mice, haplodeficiency of PHD2 upregulates the production of NorFs by ECs, thereby counteracting EC abnormalization; the resultant improved oxygenation lowers the production of AbFs by tumor cells, overall reequilibrating the balance in favor of EC normalization. Bar: 50 μm in F,G. Asterisks in B,F denote statistical significance.

In healthy tissues, "productive" angiogenesis generates perfused blood vessels and improves oxygenation. By contrast, tumor angiogenesis is often "non-productive" as vessel abnormalization impairs oxygen supply (Jain, 2005). The importance of vessel normalization for tumor growth and treatment is being increasingly recognized, but its relevance for metastasis remained unknown (Hamzah et al., 2008; Kashiwagi et al., 2008; Stockmann et al., 2008; Winkler et al., 2004). PHD2 haplodeficiency promoted endothelial rather than vessel normalization (FIG. 7I). The resultant tightened endothelial barrier, improved tumor oxygenation, and downregulation of metastatic genes can explain why PHD2 haplodeficiency suppressed tumor invasion, intravasation and metastasis. Thus, a change in endothelial shape, even without alterations in vessel numbers, sufficed to induce a shift to reduced malignancy and metastasis.

Hypoxic cancer cells stimulate angiogenesis by upregulating factors such as VEGF (Semenza, 2003); this response is controlled by PHD2 (Lee et al., 2008). When released by tumor cells in excess, these angiogenic factors turn into EC "abnormalization factors" (AbFs), which induce non-productive abnormalized vessels. This may initiate a vicious self-sustaining cycle, in which EC abnormalization impairs tumor perfusion and aggravates hypoxia, which will then upregulate AbFs in tumor cells even more and, in turn, amplify EC abnormalization again. PHD2+/− ECs counteract this process by re-installing EC normalization (or preventing its abnormalization altogether). Indeed, they upregulate EC "normalization factors" (NorFs) such as (soluble) Flt1 and VE-cadherin, which antagonize the activity of AbFs. EC normalization in turn will increase tumor oxygenation, and interrupt the vicious cycle of EC abnormalization, driven by hypoxic tumor cells. Together, WT tumor cells induce vessel abnormalization and impair oxygen supply, while PHD2+/− ECs counteract this process in a negative feedback, and readjust oxygen supply by promoting endothelial normalization. A reduction of PHD2 activity by hypoxia in WT ECs will also trigger the EC normalization program, but less efficiently than haplodeficiency of PHD2 (see below). This model is schematically illustrated in FIG. 7J,K.

The responses of endothelial and tumor cells to hypoxia are tightly linked, since the activity of PHD2 coordinately changes in function of the oxygen tension. Thus, when oxygen levels drop (and decrease the activity of PHD2 in tumor and ECs), the absolute levels of AbFs and NorFs will coordinately rise. Since tumor cells produce more AbFs than ECs produce NorFs, their relative balance likely even tilts over to more EC abnormalization in severe hypoxic conditions. This may explain why hypoxic suppression of PHD2 in ECs in WT mice cannot overcome the strong abnormalization response by tumor cells. By rendering ECs better pre-adapted to hypoxia than tumor cells, haplodeficiency of PHD2 re-equilibrates this balance in favor of the EC normalization response; this indirectly affects tumor cells as well, since, as a result of the improved oxygenation, tumor cells will now also produce fewer AbFs (FIG. 7K). This model therefore predicts that pharmacological inhibition of PHD2, selectively, in ECs may also induce vessel normalization. In physiological conditions, the relative balance between EC abnormalization and normalization is more in equilibrium (FIG. 7K). Ongoing studies suggest that PHD2 haplodeficiency also normalizes vessels in other pathological conditions (e.g., macular degeneration, ischemia, for inducing vascular remodeling), suggesting that it has a more general role than in cancer alone (unpublished).

PHD2 haplodeficiency did not affect the number of tumor vessels. This may seem paradoxical to the observation that the migratory and mitogenic responses of PHD2+/− ECs to VEGF are impaired. However, these impaired responses are balanced off by an increased survival response to VEGF, while their responsiveness to other molecules (such as FGF-2) is still preserved. Also, an increased EC motility may not necessarily generate more vessels. We speculate that hyper-motile WT ECs "move around" and leave their resident position more often. As a result, existing vessels become denuded and regress, while new naked vessels are formed coincidentally. When both processes are in balance, tumor vessel density remains unchanged. By contrast, PHD2+/− ECs are more sessile and, once lining a vessel, "stay put", thereby reducing non-productive remodeling of vessel regression and sprouting. Hence, by being more "passive" and quiescent, PHD2+/− tumor vessels maintain their numbers. It will be shown in the examples that, while the absolute vessel number and the vessel density are not influenced by PHD2 inhibition, PHD2+/− vessels are better perfused, increasing functional vessel number and density (and thus showing increased productive remodeling of vessels).

Upregulation of VE-cadherin is a likely mechanism underlying EC normalization. Indeed, VE-cadherin inhibits EC proliferation and apoptosis, and tightens the barrier (Carmeliet et al., 1999; Taddei et al., 2008). It also induces a "normalized, stabilized, quiescent" EC phenotype indirectly, by inhibiting proliferation and promoting survival in response to VEGF (Carmeliet et al., 1999; Lampugnani et al., 2003). The VEGF-trap sFlt1 also participates in fine-tuning EC normalization. Interestingly, a pericellular gradient of sFlt1 improves vessel morphogenesis more than mFlt1 (Kappas et al., 2008; Kearney et al., 2004). It remains to be determined how PHD2 interacts with other "normalization" pathways, such as nitric oxide, Tie2, MMPs, myeloid-derived VEGF, Rgs5 or PDGFR-β (Greenberg et al., 2008; Hamzah et al., 2008; Kashiwagi et al., 2008; Stockmann et al., 2008; Winkler et al., 2004).

Endothelial tip and stalk cells each have their own molecular signature (Gerhardt et al., 2003; Hellstrom et al., 2007). Phalanx cells might represent another type of ECs with a distinct identity: unlike tip cells, they extend few filopodia and migrate poorly in response to VEGF, form a tight barrier and vascular lumen, and express elevated levels of (soluble) Flt1 and VE-cadherin. They resemble stalk cells by depositing basement membrane and establishing junctions, but differ by their increased quiescence, and reduced mitogenic response to VEGF. We speculate that these three EC phenotypes should not be considered as non-overlapping identities, but, more likely, belong to a spectrum of phenotypes, whereby tip and phalanx cells represent the extreme examples of either the most navigatory or the most sedentary, quiescent cell type. Possibly, even though some of the genes are expressed by each of the three cell types, different threshold levels or qualitative signaling properties may specify each cell type.

Figure 17:
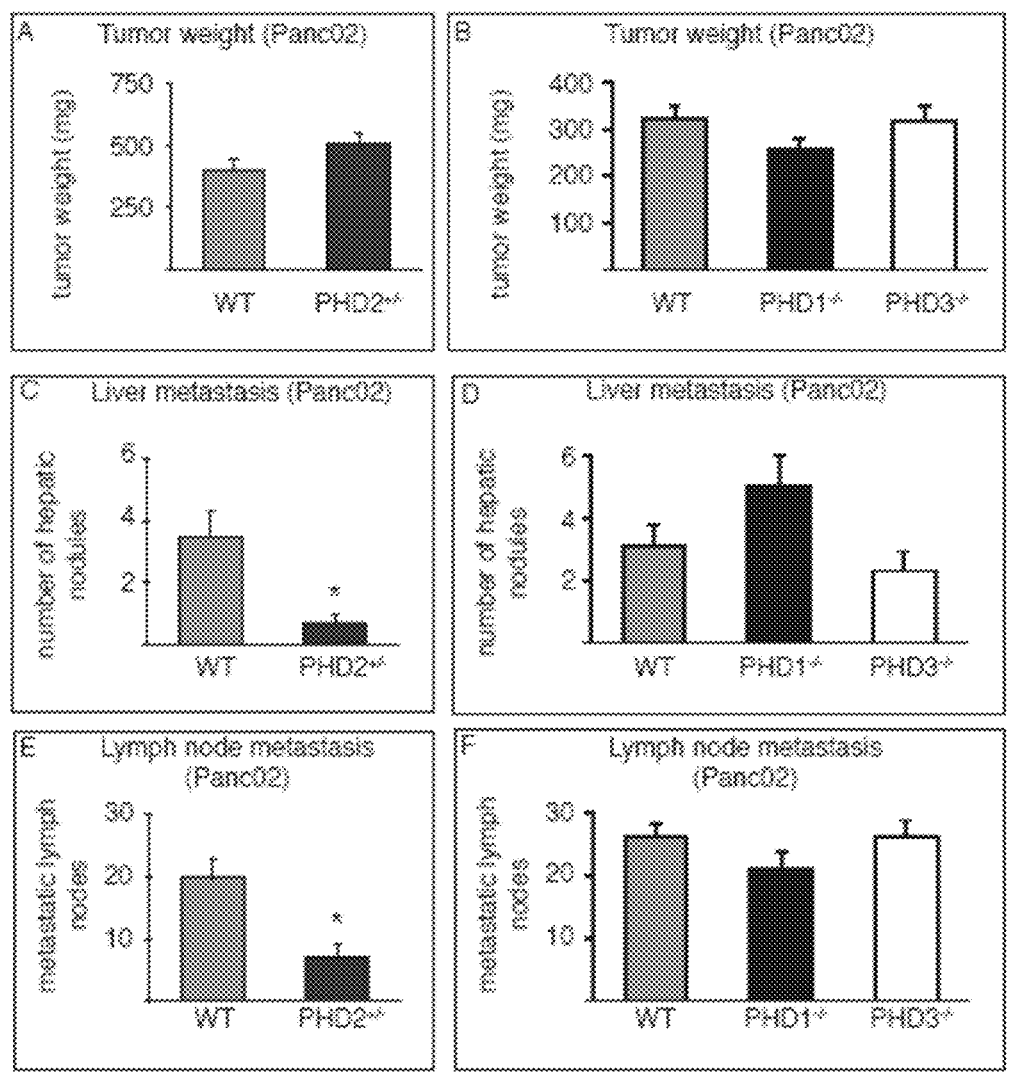
FIG. 17: REDUCED METASTASIS IN PHD2+/−, BUT NOT PHD1−/− OR PHD3−/− MICE. A, Panc02 tumors implanted in WT and PHD2+/− mice exhibit comparable weight. B, Similarly, tumors implanted in PHD1−/− and PHD3−/− mice show no significant differences comparing to the WT counterparts. C-F, Metastasis is reduced in PHD2+/− mice (C,E), but not in PHD1−/− or PHD3−/− (D,F), as analyzed by counting the number of metastatic hepatic and lymphatic nodules. Asterisks in panels C,E denote statistical significance (P<0.05). See also FIG. 1K.

Without being bound by any particular mechanism, our data seem to suggest that HIF-2α is involved in EC normalization induced by PHD2 inhibition. Consistent herewith, reduction of HIF-2α impairs vessel morphogenesis (Peng et al., 2000) and induces aberrant vascular networks (Yamashita et al., 2008). Also, HIF-2α binds to hypoxia responsive elements in the VE-cadherin and Flt1 promoter in ECs (Dutta et al., 2008; Le Bras et al., 2007). Moreover, since HIF-2α is relatively resistant to degradation at oxygen levels that normally lead to degradation of HIF-1α (Lofstedt et al., 2007), it may be relevant in maintaining vessel normalization in better oxygenated (normalized) vessels. Nonetheless, given the dynamically changing tumor oxygen microenvironment, we cannot exclude that upregulation of HIF-1α may also contribute to vessel normalization. It should be noted that the observed effects are specific for PHD2, as PHD 1 and PHD3 inhibition failed to reduce tumor metastasis (FIG. 17). This also implies that mere upregulation of HIF (HIF-2α or HIF-1α), as results from PHD1 or 3 inhibition, is probably not sufficient to induce EC normalization, but that PHD2 inhibition is needed. In this regard, it is worth mentioning that, while silencing of PHD1 or PHD3 has already been shown to upregulate HIFs previously (Appelhoff et al., 2004; Ginouves et al., 2008), we have never observed any vascular or other phenotype in heterozygous deficient PHD3 mice, in which PHD3 levels are also partially reduced, but not completely absent. Of note, a recent article (Chan et al., 2009) shows HIF-independent effects of PHD2 on blood vessel growth.

Implantation of fibroblasts, in which PHD2 expression was completely silenced, stimulates angiogenesis in healthy WT mice through release of angiogenic factors (Wu et al., 2008). In another study, inducible broad-spectrum inactivation of PHD2 after birth (PHD2IND-KO) induced growth of supernumerary vessels in healthy organs (Takeda et al., 2008; Takeda et al., 2007). It remains unclear whether the vascular changes in PHD2IND-KO mice are secondary to the high hematocrit levels, hyperviscosity, thrombosis and cardiac dysfunction, or to elevated circulating VEGF levels (Minamishima et al., 2008; Takeda et al., 2007). An alternative explanation may relate to the hydroxylation-independent activity of PHD2, but this effect has been only identified in immortalized ECs so far (Takeda and Fong, 2007). Since only complete PHD2 inactivation caused spontaneous vessel changes, PHD2 controls vessel number versus morphogenesis in a gene-dosage dependent manner.

Finally, our findings suggest possible medical implications. By normalizing the tumor vasculature, endothelial haplodeficiency of PHD2 may shift tumors to a less malignant, metastasizing phenotype. As oxygenation levels determine responsiveness to irradiation and chemotherapy, inhibition of PHD2 might improve anti-cancer therapy (unpublished). PHD2 inhibitors may represent a novel class of anti-vascular agents that, in contrast to traditional anti-angiogenic therapy, regulate vessel shape, but not their size or numbers. As quiescent vessels in healthy tissues are not affected in PHD2+/− mice, inhibition of PHD2 selectively targets tumor vessels. These findings may further be confirmed in spontaneous tumor models. Also, strategies to deliver such compounds selectively to ECs should be explored. In conclusion, our studies provide novel insight in how oxygen sensors help to shape the microvasculature for one of its most important functions, i.e. supplying oxygen to cells.

Experiments included herein and still ongoing experiments have already shown that treatment of tumors in PHD2+/− mice with anti-cancer agents like doxorubicin or cisplatin not only show an improved effect of the anti-cancer therapy (without being bound to the mechanism, this is likely due to increased perfusion and thus at least in part due to more efficient delivery of the anti-cancer agent and/or the more efficient delivery of oxygen) as compared to treatment of wild-type mice, but also considerably less organ damage. Results from hind limb ischemia models and age-related macular degeneration models also show promise for PHD2 inhibition as therapy. The following examples are offered to better understand the current invention. Although they can help in interpreting the invention, it is understood that the invention is limited only by the claims.

EXAMPLES

Experimental Methods

SYNGENEIC TUMOR MODELS: 5 105 B16F10.9 melanoma and 105 Lewis lung carcinoma (LLC) cells were injected subcutaneously into the right flank or foot pad, respectively. Tumor volumes were measured every two days with a caliper using the formula: $V=\pi \times [d2 \times D]/6$, where d is the minor tumor axis and D is the major tumor axis. 106 Panc02 tumor cells (donated by B. Wiedenmann, Charite, Berlin) were injected into the head of the pancreas. At day 10, primary tumors were removed and weighed. The incidence of tumor invasion into adjacent organs, hemorrhagic ascites, and mesenteric lymph node metastases were recorded. Circulating tumor cells were scored on 1 ml of peripheral blood upon red blood cell lysis.

HISTOLOGY AND ELECTRON MICROSOPY: All methods for histology and immunostaining have been described (Fischer et al., 2007). For electron microscopy analysis, mice were perfused with 2% PFA and 2.5% glutaraldehyde in 0.1 M Na-cacodylate buffer for 7 min. Organs were dissected, cross-sectioned and fixed o/n in the same solution. The next day samples were postfixed with 2% osmium tetroxide and dehydrated in a graded acetone series. Afterwards, the samples were critical-point dried (Balzers CPD 030), mounted on stubs and coated with gold (SPI-MODULE™ Sputter Coater, SPI Supplies). Images were obtained with a scanning electron microscope (JEOL JSM-6360) at 15 kV.

IN VITRO BIOLOGICAL ASSAYS: Primary endothelial cells (ECS) were derived from lungs as described (Kuhlencordt et al., 2004). After cell recovery, the following assays were performed. PROLIFERATION AND APOPTOSIS ASSAY: 5 105 ECs were seeded in gelatin-coated 24-well plate. Subconfluent cell layers were either not stimulated or stimulated with 50 ng/ml VEGF. Proliferation was assessed upon BrdU incorporation and staining with FITC-conjugated anti-BrdU according to the manufacturer's instructions (BD Bioscience). TUNEL staining was performed according to manufacturer's instructions (In situ cell death detection kit, Roche). MOTILITY ASSAY: subconfluent cell layers were seeded on a fibronectin-coated 35 mm tissue culture dish and scratched in the absence or presence of VEGF or FGF-2 (50 ng/ml). Images were acquired for 6-14 h taking an image every 15 min. Quantification of LAMELLIPODIA and FILOPODIA was performed as described (Kitamura et al., 2008; Sheldon et al., 2008).

PROTEIN ANALYSIS: The following antibodies were used: rabbit anti-PHD1 (generated by P. Ratcliffe), rabbit anti-PHD2 (generated by P. Maxwell; and Novus), rabbit anti-PHD3 (Novus), rabbit anti-HIF-1, rabbit anti-HIF-2 (Novus), goat anti-VE-cadherin (R&D Systems), anti-FM (R&D Systems for the IP and Sigma for the WB), and anti-β-tubulin or anti-β-actin (Abcam). Concentrations of sFlt1 and VEGF-A were estimated by immunoassays (R&D Systems).

QRT-PCR: Quantitative RT-PCR was performed as described (Fischer et al., 2007). The Assay ID (provided by Applied Biosystems) or the sequence of primers and probes (when home-made) are listed in Table S2.

HYPOXIA ASSESSMENT AND TUMOR PERFUSION: Tumor hypoxia and perfusion were analyzed as described (Fischer et al., 2007). Vessel leakage was analyzed after intravenous co-injection of 0.25 mg Texas Red-conjugated Dextran 70 kD (Molecular Probes) and 0.05 mg FITC-labelled lectin (*Lycopersicon esculentum*; Vector Laboratories). Ten minutes later, mice were perfused with saline and 2% PFA. Tumors were then harvested and frozen in OCT compound.

OXYMETRY, LACTATE AND REDOX POTENTIAL: We measured tumor oxygen tension (pO2) using charcoal powder (100 g; CX0670-1; EM Science) as the oxygen-sensitive probe and an EPR spectrometer (Magnetech). Lactate concentration and [NADH/NAD+] ratio were measured as described (Noll, 1981; Pospisilik et al., 2007).

STATISTICS: Data represent mean±SEM of representative experiments unless otherwise stated. Statistical significance was calculated by t-test or two way-ANOVA where indicated (Prism v4.0b), considering P<0.05 as statistically significant.

ANIMALS: C57BL/6 mice (8-12 weeks old) were obtained from our mouse facility. Housing and all experimental animal procedures were approved by the Institutional Animal Care and Research Advisory Committee of the K.U. Leuven. SYNGENEIC TUMOR MODELS: Two subcutaneous and one orthotopic tumor models were used. IN VIVO SUBCUTANEOUS TUMOR MODELS: B16F10.9 melanoma and Lewis lung carcinoma (LLC) adherent growing murine cells were harvested and single-cell suspensions of 5 105 cells in 200 ml (B16) or 1 105 cells in 50 ml (LLC) of PBS were injected subcutaneously into the right flank or foot pad of syngeneic mice, respectively. Tumor volumes were measured every two days with a caliper using the formula: $V=\pi \times [d^2 \times D]/6$, where d is the minor tumor axis and D is the major tumor axis. The mice were sacrificed at defined time intervals after cell inoculation or when tumors reached a maximum size of 2 cm3. Growth curves were statistically analyzed using two way-ANOVA. Tumor and lungs were collected for histological analysis. For the LLC model, lung nodules were counted under a stereoscopic microscope. Alternatively the primary tumor was removed by leg amputation when reaching a volume of 800 mm$^3$ to allow further growth of metastatic nodules; in this model, survival is correlated with pulmonary metastasis (Gao et al., Science, 319, 195-198, 2008). For both models, H&E-stained tumor and lung sections were evaluated by the pathologist for tumor necrosis, invasion and metastasis. IN VIVO ORTHOTOPIC TUMOR MODEL: For orthotopic pancreatic tumor growth, mice were anesthetized with isoflurane, the stomach exteriorized via abdominal midline incision, and 106 Panc02 tumor cells in 30 μl PBS were injected into the head of the pancreas using a 29-gauge needle. A successful intrapancreatic injection of tumor cells was identified by the appearance of a fluid bleb without intraperitoneal leakage. Peritoneum and abdominal wall were closed with individual surgical sutures. At day 10, primary tumors were removed, and tumor weight and volume were analyzed as mentioned above. The incidence of tumor invasion into adjacent organs, hemorrhagic ascites, and mesenteric lymph node metastases were recorded. Tumor invasion and necrosis were histologically confirmed as above. All tumor growth experiments were repeated 3 to 8 times, each experiment comprising 6 to 10 mice per group (unless otherwise indicated). Tumor volume and weight shown in the figures and tables are means±SEM from one representative experiment.

CIRCULATING TUMOR CELLS: 1 106 GFP+ Panc02 tumor cells in 30 1 PBS were injected into the head of the pancreas. At day 12, primary tumors were removed and 1 ml of blood was collected in heparin. After lysing red blood cells, the cell pellet was washed in PBS and let to adhere on the plastic of a 6 cm-Petri dish. GFP+ cells were then counted under a fluorescent microscope.

IN VIVO COLONIZATION ASSAY: GFP+ B16 tumor cells were detached with EDTA and resuspended in PBS at a final concentration of 4 105 cell/ml; 200 ml of cell suspension was injected into the tail vein. After 18 days organs were harvested and weighed. Pulmonary and liver nodules were counted under a stereoscopic microscope. HISTOLOGY, IMMUNOSTAININGS AND MORPHOMETRIC ANALYSES: All methods for histology and immunostaining have been described (Fischer et al., Cell, 131, 463-475, 2007; Michieli et al., Cancer Cell, 6, 61-73, 2004). For serial sections cut at 8 μm thickness, tissue samples were immediately frozen in OCT compound or fixed in 2% PFA overnight at 4° C., dehydrated and embedded in paraffin. Thick sections (40 μm thickness) were cut after fixing tissue samples in 2% PFA overnight at 4° C., followed by an overnight treatment at 4° C. in 30% sucrose solution and frozen in OCT compound. Immunostainings were performed using the following primary antibodies: rat anti-CD31 (BD Pharmingen), rat anti-F4/80/Mac1, rat anti-CD45 (all Becton Dickinson), rabbit anti-fibrin(ogen) (Nordic), mouse anti-smooth muscle actin, mouse anti-vimentin, rabbit anti-cytokeratin (Dako), mouse anti-collagen IV, rabbit anti-laminin, rabbit anti-GFP (Molecular Probes), mouse anti-PCNA (Novacastra), rabbit anti-claudin-5, rabbit anti-ZO-1 (Zymed), goat anti-VE-cadherin and goat anti-CD105/endoglin (R&D System), rabbit anti-active caspase 3 (Abcam), rat antiextracellular Flt1 (Reliatech), rabbit anti-HIF-1 (Novus), rabbit anti-HIF-2 (generated by Patrick Maxwell), and rabbit anti-LYVE-1 (Cell Signalling) and rabbit anti-PHD2 (Lifespan). Sections were then incubated with the appropriate fluorescently conjugated secondary antibodies (Alexa 488 or 546, Molecular Probes) or with peroxidase-labeled IgGs (Dako), followed by amplification with the proper tyramide signal amplification systems when needed (Perkin Elmer, Life Sciences) when necessary. For double labelings, paraffin or cryo sections were stained with a rat anti-smooth muscle actin-Cy3 antibody (Sigma), rabbit anti-claudin-5, goat anti-VE-cadherin, rabbit anti-ZO-1, rabbit santi-GFP and the rat anti-CD31 antibody, followed by a secondary fluorophore-conjugated antibodies. Immune complex formation was determined by immunofluorescent staining for mouse IgGs on tissues of mice treated for 3-5 weeks. Morphometric analyses were performed using a Zeiss Axioplan microscope with KS300 image analysis software. Tumor inflammation was analyzed and expressed as the percentage of CD45+ or F4/80+ area over the total tumor area. To assess tumor endothelial cells proliferation, BrdU 200 mg/kg was injected i.p. After 8 h tumors were harvested and frozen in OCT medium. Co-immunostaining of rat anti-BrdU (Immunosource) and anti-CD105/endoglin (R&D were carried out on 4 m tumor sections. The same tumor sections were analyzed for endothelial apoptosis by coimmunostaining with anti-active caspase-3 and anti-CD105. For all the studies, 5-10 optical fields (20× or 40× magnification) per tumor section were randomly chosen and analyzed by using a Zeiss Axioplan microscope with KS300 image analysis software.

PHYSIOLOGICAL ANGIOGENESIS ASSAYS: Vasculature of yolk sacs was assessed at E9.5 as described (Rolny et al., Blood, 108, 1877-1886, 2006). Embryos at E9.5 and ovaries upon hormone induced-ovulation were processed by overnight fixation in 2% PFA, followed by de-hydration and re-hydration in consecutive series of methanol solutions (25-50-75-100%). After a short wash in PBS, samples were blocked in PBSMT (2% nonfat milk, 0.5% Triton x-100 in PBS). Incubations with both primary and secondary antibodies were done overnight at 4° C. followed by three washes of 1 h in PBSMT also at 4° C.

ELECTRON MICROSCOPY: Mice were anesthetized (60 mg/kg Nembutal), perfused with 2% PFA and 2.5% glutaraldehyde in 0.1 M Na-cacodylate buffer, pH 7.2-7.4 for 7 min. Organs were dissected, cross sectioned and fixed overnight in 2% PFA and 2.5% glutaraldehyde in Na-cacodylate buffer. After 24 h, 3 rinses of 30 min with 0.1 M Na-cacodylate buffer were followed by post-fixation with 2% osmiumtetroxide in 0.1 M Na-cacodylate buffer for 2 h at room temperature. Following dehydration in a graded acetone series (30-50-70-100%) the organs were critical-point dried (Balzers CPD 030). Critical-point dried tissues were mounted on stubs with double-sided adhesive carbon tape. The stubs were coated with gold (SPI-MODULE™ Sputter Coater, SPI Supplies, West Chester, Pa., USA). Images were obtained with a scanning electron microscope (JEOL JSM-6360) at 15 kV (KULeuven, Laboratory of Plant Systematics).

HEMATOLOGICAL ANALYSIS: Blood was collected in heparin with capillary pipettes by retroorbital bleeding, and white blood cell count determined using a hemocytometer.

CELLS AND CULTURE CONDITIONS: TUMOR CELLS: murine melanoma B16 clone F10.9, and the murine Lewis lung carcinoma (LLC) cell lines were obtained from American Type Culture Collection (ATCC). The murine pancreatic Panc02 tumor cell line was kindly provided by B. Wiedenmann (Charite, Berlin). B16F10.9 and LLC cell lines were maintained in DMEM (Gibco) containing 10% FBS, except Panc02 which was cultured in RPMI (Gibco) containing 10% FBS. All tumor cells were routinely maintained in 5% $CO_2$ and 95% air at 37° C. For assays in hypoxic conditions, cells were cultured in 2% $O_2$, 5% $CO_2$ and 93% $N_2$. ENDOTHELIAL CELLS (ECS): WT and PHD2+/− murine primary endothelial cells were derived from lungs as described (Kuhlencordt et al., Am J Physiol Cell Physiol, 5, 1195-1202, 2004). Briefly, mice were sacrificed by cervical dislocation and lungs were harvested. After a wash in PBS to remove the excess of blood, lungs were minced in RPMI medium containing 0.1% collagenase type I and incubated in the same solution for 1 h at 37° C. with gently agitation. The digested tissue was passed 10 times by a 19 G needle, filtered by a 40 μm pore sized mesh and cells were centrifuged 5 min at 1000 rpm. After red blood cell lysis, the remaining cells were washed in PBS and cultured in DMEMF12 medium (Gibco) containing 20% FBS, endothelial cells growth factors, heparin and antibiotics in 0.1% gelatin pre-coated plates. When reached confluence, cells were incubated with magnetic beads previously coated with anti-ICAM2 (clone 3C4; Pharmingen) and endothelial cells were then selected under magnetic field, using a column (MACS; Miltenyi Biotec). Cell purity was then checked by CD31 or CD105 immunostaining. MOUSE EMBRYONIC FIBROBLASTS (MEFS): WT and PHD2+/− embryos at day 13.5 were dissected to remove all internal organs. The carcass was minced and the pieces incubated with 0.25% trypsin/EDTA and 10 mg/ml DNase for 30 min at 37° C. Cells were cultured in DMEM medium supplemented with 10% FBS. CANCER-ASSOCIATED FIBROBLASTS (CAFS): WT and PHD2+/− CAFs were isolated from GFP+ Panc02 tumors. The tumor was rinsed and disaggregated 1 h in RPMI 10% FBS with 0.1% collagenase I at 37° C. on a rotator. Fibroblasts were sorted by negative selection as CD31−/CD45−/GFPcells and checked by vimentin staining. TUMOR ENDOTHELIAL CELLS (tECS) were sorted from the same samples by selecting CD31+/CD45−/GFP− cells. LEUKOCYTES were obtained by centrifugation of peripheral blood on a Ficoll gradient. TRANSFECTION OF ENDOTHELIAL CELLS WITH RNAI OLIGOMERS: All RNAi oligomers were designed using the Invitrogen online siRNA design tool (worldwideweb.rnaidesigner.invitrogen.com). The following sequences (sense strands) and target positions were used: HIF-1 RNAi (position 933): 5'-CCC ATT CCT CAT CCG TCA A-3'(SEQ ID NO:43 of the SEQUENCE LISTING); HIF-1 RNAi (position 1832): 5'-GCC TAA CAG TCC CAG TGA A-3' (SEQ ID NO:44); HIF-2 RNAi (position 566): 5'-GCU UCC UUC GGA CAC AUA A-3' (SEQ ID NO:45); HIF-2 RNAi (position 1121): 5'-GCC ACA GCA UGG ACA UGA A-3' (SEQ ID NO:46); control RNAi: 5'-GCC CGA GUA CAG UAA CGA A-3' (SEQ ID NO:47). Cells were transfected using Lipofectamine 2000 (Invitrogen) according to the manufacturer's instructions. In brief, one day before transfection, cells were seeded in a 6-well plate in 2 ml of growth medium without antibiotics such that they were 30-50% confluent at the time of transfection. Preparation of the oligonucleotide-Lipofectamine 2000 complexes was done as followed: 100 pmols RNAi oligomers (stock: 20 μM) were diluted in 250 μl Opti-MEM I (Gibco) reduced serum medium. Lipofectamine 2000 (5 μl) was diluted in 250 μl Opti-MEM I reduced serum medium and incubated for 5 min at room temperature. RNAi oligomers in Opti-MEM I medium were gently mixed with Lipofectamine 2000 and allowed to incubate at room temperature for 20 min to form complexes. Just before transfection, the cell culture medium was removed and cells were rinsed twice with serum-free Opti-MEM I medium. The Lipofectamine 2000-RNAi complexes were added to each well in serum-free OptiMEM medium for 6 h. Afterwards, cells were incubated in complete medium for 48-72 h at 37° C. and assayed for gene knockdown (qRT-PCR).

IN VITRO BIOLOGICAL ASSAYS: PROLIFERATION ASSAY: 5 10$^5$ endothelial cells were seeded in gelatin-coated 24-well plate. After 36 h of starvation in serum-free medium, semiconfluent cell layers were stimulated with 50 ng/ml VEGF (R&D). After 24 h, cells were challenged with 10 M BrdU for 30 min at 37° C. Cells were fixed with 4% PFA and 70% ethanol, then stained with FITC-conjugated anti-BrdU according to the manufacturer's instructions (BD Bioscience). APOPTOSIS ASSAY: semiconfluent endothelial cell layers were stimulated in serum-free medium with 50 ng/ml VEGF. After 72 h cells were fixed in 4% PFA. TUNEL staining was performed according to manufacturer's instructions (In situ cell death detection kit, Roche). MOTILITY ASSAY: semiconfluent endothelial cell layers were seeded on a fibronectin-coated 35 mm tissue culture dish and starved for 48 h with 0.5% FBS medium. After scratching the monolayer with a pipette tip, vehicle or VEGF (50 ng/ml) was added in the same growth medium. Images were acquired for 6-14 h taking an image every 15 min. LAMELLIPODIA AND FILOPODIA FORMATION ASSAY: sparse primary endothelial cells were starved for 48 h in 0.5% FBS medium and stimulated with 50 ng/ml VEGF or FGF-2 (R&D) for the times indicated. After fixation, cells were stained with Alexa 488-conjugated phalloidin. Quantification of lamellipodia and filopodia was performed as described (Kitamura et al., Nat Cell Biol, 3, 329-337, 2008; Sheldon et al., FASEB J, 2008). TRANS-ENDOTHELIAL ELECTRICAL RESISTANCE (TER) ASSAY: Transwell unit (Costar) were coated with gelatin crosslinked with glutaraldehyde. 50,000 ECs were seeded in the inserts (upper chamber, pore size 0.4 mm) and allowed to reach full confluence in complete medium for 96 hours before measurement. TER was measured using a Multicell-ERS voltohmmeter (Millipore).

ELISA: Concentrations of sFlt1 and VEGF-A were quantified in endothelial cells medium supernatants and in serum of tumor-free and tumor-bearing mice using sFlt1 and VEGF immunoassays (R&D Systems).

IMMUNOPRECIPITATION AND WESTERN BLOT ANALYSIS: Protein extraction and Western blot analysis were performed using 1% Triton buffer or 8M urea buffer as described (Michieli et al., Cancer Cell, 6, 61-73, 2004; Sowter et al., Cancer Res, 63, 6130-6134, 2003). Nuclear extraction was performed in cell extracts using a Nuclear and Cytoplasmic Extraction kit (Pierce Biotechnology), according to manufacturer's instructions. Signal was detected using ECL system (Amersham Biosciences, Uppsala, Sweden) according to the manufacturer's instructions. The following antibodies were used: rabbit anti-HIF-2, rabbit anti-PHD1, rabbit anti-PHD2 (generated by P. Ratcliffe and P. Maxwell), rabbit anti-HIF-1, rabbit anti-PHD3 (Novus), goat anti-VE-cadherin (R&D Systems), rabbit anti-Flt1 (R&D Systems for the IP and Sigma for the WB), and anti-β-tubulin or actin (Abcam).

QRT-PCR: Quantitative RT-PCR was performed as described (Fischer et al., Cell, 131, 463-475, 2007), using commercially available or home-made primers and probes for the studied genes. The Assay ID (provided by Applied Biosystems) or the sequence of primers and probes (when home-made) are listed in Table S2.

HYPDXIA ASSESSMENT AND TUMOR PERFUSION: Tumor hypoxia was detected 2 h after injection of 60 mg/kg pimonidazole hydrochloride (PIMO) into tumor bearing mice. After 2 h, mice were sacrificed and tumors harvested. To detect the formation of pimonidazole adducts, tumor cryosections were immunostained with Hypoxyprobe-1-Mab1 (Hypoxyprobe kit, Chemicon) following the manufacturer's instructions. Tumor perfusion was analyzed using fluorescent microspheres as described (Luttun et al., Nat Med, 8, 831-840, 2002). Perfused tumor vessels were also counted on tumor cryosections by following intravenous injection of 0.05 mg FITC-labelled lectin (*Lycopersicon esculentum*; Vector Laboratories, Burlingame, Calif.) in tumor-bearing mice. Vessel leakage was analyzed after intravenous injection of 0.25 mg Texas Red-conjugated Dextran 70 kD (Molecular Probes). Ten minutes later, mice were perfused by intracardiac injection of saline (5 min) and 2% PFA (7 min). Tumors were then harvested and frozen in OCT medium. Alternatively, 100 l of a 3% Evans blue solution were injected into the tail vein and after 10 min mice were perfused, the organs collected in formamide and digested for 24 h at 70° C. Concentration of the dye was determined spectrophotometrically at 630 nm.

OXYMETRY, LACTATE AND REDOX POTENTIAL: We measured tumor oxygen tension (pO2) using charcoal powder (100 mg; CX0670-1; EM Science) as the oxygen-sensitive probe. Calibration curves were made by measuring the EPR line width as a function of the pO2 (Aragones et al., Nat Genet, 2, 170-180, 2008). Charcoals were injected into 100 mm3 tumors and oxygen tension was measured after 48 h by using an EPR spectrometer (Magnetech) with a low-frequency microwave bridge operating at 1.1 GHz and extended loop resonator. The intratumoral levels of lactate were measured as described on snap frozen tissues, harvested from WT and PHD2+/− mice when the tumors were between 200 and 400 mm3 (Noll, Methods Enzymatic Analysis, 6, 582-588, 1981). NADH and NAD+ were quantified independently on a snap-frozen tumor sample as described (Pospisilik et al., Cell, 131, 476-491, 2007).

METASTATIC INCIDENCE SCORING: contrast staining of metastases with India ink was done as described before (Mazzone et al., 2004).

STATISTICS: Data represent mean±SEM of representative experiments unless otherwise stated. Statistical significance was calculated by t-test or 2-way ANOVA where indicated (Prism v4.0b), considering $P<0.05$ as statistically significant.

Example 1

Generation of PHD2+/− Mice and Expression of PHD2

Figure 8:
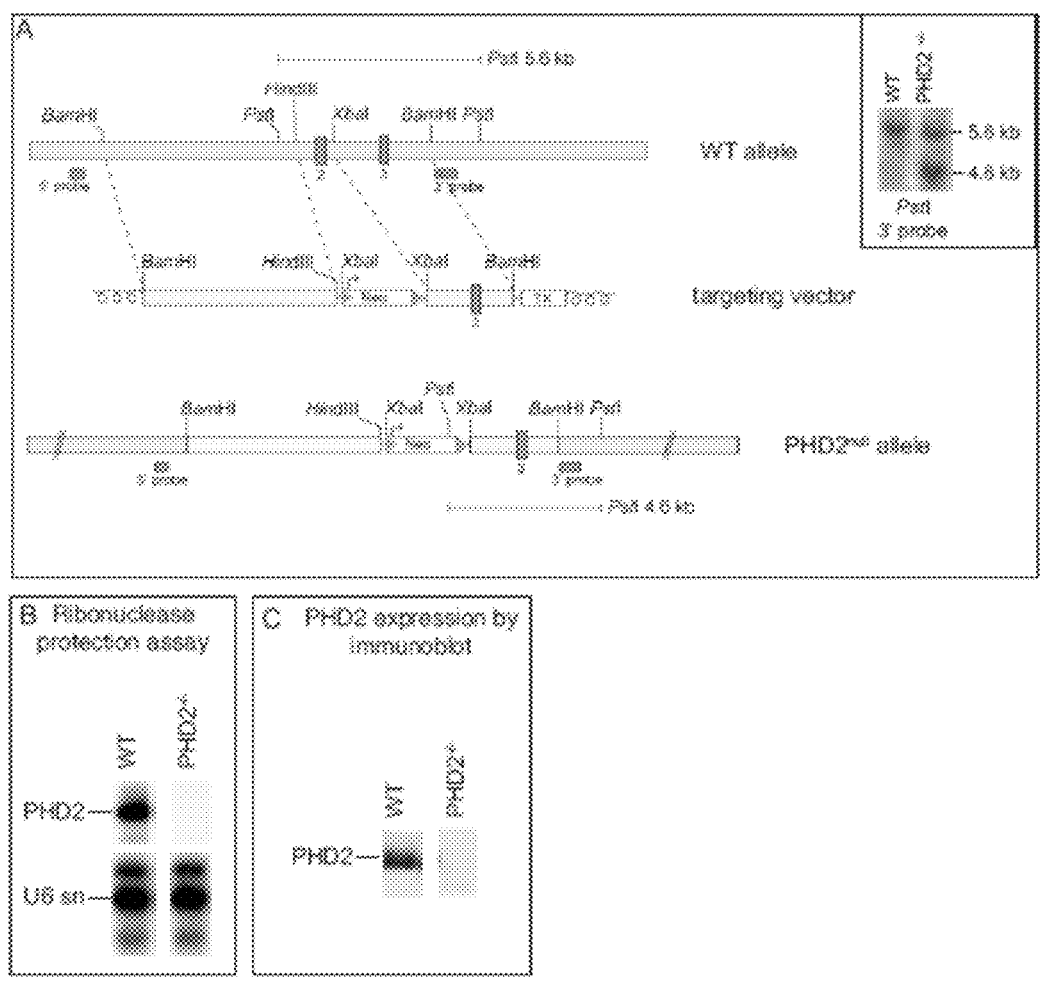
FIG. 8: GENERATION OF MICE LACKING PHD2 AND ANALYSIS OF PHD2 EXPRESSION. A, Targeting strategy for inactivation of the PHD2 locus. Top: Wild type PHD2 allele, with relative positions of exons 2 and 3 (dark boxes in genomic structure). Middle: Outline of the targeting vector specifying the genomic sequences used as 5' and 3' homology flanks, cloned at both sides of a neomycin resistance (Neo) cassette. A thymidine kinase (TK) gene outside the flanking homologies was used for negative selection against random integration events. Bottom: Replacement of exon 2 by the Neo cassette after homologous recombination. A diagnostic restriction fragment generated with PstI is indicated by a thin line under the allele. Inset: Southern Blot analysis of genomic DNA from WT and PHD2+/− ES cells, digested with PstI and hybridized with 3' external probe. The 5.6 kb and 4.6 kb fragments correspond to the WT and null PHD2 allele, respectively. B, Ribonuclease protection assay, confirming the absence of PHD2 mRNA transcripts in PHD2−/− embryos. C, Immunoblot revealing detectable PHD2 protein in WT but not in PHD2−/− embryos.
Figure 9:
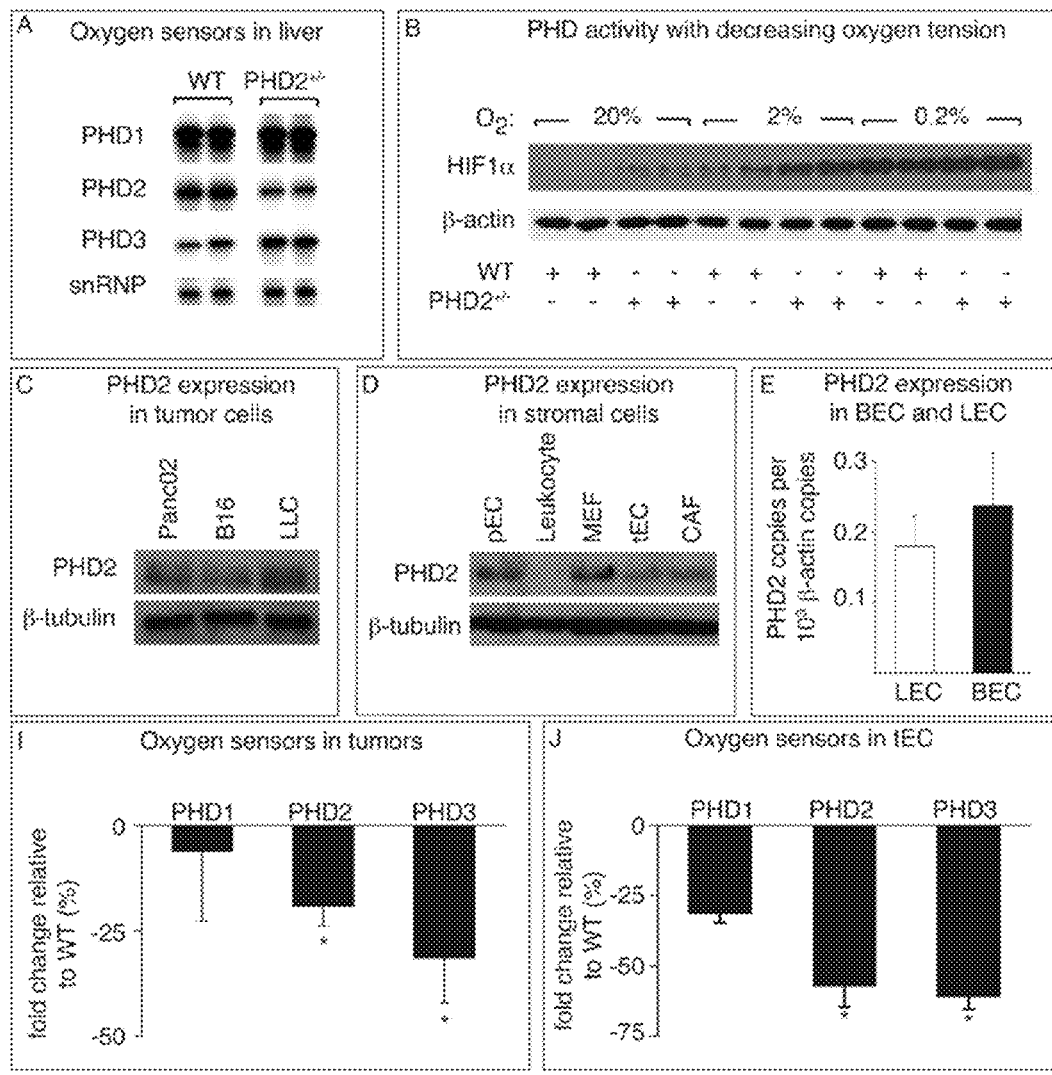
FIG. 9: EXPRESSION OF PHDS IN NORMAL TISSUES, TUMOR AND STROMAL CELLS. A, Immunoblot for PHDs in WT and PHD2+/− livers, revealing ☐50% of PHD2 levels and a slight upregulation of PHD3 levels in PHD2+/− livers. B, Immunoblot for HIF-1α in mouse embryonic fibroblasts (MEF) exposed to various oxygen tensions, revealing an upregulation of HIF-1α levels in hypoxic conditions; HIF-1α levels were higher in PHD2+/− cells at every oxygen tension, indicating that PHD2 is still active at low oxygen tensions. C,D, Immunoblot for PHD2 in Panc02, B16 and LLC tumor cells (C), endothelial cells (pEC, pulmonary endothelial cells; tEC, tumor endothelial cells), fibroblasts (mouse embryonic fibroblasts, MEF or cancer associated fibroblasts, CAF) and circulating leukocytes (D). E, RT-PCR analysis, revealing expression of PHD2 in cultured primary lymphatic endothelial cells (LEC), comparably to blood endothelial cells (BEC). F,G, RT-PCR analysis, indicating that PHD2 and PHD3 transcript levels in pancreatic tumors (I) and tumor endothelial cells freshly isolated from pancreatic tumors without any subculturing (tECs) (J) are reduced in PHD2+/− mice; bars represent the downregulation of the indicated genes, as % of the levels in WT mice. Asterisks in panels F,G denote statistical significance (P<0.05). Error bars in E,F,G show the standard error of the mean (SEM); all subsequent error bars are defined similarly.

To study its biological role in vivo, we inactivated the PHD2 gene in the germline (FIG. 8A). PHD2 deficient (PHD2−/−) mice died at mid-gestation, while PHD2+/− mice developed normally, were healthy, and did not exhibit vascular defects (Table S1, immunostaining data not shown); physiological angiogenesis was also normal (immunostaining data not shown). PHD2 mRNA and protein were undetectable in PHD2−/− embryos (FIG. 8B,C) and present at 50% of the normal levels in healthy organs in PHD2+/− mice, with minimal upregulation of PHD3 (FIG. 9A). Also, cultured PHD2+/− cells expressed 50% of the normal PHD2 levels at various oxygen tensions (FIG. 1A). Consistent with previous findings that PHDs are HIF-targets and upregulated in chronic hypoxia (Appelhoff et al., 2004; Epstein et al., 2001; Marxsen et al., 2004, Aragones et al., 2008), PHD3 and to a lesser extent PHD1 protein levels were upregulated in PHD2+/− cells, especially in normoxic conditions (FIG. 1A). As expected, PHDs were also upregulated in WT cells in hypoxia conditions (FIG. 1A). PHD2 becomes gradually less active in hypoxia, but still retains activity at low oxygen tensions (Epstein et al., 2001). HIF-1α levels were indeed higher in PHD2+/− cells at every, even low, oxygen tension (FIGS. 1B & 9B); HIF-2α levels were also upregulated, particularly in endothelial cells (ECs) (FIG. 1B). By resetting their oxygen sensing curve, PHD2+/− cells act as if they continuously sense lower oxygen tensions, as if they are (pre)-adapted to hypoxia.

To study selectively the role of stromal PHD2 in tumor biology without confounding effects of a role of PHD2 in malignant cells, we used chimeric tumor models, generated by implanting, in PHD2+/− mice, various types of PHD2+/+ tumor cells (B16F10.9 melanoma, Panc02 pancreatic carcinoma and LLC Lewis lung carcinoma cells). We first analyzed which tumor and stromal cell types expressed PHD2. In vitro, PHD2 was detectable in all tumor lines, blood and lymphatic ECs, and fibroblasts (FIG. 9C-E). In vivo, tumor, endothelial and fibroblast cells were PHD2 positive (not shown). In PHD2+/− mice, transcript levels of PHD2 and -3 were reduced in tumors and ECs, freshly isolated from tumors and immediately analyzed without subculturing (FIG. 9F,G; see below for interpretation).

Example 2

Normal Tumor Growth but Reduced Metastasis in PHD2+/− Mice

Figure 10:
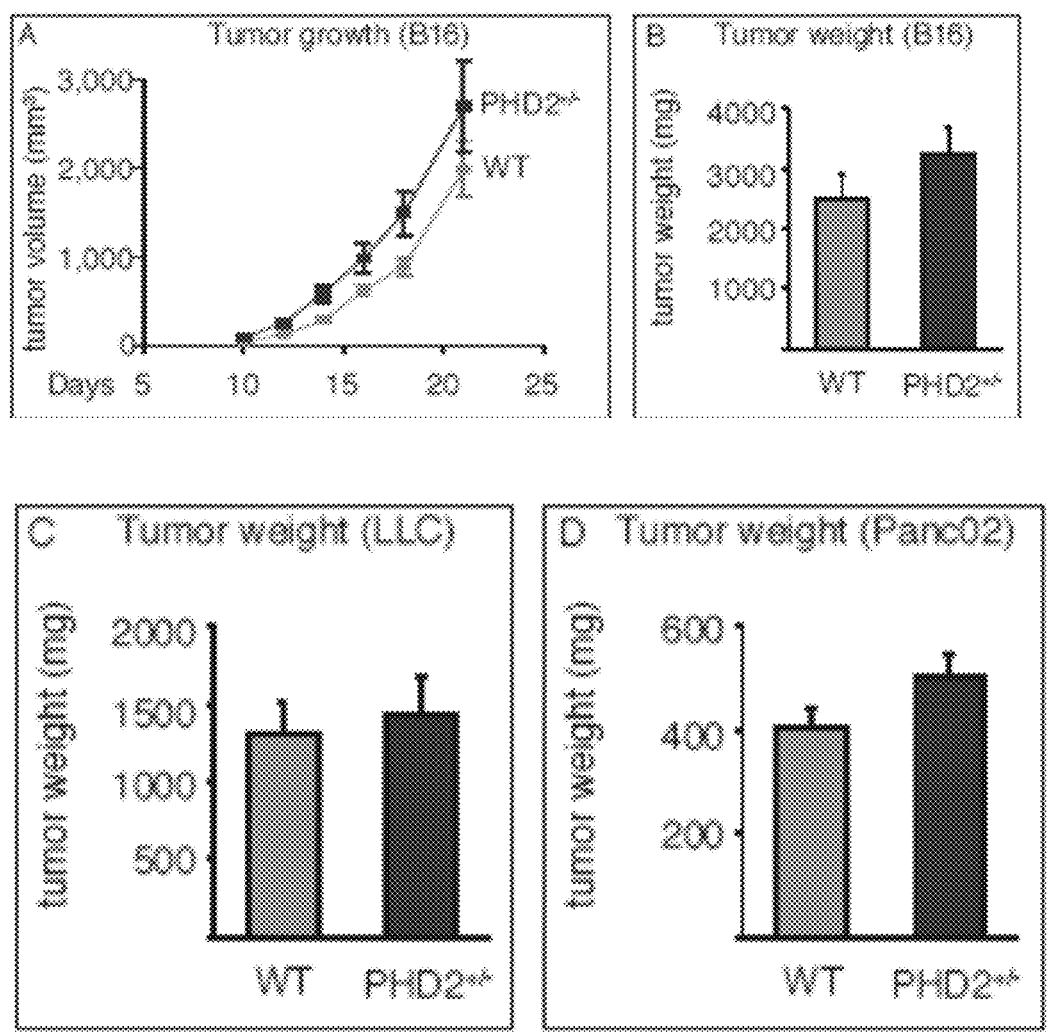
FIG. 10: NORMAL TUMOR GROWTH IN PHD2+/− MICE. A, WT and PHD2+/− mice exhibit comparable tumor growth rates after implanting B16 melanoma tumors subcutaneously (N=15; P=0.08). B-D, Tumor weight in PHD2+/− mice is also comparable for B16 tumors (N=15; P=0.28) (B), LLC tumors (N=8; P=0.33) (C) and pancreatic Panc02 tumors (N=27; P=0.12) (D).

To explore the role of stromal PHD2 in cancer, we injected various tumor cell types in WT and PHD2+/− mice. Ectopically implanted B16 and LLC tumors, or orthotopically implanted Panc02 tumors grew at a comparable rate in both genotypes (FIGS. 1C and 10), and displayed comparable tumor cell proliferation and apoptosis rates (not shown). Tumors in PHD2+/− mice appeared macroscopically less "bloody" (FIG. 1D,E). Considering that HIFs promote metastasis (Semenza, 2003; Sullivan and Graham, 2007), we expected that tumors in PHD2+/− mice would metastasize aggressively. However, tumors in PHD2+/− mice were less invasive and metastatic. Indeed, in PHD2+/− mice, B16 tumors were well encapsulated, grew focally and did not infiltrate in the surrounding tissue (FIG. 1F,G) and metastasized less to the lungs (% of lung sections containing micrometastases: 22.9±2.8% in WT mice versus 7.3±3.7% in PHD2+/− mice; N=6; P=0.01). Also, LLC tumors grew non-invasively (not shown), while the number of metastatic nodules on the lung surface was reduced by 94% in PHD2+/− mice (FIGS. 1H-J & 11A-D). Likewise, Panc02 tumors in PHD2+/− mice grew as well encapsulated local tumors in the pancreas, and could easily be dissected from adjacent organs, while tumors in WT mice invaded in the stomach and duodenum (FIG. 1D,E). Histologically, 50% of the WT but none of the PHD2+/− mice had tumors with infiltrative margins (not shown). Also, hepatic metastasis was reduced in PHD2+/− mice: 75% of WT mice, but only 38% of PHD2+/− mice exhibited hepatic nodules, with 3.5±0.8 nodules/mouse in WT mice, but only 0.7±0.3 nodules/mouse in PHD2+/− mice (N=6; P=0.01; FIG. 1D, E). Furthermore, out of 8 mice per group, 6 WT mice but only 2 PHD2+/− mice displayed gallbladder enlargement and jaundice (FIG. 1D, E). Moreover, the number of metastatic mesenteric lymph nodes was reduced by 60% in PHD2+/− mice (FIG. 1K-M). Thus, when stromal cells expressed only a single PHD2 allele, tumors consistently grew less invasively, and metastasized substantially less. For subsequent studies, we generally used the orthotopic Panc02 model, as this tumor grows and metastasizes most aggressively, unless stated otherwise.

Figure 11:
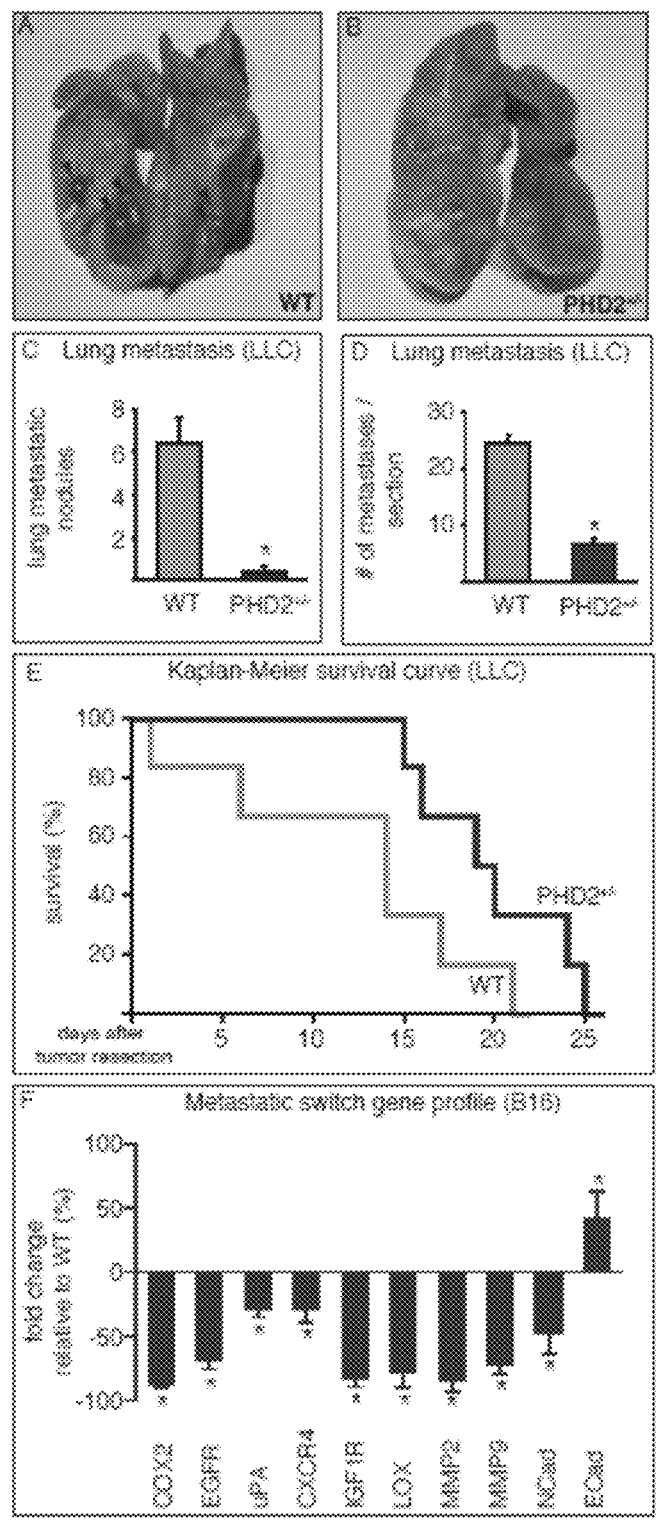
FIG. 11: REDUCED METASTASIS IN PHD2+/− MICE. A,B, Macroscopic view of the lungs, revealing reduced pulmonary metastasis of LLC tumors in PHD2+/− mice (arrowheads denote metastatic nodules). C,D, Quantification of the number of pulmonary LLC tumor nodules revealed reduced lung metastasis in PHD2+/− mice upon macroscopic inspection of the lungs (N=8; P<0.0001) (C), or upon histological analysis of H&E stained sections (N=8; P<0.0001) (D). E, Survival curve showing a significant survival benefit of PHD2+/− mice; Breslow test (N=6, P=0.04). X-axis indicates days after LLC size-matched tumor resection. F, RT-PCR analysis, revealing downregulation of pro-metastatic genes and upregulation of the anti-metastatic E-cadherin gene in B16 tumors in PHD2+/− mice; bars represent the upregulation or downregulation of the expression of the indicated genes, expressed as % of the levels in WT mice (N=5-12; P<0.05). Asterisks in panels C,D,E,F denote statistical significance.

Since metastasis is the primary cause of death in cancer patients, a reduction in metastasis (as observed in PHD2+/− mice) should provide a significant survival benefit. To investigate this, we implanted LLC tumors subcutaneously in the footpad and removed the primary tumor when reaching a volume of 800 mm$^3$ to allow further growth of metastatic nodules; in this model, survival is correlated with pulmonary metastasis (Gao et al., 2008). Consistent with our previous analysis that tumors metastasize less in PHD2+/− mice, survival of these mice is substantially prolonged (mean survival time, days after tumor surgery: 14 days in WT versus 19.5 days in PHD2+/− mice, N=6, P=0.04; FIG. 11E). Haplodeficiency of PHD2 thus offers a survival benefit. As is illustrated in a further example, PHD2+/− mice also exhibit a greater response to chemotherapy.

Stromal Haplodeficiency of PHD2 Impedes Intravasation of Tumor Cells

Figure 2:
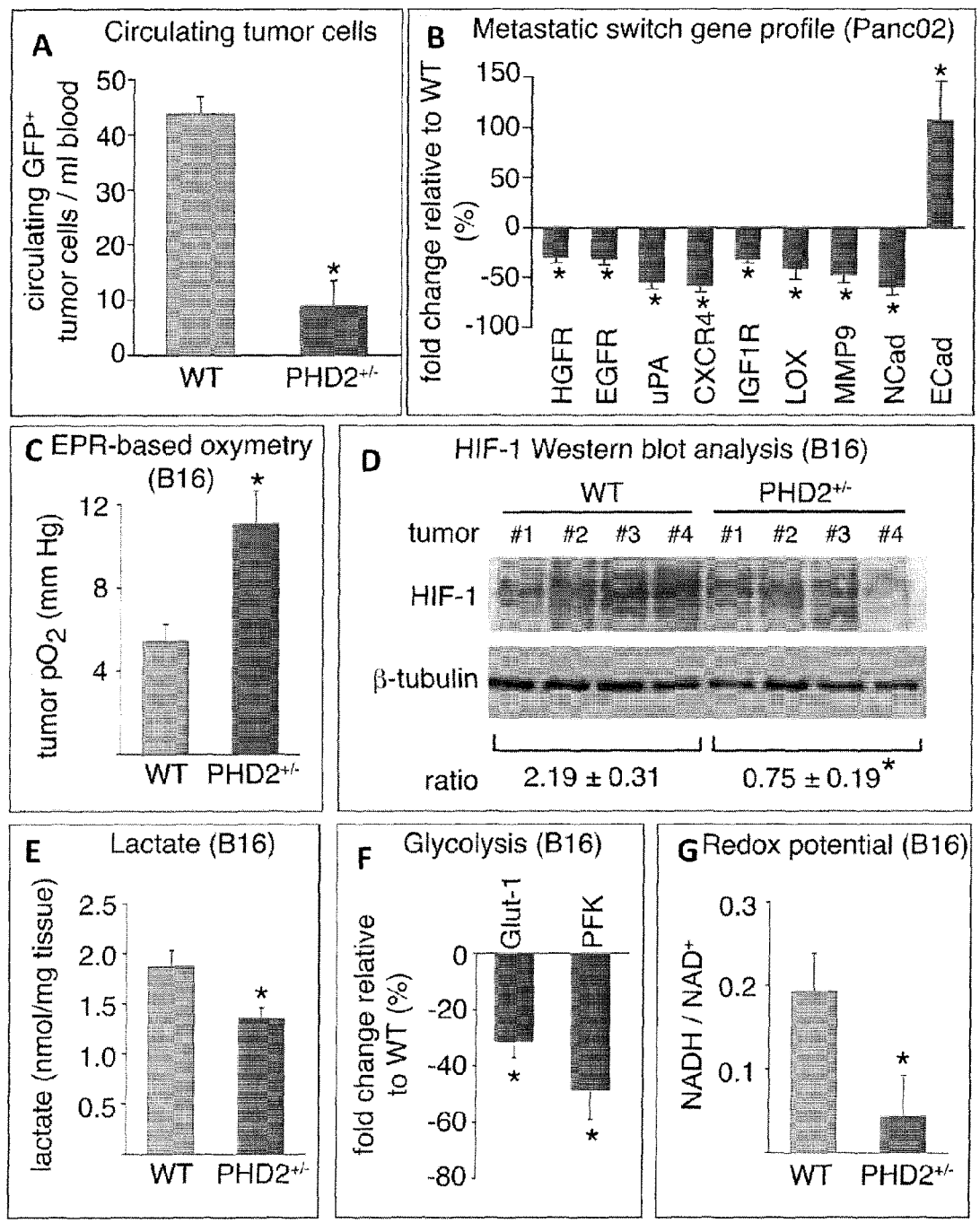
FIG. 2: TUMOR INTRAVASATION AND OXYGENATION IN PHD2+/− MICE. A, Reduced circulating GFP+ tumor cells in PHD2+/− mice (N=5; P=0.0005). B, RT-PCR, revealing downregulation of pro-metastatic genes and upregulation of the antimetastatic E-cadherin in Panc02 tumors in PHD2+/− mice (% of WT levels; N=5-12; P<0.05). C, EPR oxymetry, revealing increased tumor oxygenation in PHD2+/− mice (N=10; P=0.003). D, Immunoblot for HIF-1α and β-tubulin, revealing reduced [HIF-1α/β-tubulin] ratio in tumors in PHD2+/− mice (N=4; P=0.007). E-G, Reduced Warburg effect in B16 tumors in PHD2+/− mice, shown by reduced lactate content (N=6; P=0.04) (E), transcripts of GLUT-1 and PFK (% of WT levels; N=5; P<0.05) (F), and [NADH/NAD+] ratio (N=4; P<0.05) (G). Asterisks in A-G denote statistical significance.

To characterize the role of stromal PHD2 in metastasis, we analyzed tumor cell intravasation, a critical step in tumor cell colonization to distant organs. Staining of Panc02 tumor sections for the endothelial marker CD31 and the epithelial marker pancytokeratin revealed that the number of tumor vessels with intravasated cancer cells was reduced by 50% in PHD2+/− mice (% of vessels with intravasated tumor cells: 47.8±5.0% in WT versus 23.9±0.8% in PHD2+/−; N=6; P<0.001; data on tumor sections available but not shown). Implantation of Panc02 cells, transduced with a GFP-expressing lentiviral vector, confirmed these findings (not shown). To count the circulating tumor cells that escaped the tumor, we collected blood from GFP+ Panc02 tumor-bearing mice after twelve days. PHD2 haplodeficiency reduced the number of circulating GFP+ tumor cells by 79% (FIG. 2A). Instead, intravenous injection of GFP+B16 tumor cells did not result in genotypic differences in the number of hepatic or pulmonary colonies, indicating that tumor cell lodging and extravasation in distant organs were normal (not shown). Thus, stromal haplodeficiency of PHD2 inhibits metastasis, in part by preventing tumor cell intravasation.

Reduced Metastatic Switch in Tumors in PHD2+/− Mice

We then analyzed the molecular mechanisms underlying the reduced metastatic switch in PHD2+/− mice. Gene profiling revealed that pancreatic and melanoma tumors in PHD2+/− mice expressed reduced transcript levels of pro-metastatic genes, that either promote survival, epithelial-mesenchymal transition (EMT) or motility of tumor cells, stimulate extracellular matrix degradation, or reduce cohesion between tumor-tumor or tumor-stromal cells (Sullivan and Graham, 2007). As shown in FIG. 2B and FIG. 11F, tumors in PHD2+/− mice expressed lower levels of cyclooxygenase-2 (COX2), epidermal growth factor receptor (EGFR), hepatocyte growth factor receptor (HGFR), CXC chemokine receptor-4 (CXCR4), matrix metalloproteinase-2 (MMP2), MMP9, urokinasetype plasminogen activator (uPA), insulin-like growth factor-1 receptor (IGF1R), lysyl oxidase (LOX) and N-cadherin, while expression of E-cadherin, which promotes tumortumor cell adhesion and correlates with a positive clinical outcome in cancer patients (Sullivan and Graham, 2007), was increased. Interestingly, expression of these genes is regulated by hypoxia through HIFs (Erler et al., 2006; Pennacchietti et al., 2003; Semenza, 2003; Sullivan and Graham, 2007).

Example 3

Improved Tumor Oxygenation in PHD2+/− Mice

Since hypoxia promotes tumor cell invasion and metastasis, in part by upregulating the metastatic genes listed above, we analyzed tumor oxygenation. Staining for the hypoxia-marker pimonidazole revealed a reduced hypoxic tumor area in PHD2+/− mice (% of total tumor area was 20.9±7.4% in WT mice versus 7.4±3.5% in PHD2+/− mice for B16 tumors (N=6; P=0.01; not shown), and 15.7±2.2% in WT mice versus 7.2±1.0% in PHD2+/− mice for Panc02 tumors (N=4; P=0.01)). Electron paramagnetic resonance-based oximetry indicated that the oxygen pressure in B16 tumors was two-fold higher in PHD2+/− mice (FIG. 2C). Protein levels of HIF-1, an indirect measure of hypoxia, were three-fold lower in B16 tumors in PHD2+/− mice (FIG. 2D); levels of the HIF-target VEGF were also reduced (μg/10 mg tumor tissue: 4±0.5 in WT versus 2.7±0.2 in PHD2+/−; N=6; P<0.05). Also, the necrotic area, % of total tumor area, was 35±9% in WT mice versus only 16±4% in PHD2+/− mice for B16 tumors (N=6, P=0.006; not shown); the necrotic area was also three-fold smaller in Panc02 tumors in PHD2+/− mice (N=6, P=0.03). Consistent with the notion that PHD3 transcription is strongly induced by hypoxia (Appelhoff et al., 2004; Epstein et al., 2001), its mRNA levels were downregulated in tumors and in tumor endothelial cells, freshly isolated from tumors and directly used for analysis, in PHD2+/− mice (FIG. 9F, G). While the reduced tumor PHD2 levels in PHD2+/− mice are in part attributable to the reduced expression of PHD2 in tumor stromal cells, a similar downregulation of PHD2 expression by oxygen (Appelhoff et al., 2004; Epstein et al., 2001) in tumor cells may also contribute (FIG. 9F). Overall, tumors are better oxygenated in PHD2+/− than WT mice. The observation that PHD2 was downregulated slightly more than the expected 50% (based on the genetic deletion of a single allele; FIG. 9G) may result from a downregulation of PHD2 gene transcription by the better oxygenation of tumor vessels in PHD2+/− than WT mice, since transcription of PHD2 is regulated by oxygen levels. Any oxygen-dependent downregulation of PHD2 might install a positive feedback loop, which would only further amplify tumor vessel normalization, oxygenation, PHD2 downregulation, and so on.

Example 4

Reduced Glycolysis (Warburg Effect) in Tumors Grown in PHD2+/− Mice

Tumor cells generate ATP largely via glycolysis (Warburg effect), allowing them to biosynthesize sufficient macromolecules for rapid growth (Gatenby and Gillies, 2004). The acidic microenvironment, resulting from the formation of glycolytic lactate, promotes tumor invasion and malignancy (Gatenby and Gillies, 2004). Since glycolysis is enhanced in hypoxic conditions, lactate levels are not only a measure of tumor metabolism (and malignancy), but also indirectly of tumor oxygenation. Compared to WT mice, B16 tumors in PHD2+/− mice had lower contents of lactate (FIG. 2E), and expressed lower levels of the HIF-1α targets GLUT-1 (glucose transporter) and PFK (phosphofructose kinase), key molecules controlling glycolytic flux (FIG. 2F). This suggests that tumors in PHD2+/− mice were less glycolytic, because of their improved oxygenation. Similar results were obtained for Panc02 tumors (not shown).

Consistent with a reduced Warburg effect, tumors in PHD2+/− mice expressed lower levels of PDK4 (pyruvate dehydrogenase kinase), which restricts entry of glycolytic intermediates into the tricarboxylic acid cycle (mRNA copies/$10^3$ mRNA copies β-actin: 1.60±0.43 in WT versus 0.45±0.14 in PHD2+/−; N=6-10; P=0.03); similar findings were obtained for PDK1 (not shown). Moreover, analysis of NAD+ levels and the [NADH/NAD+] ratio, measures of the cellular redox status, revealed that tumors in PHD2+/− mice shifted away from glycolytic to more oxidative metabolism (μg NAD+/g tumor: 5.3±2.0 in WT versus 13.6±2.1 in PHD2+/−; N=4; P<0.05; FIG. 2G). Overall, tumors in PHD2+/− mice were better oxygenated and, likely therefore, reprogrammed their metabolism to more aerobic generation of ATP, as typically occurs in more benign tumors (Gatenby and Gillies, 2004).

Example 5

PHD2 Haplodeficiency Improves Vessel Function and Maturation

Figure 12:
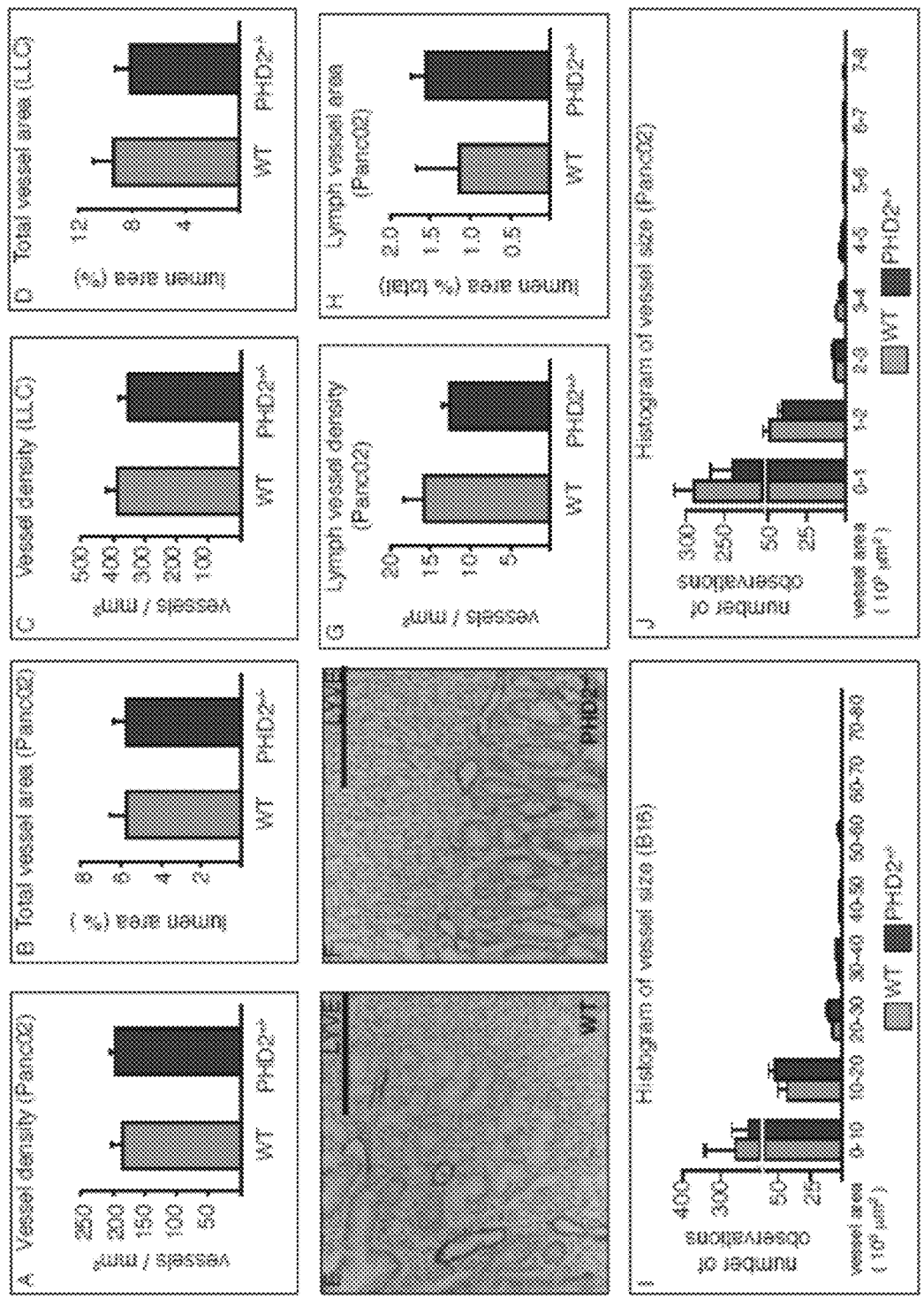
FIG. 12: TUMOR VESSEL DENSITY, AREA AND DISTRIBUTION IN PHD2+/− MICE. A-D, Morphometric quantification of vessels after CD31 immunostaining in Panc02 (A,B) and LLC (C,D) tumors, revealing comparable vessel density (A,C) and total vessel area (B,D) in tumors in WT and PHD2+/− mice (N=6-8; P=NS). E,F, Immunostaining for the lymphatic marker LYVE-1, revealing comparable lymphatic density in pancreatic tumors in WT (E) and PHD2+/− (F) mice. G,H, Morphometric quantification of LYVE-1 stained vessels indicates comparable lymphatic density (G) and lymphatic area (H) in both genotypes. I,J, Histogram, revealing a comparable distribution of the number of vessels according to their lumen size in B16 (I) and Panc02 tumors (J) in WT or PHD2+/− mice. Bar: 100 μm in panels E,F.

We then investigated how stromal haplodeficiency of PHD2 improved tumor oxygenation. Hypoxia in tumors may result from an insufficient number of vessels or, alternatively, from an excessive number of non-perfused vessels (Franco et al., 2006; Noguera-Troise et al., 2006). Tumor "vessel abnormalization", characterized by tortuous, leaky vessels of inhomogeneous size and shape, also impairs perfusion (Jain, 2005). We therefore analyzed various aspects of the tumor microvasculature. We had expected that reduced PHD2 levels, possibly via upregulation of HIFs, would stimulate vessel sprouting and/or branching. However, CD31 staining revealed that tumor vessel density, as well as total and average tumor vessel area, were comparable in both genotypes, in all tumor models tested (FIG. 3A,B; FIG. 12A-D). Similar results were obtained when analyzing tumor lymphatics (FIG. 12E-H). Also, the distribution of tumor vessels according to their size was overlapping in both genotypes, indicating that there was no shift from small to large vessels (or vice versa) (FIG. 12I,J). However, tumor vessels appeared more fragile in WT mice, as blood extravasated in many tumor regions in WT but not in PHD2+/− mice (not shown), explaining why tumors in WT mice appeared more reddish (FIG. 1D,E).

Improved Tumor Vessel Function in PHD2+/− Mice

Figure 3:
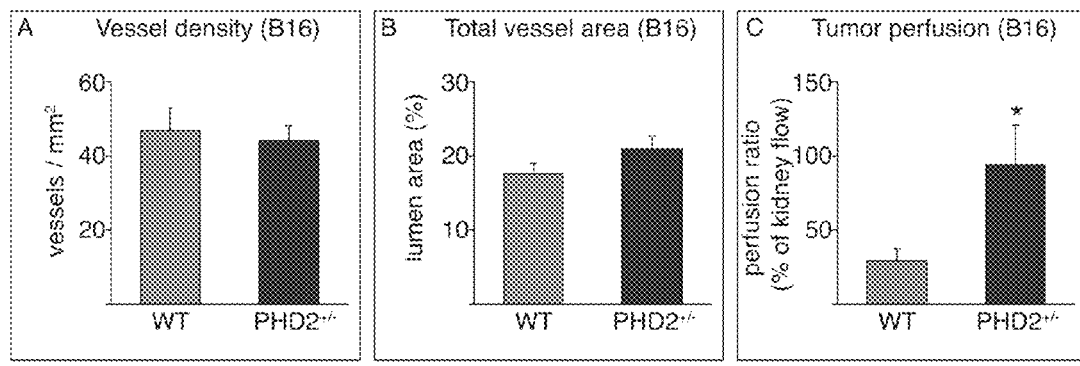
FIG. 3: IMPROVED VESSEL FUNCTION AND MATURATION IN PHD2+/− MICE. A,B, Tumor vessel density (A) and vessel area (B) (N=6; P=NS). C, Improved tumor perfusion in PHD2+/− mice (% of renal perfusion; N=10; P=0.02). Asterisk in C denotes statistical significance.
Figure 13:
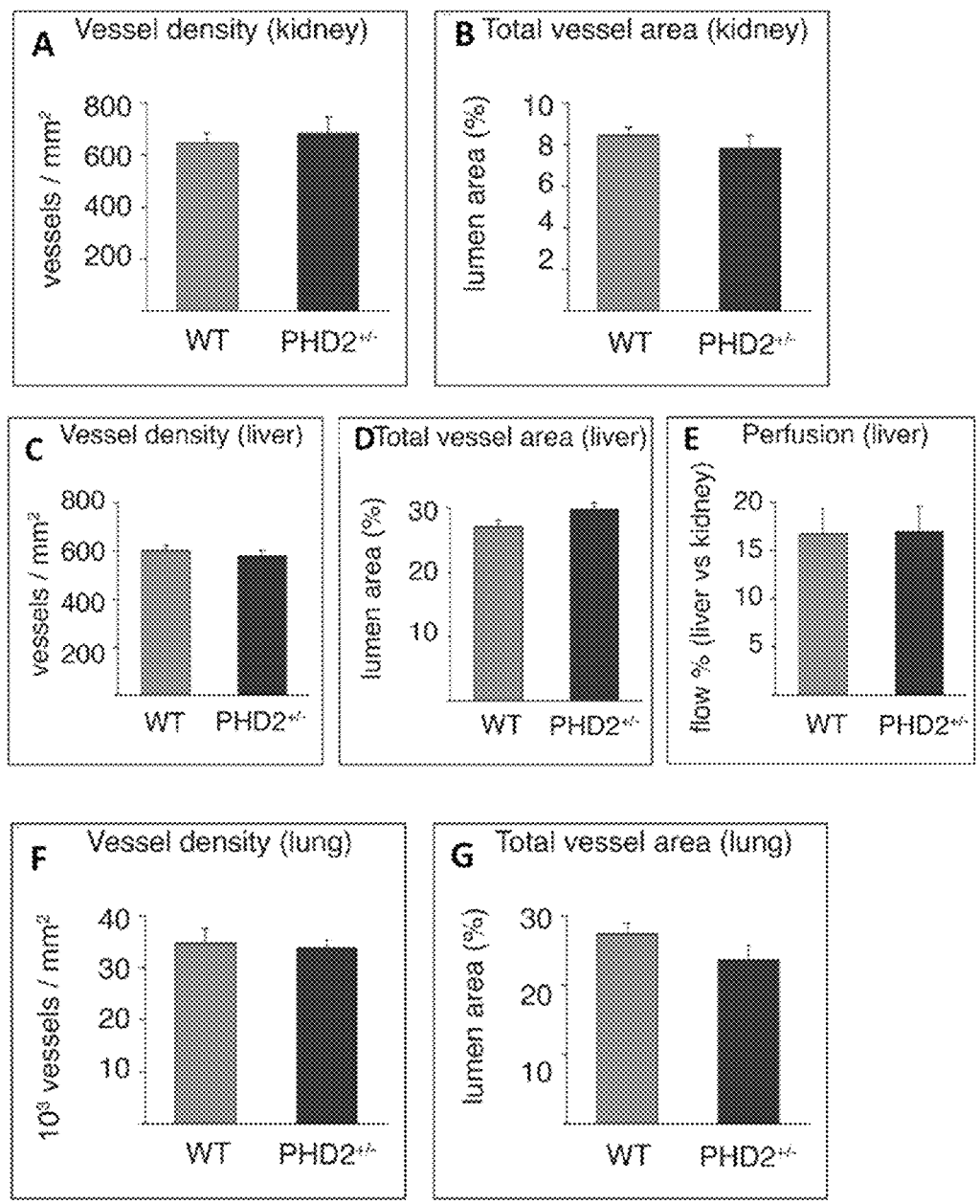
FIG. 13: VESSEL PHENOTYPE OF HEALTHY ORGANS IN PHD2+/− MICE. A-D,F,G, Quantification of vessel parameters revealed comparable vessel density and total vessel area in the kidney (A,B), liver (C,D) and lung (F,G) in WT and PHD2+/− mice (N=4; P=NS). E, Liver perfusion, analyzed by the injection of fluorescent microspheres, is comparable in both genotypes.

The fact that PHD2 haploinsufficiency did not change tumor vessel density, yet reduced hypoxia, prompted us to analyze whether an improvement in vessel function might explain the increased tumor oxygenation in PHD2+/− mice. Use of fluorescent microspheres revealed that perfusion of melanomas was three-fold higher in PHD2+/− mice (FIG. 3C). Microscopic analysis confirmed that the number of perfused tumor vessels was increased in PHD2+/− mice (lectin+ vessels per optical field: 5.17±0.55 in WT versus 7.92±0.08 in PHD2+/−; N=4; P=0.003). This genotypic difference was specific for tumor vessels, as healthy tissues such as kidneys, lungs and liver displayed comparable vessel area, vessel density and perfusion in both genotypes (FIG. 13).

Figure 14:
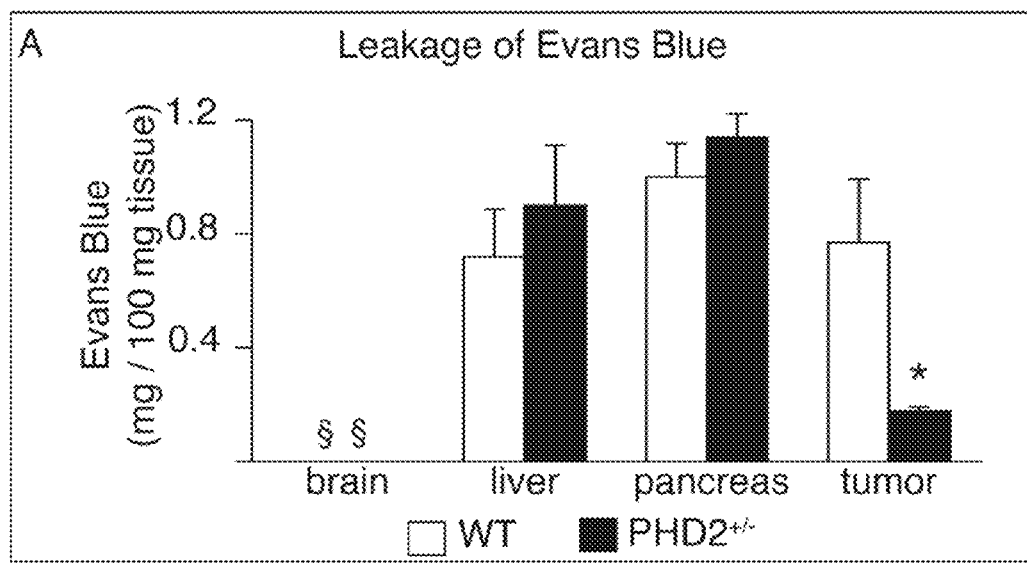
FIG. 14: VESSEL PERMEABILITY IN PHD2+/− MICE. Quantification of the amount of extravasated Evans blue, revealing that permeability is high in hepatic and pancreatic vessels and minimal in brain vessels, but comparable in WT and PHD2+/− mice. By contrast, leakiness of tumor vessels was significantly reduced in PHD2+/− mice (N=5; P=0.03). § denotes below detection limit. Asterisk denotes statistical significance.

We also analyzed the permeability of the endothelial barrier, which co-determines tumor perfusion (Jain, 2005). Indeed, when tumor vessels are abnormally leaky, extravasation of plasma increases the interstitial tumor pressure, which in turn induces tumor vessel collapse and impedes perfusion (Boucher and Jain, 1992). Upon intravenous injection of Texas Red-conjugated dextran and FITC-conjugated lectin, extravasation of dextran was reduced in B16 tumors in PHD2+/− mice (leaky vessels, % of total: 69.7±11.3% in WT versus 22.4±8.9% in PHD2+/−; N=4; P=0.02; not shown). Similar findings were obtained when injecting Evans Blue (FIG. 14) or measuring transendothelial electrical resistance in vitro (not shown). Leakage of Evans Blue in healthy vessels was normal in PHD2+/− mice (FIG. 14 and data not shown). A tighter endothelial barrier may also contribute to and thus explain the reduced intravasation of tumor cells and intratumoral bleeding in PHD2+/− mice.

Enhanced Tumor Vessel Maturation and Stability in PHD2+/− Mice

Coverage of endothelial cells by mural cells renders vessels more mature, tight and stable (Xian et al., 2006) and reduces tumor cell intravasation (Gerhardt and Semb, 2008). Double-staining tumor sections for the mural marker-smooth muscle actin (SMA) and the endothelial marker CD31 revealed that more SMA+ cells covered tumor vessels in PHD2+/− mice (pericytes per optical field: 21.1±2.0 in WT versus 31.5±2.8 in PHD2+/−; N=5; P=0.016; not shown). Endothelial cells in stable vessels are quiescent and surrounded by a laminin (LAM) positive basement membrane. In contrast, tumor vessels are unstable and remodel continuously; because of the hypermotility of tumor endothelial cells, new naked vessels without basement membrane are formed, while existing vessels become denuded and regress (Jain, 2005). Hence, a fraction of tumor vessels consists of endothelial cells surrounded by a LAM+ basement membrane (referred to as "LAM+ vessels"), while another fraction consists of naked endothelial cells without LAM+ basement membrane ("naked LAM− vessels") (Passalidou et al., 2003). Yet other tumor vessels persist as "empty LAM+ sleeves", i.e. LAM+ basement membrane channels, from which endothelial cells egressed (Fenton and Paoni, 2007). Hence, staining tumor sections for CD31 and laminin revealed that, of all tumor vessels analyzed in WT mice, 68±4% were LAM+, 12±2% were naked LAM−, while the remaining 20±3% were empty LAM+ sleeves (N=4; not shown). By contrast, in PHD2+/− mice, up to 89±2% of the vessels were LAM+, while only 4±2% were naked LAM− vessels, and 7±1% were empty LAM+ sleeves (N=4; P<0.0001; not shown). Thus, even though tumors in PHD2+/− mice contained a similar number of vessels, vessels were more mature and stable, which could explain improved perfusion.

PHD2 Deficiency does not Alter the Vascular Network Architecture

We then analyzed whether PHD2 haploinsufficiency altered the abnormal architecture of the tumor vascular network, characterized by vessels of inhomogeneous size and shape (Jain, 2005). Whole mount staining of thick tumor sections for CD31 revealed that the three-dimensional architecture of the tumor microvasculature was comparable in WT and PHD2+/− mice (not shown). In both genotypes, tumor vessels had a complex, disorganized pattern without stereotyped hierarchy. However, in WT mice, the endothelial wall of tumor vessels was thick, disorganized, irregular, and often discontinuous with holes ("honeycomb" appearance), with endothelial cells protruding in the lumen and perivascular area, thereby enlarging the external vessel size (not the lumen; see above). In contrast, in PHD2+/− mice, the wall of tumor vessels was sharply demarcated with clearly defined boundaries and branching points, and endothelial cells forming a continuous smooth lining without protrusions, resulting in a more regular external vessel size and shape (not shown). Thus, partial loss of PHD2 did not substantially alter the overall three-dimensional architecture of the vascular network, but seemed to alter the endothelial lining.

Stromal PHD2 Haploinsufficiency Induces "Endothelial Normalization"

Figure 4:
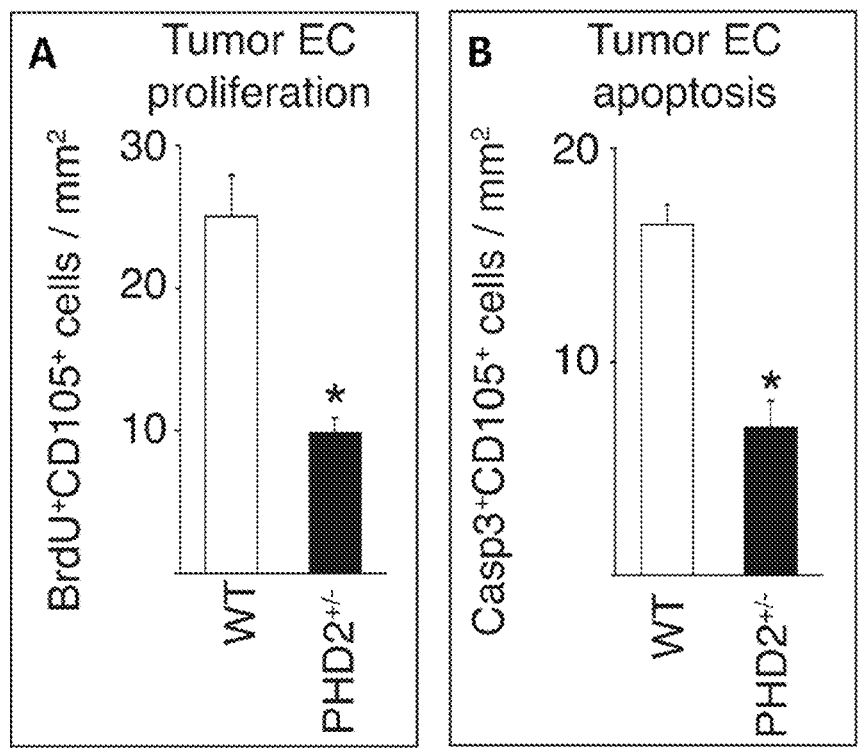
FIG. 4: ENDOTHELIAL CELL NORMALIZATION IN PHD2+/− MICE. A, Reduced tumor EC proliferation in PHD2+/− mice (staining for BrdU and CD105; N=5, P<0.001). B, Reduced tumor EC apoptosis in PHD2+/− mice (staining for cleaved caspase-3 and CD105; N=5, P<0.001). Asterisks in A,B denote statistical significance.

We then analyzed in further detail the normalization of the tumor endothelial layer in PHD2+/− mice. Scanning electron microscopy revealed that tumor endothelial cells in WT mice exhibited signs of a hyperactive, non-quiescent endothelium, with few signs of contact-inhibition. Endothelial cells were not only loosely connected, but also appeared detached from each other, with intercellular gaps, protruding filopodia-like extensions in the lumen, and exposing irregular cell borders, arranged as a pseudo-stratified multiple cell layer, thereby partially obstructing the lumen (not shown). Furthermore, endothelial cells were highly fenestrated (not shown). In contrast, tumor vessels in PHD2+/− mice were lined by a regular, orderly formed, single endothelial monolayer with cobblestone appearance (resembling a "phalanx" of the Greek military formation); this lining was continuous and tightly packed, with a normal polarity and few fenestrations (not shown), as a quiescent endothelium (Baluk et al., 2005; Jain, 2005; McDonald and Choyke, 2003). Accordingly, tumor endothelial cell proliferation and apoptosis were reduced in PHD2+/− mice (FIG. 4A, B). The genotypic differences in endothelial cell morphogenesis were only detected in tumors, as healthy renal and hepatic endothelium exhibited a comparable ultrastructural morphology in both genotypes (not shown).

Molecular analysis revealed that the endothelial cell barrier was tighter. Indeed, immunostaining for the tight junction marker ZO-1 (zona occludens) revealed that ZO-1+ tight junctions in tumor vessels extended over longer distances in PHD2+/− endothelial cells in situ (length of ZO-1+ junctions: 3.98±0.90 µm in WT versus 4.98±0.91 µm in PHD2+/−; N=8; P<0.0001; not shown). Similar findings were obtained when staining for another tight junctional marker claudin-5 (length of claudin-5+ junctions: 4.7±0.2 µm in WT versus 5.5±0.2 µm in PHD2+/−; N=6; P=0.003).

Tumor endothelium is often pro-thrombotic, another sign of hyperactivation. Scanning electron microscopy revealed that tumor vessels in WT mice had intravascular fibrin threads and clots, which can impair perfusion of the tumor vessels. These features of increased coagulation which can impair perfusion were much less prevalent in PHD2+/− mice (data not shown). Morphological quantification confirmed that tumor vessels contained fewer fibrin(ogen)-immunoreactive deposits in PHD2+/− mice (fibrin+ area, % of total tumor area: 2.8±0.4% in WT versus 1.1±0.4% in PHD2+/−; N=6; P=0.01; data not shown).

Loss of PHD2 Induces a "Phalanx Endothelial" Phenotype

Figure 5:
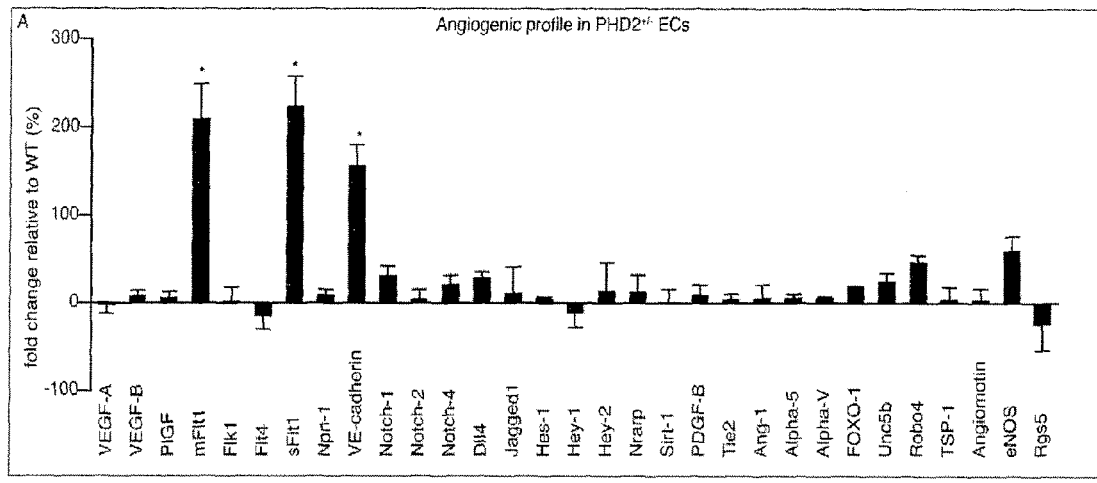
FIG. 5: ENHANCED (S)FLT1 AND VE-CADHERIN LEVELS IN PHD2+/− ENDOTHELIAL CELLS. A, RT-PCR analysis of angiogenic genes; bars represent the change in gene expression in PHD2+/− ECs (% of WT levels; P<0.01). B, RT-PCR analysis, revealing elevated levels of mFlt1, sFlt1 and VE-Cadherin in tumor ECs of PHD2+/− mice (N=4, P<0.05). Asterisks in A,B denote statistical significance.
Figure 5:
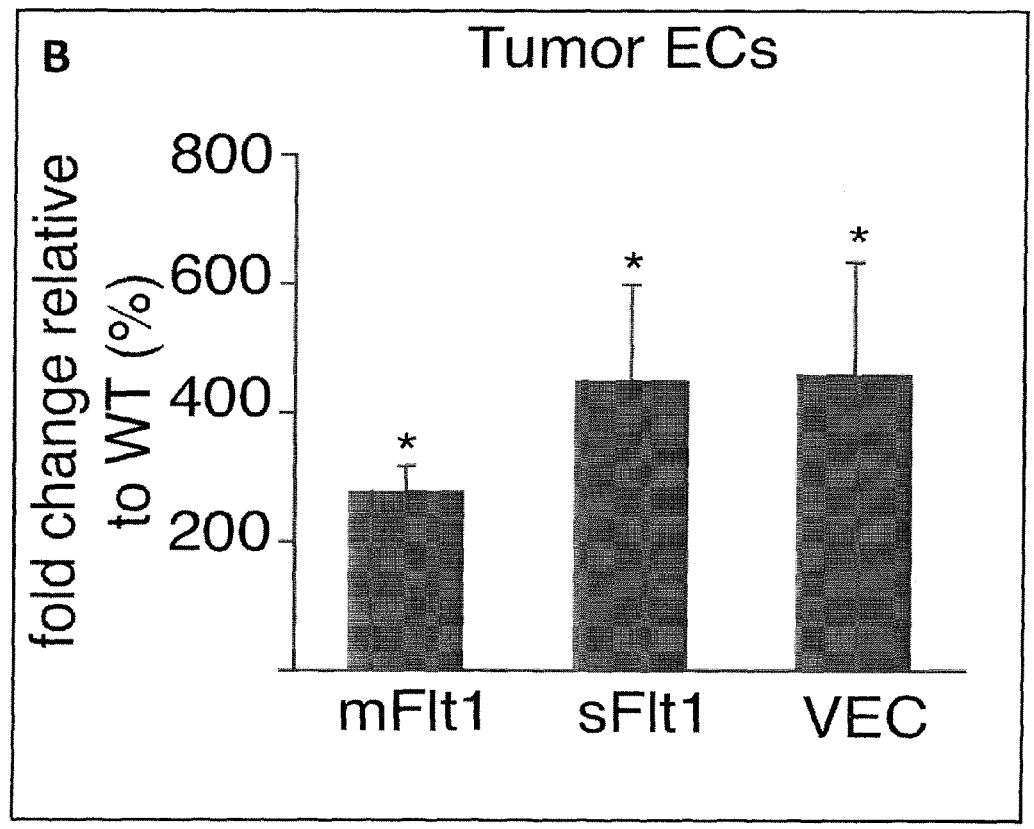
Figure 15:
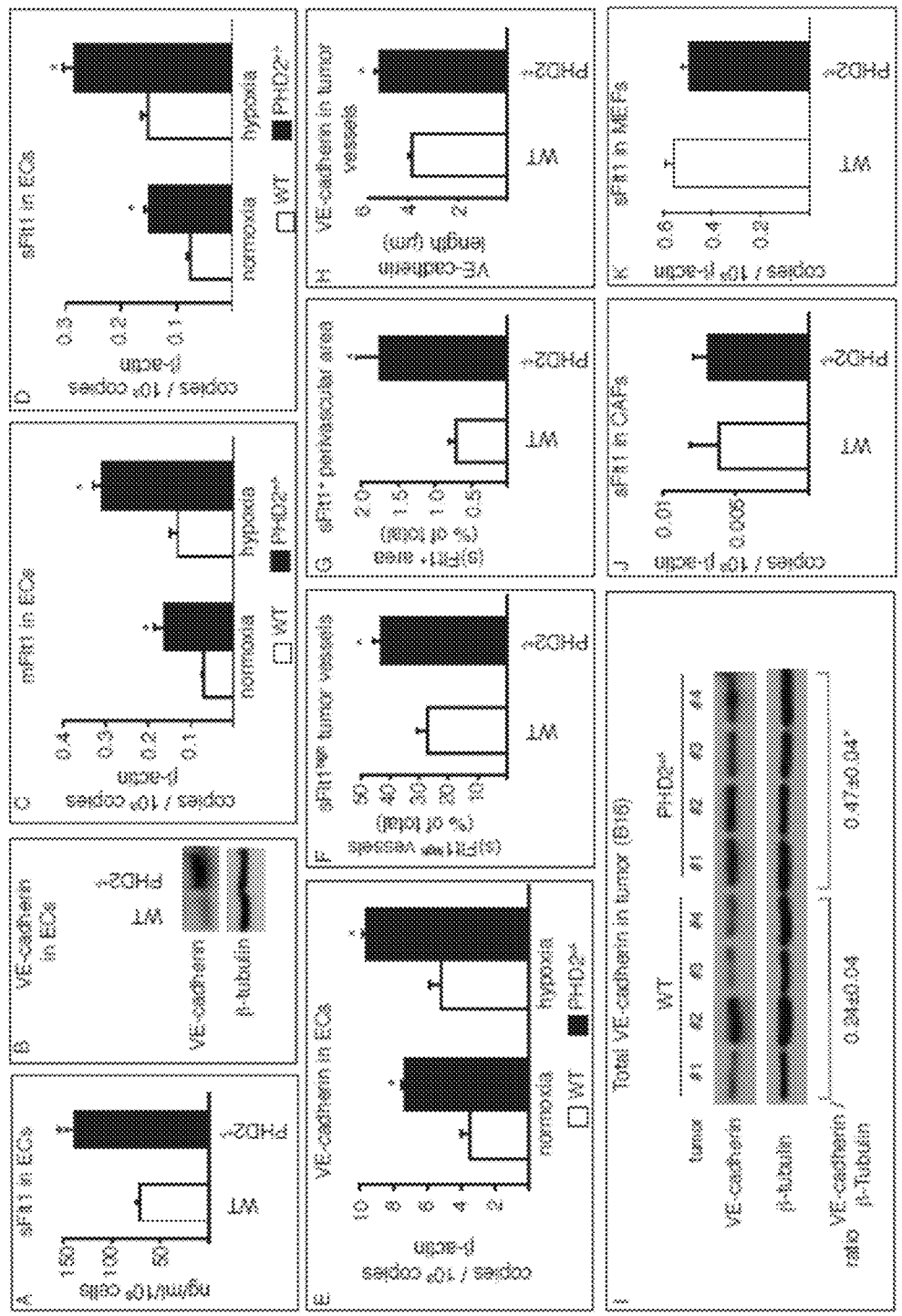
FIG. 15: ENHANCED SFLT1 AND VE-CADHERIN LEVELS IN PHD2+/− ENDOTHELIAL CELLS. A, ELISA revealing increased levels of sFlt1 in conditioned medium of primary PHD2+/− lung endothelial cells. B, Immunoblot revealing increased levels of VE-cadherin in PHD2+/− endothelial cells. C-E, RT-PCR analysis, revealing increased mRNA levels of membrane bound Flt1 (mFlt1) (C), sFlt1 (D) and VE-cadherin (E) in PHD2+/− endothelial cells in normoxia and hypoxia (1% oxygen). F,G, Morphometric quantification of tumor sections immunostained for the endothelial marker CD105 and (s)Flt1 (using an antibody that recognizes the extracellular portion of Flt1) revealing that the number of (s)Flt1+ tumor vessels (F) and the accumulation of sFlt1 in the vascular and perivascular tumor environment (G) are increased in PHD2+/− mice. H, Morphometric quantification of tumor sections immunostained for the endothelial marker CD105 and VE-cadherin revealing that tumor endothelial cells in PHD2+/− mice expressed longer VE-cadherin+ junctions. I, Immunoblot revealing increased VE-cadherin levels in B16 tumors in PHD2+/− mice (by densitometric quantification, 2-fold increase in [VEC/β-tubulin] ratio) (N=4, P=0.006). J,K, RT-PCR analysis, revealing comparable sFlt1 transcript levels in PHD2+/− cancer associated fibroblasts (CAFs) or mouse embryonic fibroblasts (MEFs). Asterisks in panels A,C,D,E,F,G,H,I denote statistical significance (P<0.05).

To characterize molecularly how haploinsufficiency of PHD2 regulates tumor endothelial phenotypes, we analyzed in confluent endothelial cells the expression of a set of candidate genes, known to regulate endothelial cell morphogenesis or fate (i.e., tip cell versus stalk cell). Of all candidates analyzed, soluble VEGFR-1 (sFlt1) and membrane-anchored VEGFR-1 (mFlt1) were significantly upregulated at the mRNA and protein level in PHD2+/− cells (FIG. 5A; FIG. 15A, B). A third gene, which was selectively upregulated in these cells, was the junctional adherens molecule VE-cadherin, both at the mRNA (FIG. 5A) and protein level (FIG. 15B). Transcript levels of mFlt1, sFlt1 and VEcadherin were higher in PHD2+/− endothelial cells, cultured at 1% O2 (i.e., the average oxygen tension in tumors) (FIG. 15C-E). Also, immunostaining of tumor sections and RT-PCR analysis of freshly isolated tumor endothelial cells confirmed that (s)Flt1 and VEcadherin were upregulated in tumor endothelial cells in PHD2+/− mice (FIGS. 5B & 15F-H). VEcadherin protein levels were also higher in tumors in PHD2+/− mice, despite comparable vessel area and density (FIG. 15I). These genotypic differences in sFlt1, mFlt1 and VE-cadherin expression were specific, as expression levels were comparable for other genes involved in the specification of endothelial tip cells (Flk1, Flt4, Dll4, UncSb, neuropilin-1, PDGF-B, angiomotin) or stalk cells (Notch signaling, Robo4) (FIG. 5A) (Aase et al., 2007; Gerhardt et al., 2003; Gerhardt et al., 2004; Hellstrom et al., 2007; Jones et al., 2008; Lu et al., 2004; Tammela et al., 2008). Also, endothelial cells of either genotype expressed comparable levels of additional angiogenic molecules (members/receptors of the VEGF, angiopoietin and integrin family, etc). Interestingly, levels of Rgs5, a gene counteracting tumor vessel normalization (Hamzah et al., 2008), tended to be reduced, while levels of eNOS and Robo4, which promote vessel normalization (Jones et al., 2008; Kashiwagi et al., 2008), were slightly higher in PHD2+/− endothelial cells (FIG. 5A). Furthermore, PHD2 haplodeficiency failed to upregulate sFlt1 in cancer-associated fibroblasts or mouse embryonic fibroblasts (FIG. 15J, K).

Example 6

Biological Responses of "Phalanx" PHD2+/− Endothelial Cells

Figure 6:
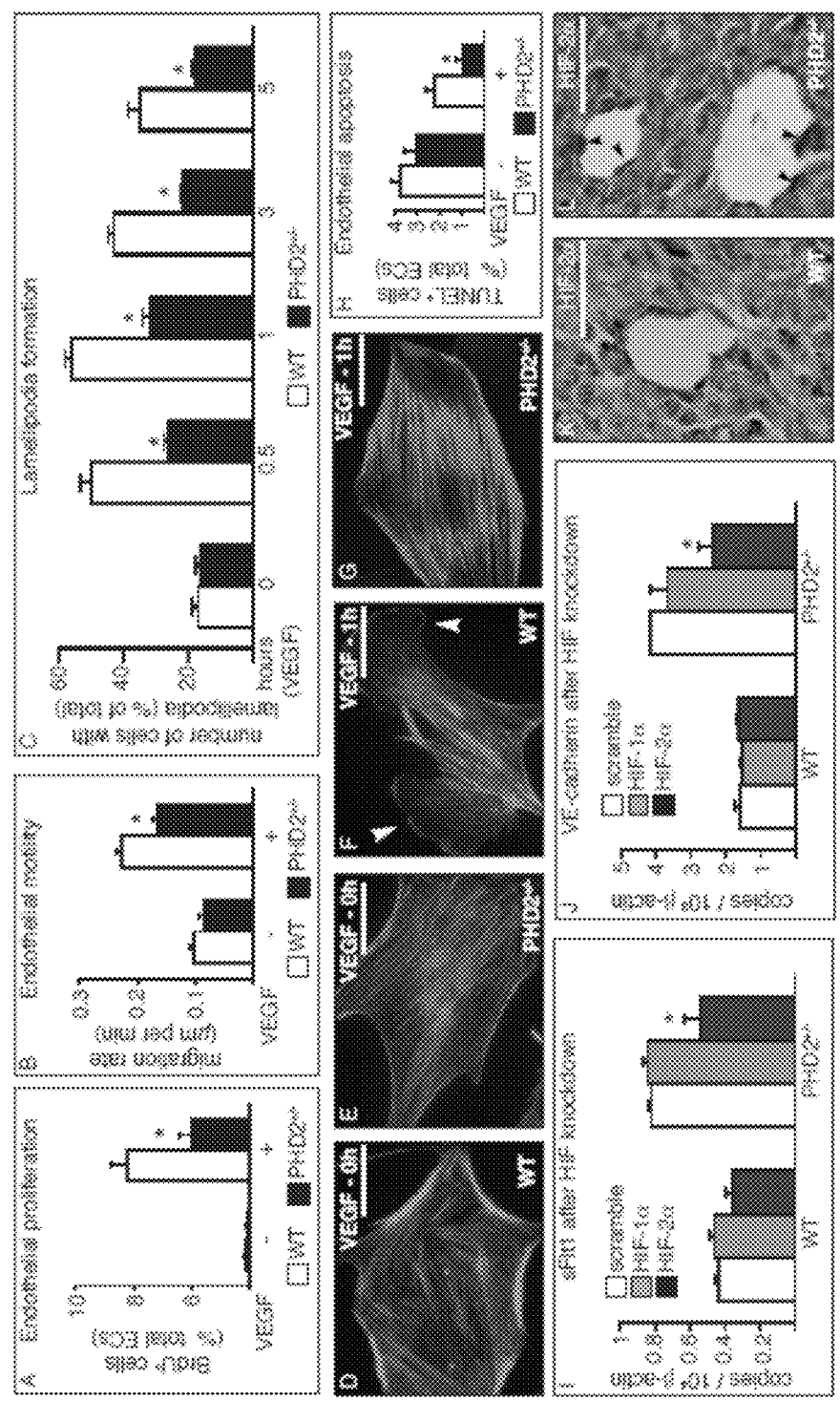
FIG. 6: IN VITRO CHARACTERIZATION OF PHD2+/− ENDOTHELIAL CELLS. A,B, Reduced proliferation (A) and motility (B) of PHD2+/− ECs in response to VEGF (N=6, P<0.05). C, Lamellipodia formation in response to VEGF is impaired in PHD2+/− ECs (N=100 cells, P<0.05). D-G, Phalloidin staining, revealing comparable actin cytoskeleton in WT (D) and PHD2+/− (E) ECs in baseline conditions, and the formation of lamellipodia (arrowheads) in a WT (F) but not in a PHD2+/− (G) EC upon VEGF stimulation. H, TUNEL staining, revealing reduced apoptosis of starved PHD2+/− ECs in response to VEGF (N=6; P<0.02). I,J, Silencing of HIF-2α inhibits the upregulation of sFlt1 (I) and VE-cadherin (J) expression in normoxic PHD2+/− ECs (N=3; P<0.05). K,L, Staining of HIF-2α, revealing stronger immunoreactive signal (arrowheads) in tumor ECs in PHD2+/− (L) than WT (K) mice. Bar: 50 μm in D-G and 25 μm in K,L. Asterisks in A,B,C,H denote significance relative to WT; asterisks in I,J denote significance relative to scramble RNAi.
Figure 16:
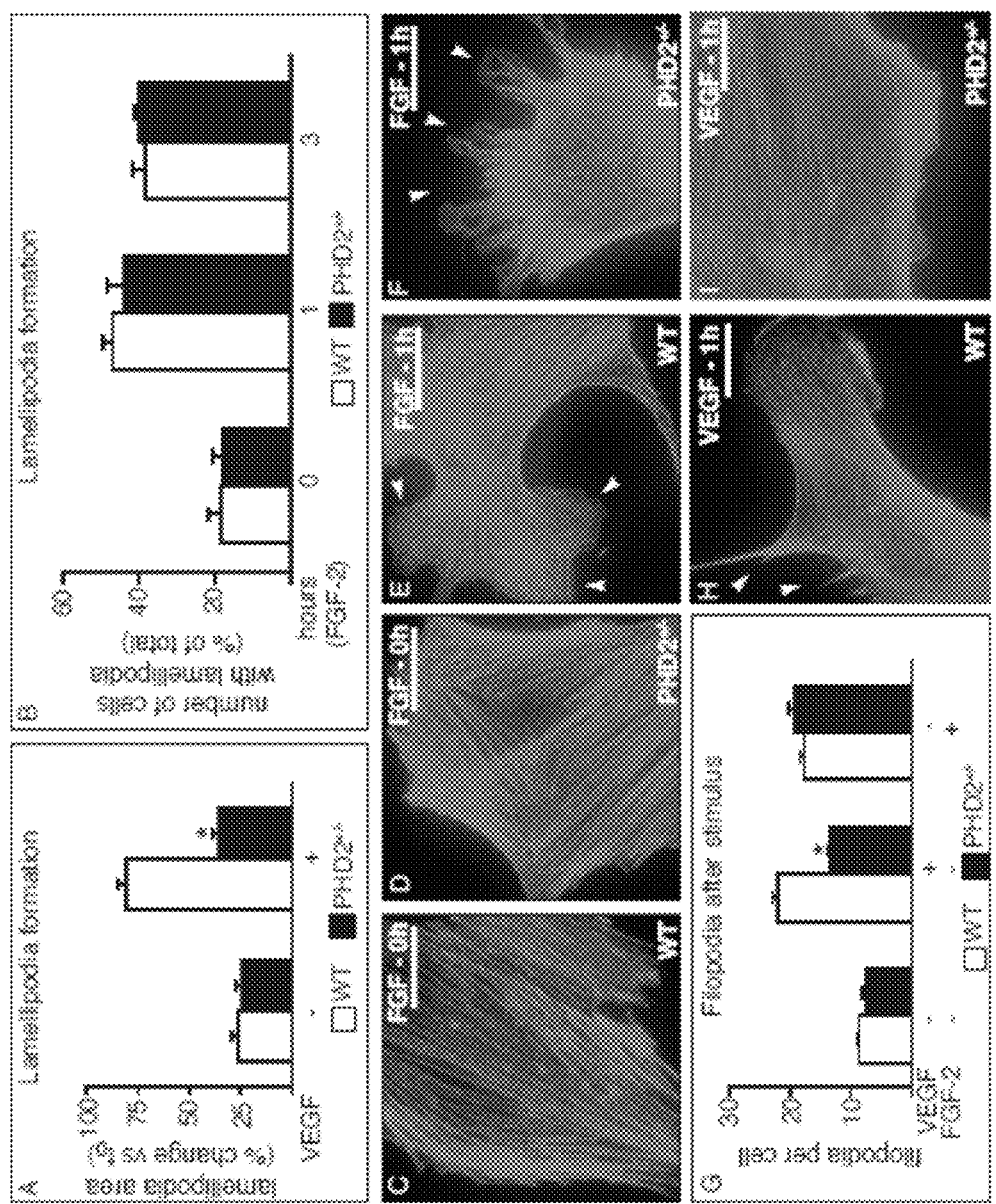
FIG. 16: IN VITRO CHARACTERIZATION OF PHD2+/− ENDOTHELIAL CELLS. A,B, Reduced lamellipodia formation of PHD2+/− endothelial cells in response to VEGF. Panel A shows the reduction of lamellipodial area in PHD2+/− endothelial cells upon VEGF stimulation; the data are expressed as % of change after 1 hour of stimulation versus the start of the experiment (t0). Panel B shows the % of endothelial cells displaying lamellipodia upon 1 and 3 hours FGF-2 stimulation. C-F, Phalloidin staining, revealing a comparable distribution of actin filaments in a WT (C) and PHD2+/− (D) endothelial cell in baseline conditions. In addition, reorganization of the actin cytoskeletal network and lamellipodia formation (arrowheads) are comparable in WT (E) and PHD2+/− (F) endothelial cells upon stimulation with FGF-2. G-I, Reduced filopodia formation of PHD2+/− endothelial cells in response to VEGF but not FGF-2. Panel G shows the measurement of the number of filopodia per cell at the start of the experiment (t0) and after 1 hour of simulation with VEGF or FGF-2, in WT and PHD2+/− endothelial cells. Phalloidin staining in panel H,I indicates reduced filopodia formation in a PHD2+/− endothelial cell upon VEGF stimulation (I) as compared to a WT cell (H) (arrowheads indicate filopodia). Bar: 50 µm in panels C,D,E,F,H,I. Asterisks in panels A,G denote statistical significance (P<0.05).

We then studied the response of PHD2+/− endothelial cells to VEGF, since elevated levels of VE-cadherin and (soluble) Flt1 are known to modulate these responses (Carmeliet et al., 1999; Grazia Lampugnani et al., 2003; Kappas et al., 2008; Kearney et al., 2002), and excess VEGF may negatively regulate vessel maturation (Greenberg et al., 2008; Stockmann et al., 2008). Proliferation and motility of PHD2+/− endothelial cells were reduced upon VEGF stimulation (FIG. 6A,B). We also quantified the formation of lamellipodia, i.e., sheet-like membrane protrusions containing a highly branched actin meshwork, and filopodia that endothelial (tip) cells use to navigate in response to VEGF (Gerhardt et al., 2003). Phalloidin staining or video imaging revealed that, in baseline conditions, a comparably low number of WT and PHD2+/− endothelial cells formed lamellipodia and filopodia, with a homogeneous distribution of actin filaments (FIG. 6C, F; FIG. 16A,G, H). In response to VEGF, WT cells formed extensive lamellipodia and filopodia, with polarized reorganization of the actin cytoskeleton (FIGS. 6C,F & 16A,G,H), while PHD2+/− cells failed to do so (FIGS. 6C,G & 16A,G,I). This defect was specific for VEGF, as PHD2+/− cells normally formed lamellipodia and filopodia in response to FGF-2 (FIG. 16B-G). The corneal neovascularization response to FGF-2 was also preserved in PHD2+/− mice (not shown). Apoptosis, induced by serum deprivation, was, however, reduced in PHD2+/− endothelial cells, slightly in baseline conditions and, more significantly, upon stimulation with VEGF (FIG. 6H). Overall, PHD2+/− endothelial cells were less responsive to the mitogenic and migratory activity of VEGF, while being more sensitive to the VEGF survival activity.

To assess whether HIFs might mediate the endothelial phalanx phenotype, we silenced expression of HIF-1α or HIF-2α for >80% by transfecting PHD2+/− endothelial cells with RNAi oligomers. Notably, the upregulation of sFlt1 and VE-cadherin was inhibited primarily by silencing HIF-2α in normoxic conditions (FIG. 6I,J), while silencing of HIF-1α also contributed in hypoxic conditions, albeit at a lower level (not shown). Immunostaining revealed a stronger signal for HIF-2α in tumor vessels in PHD2+/− mice (HIF-2α+ tumor vessels, % of vessels with lumen: 30±6 in WT versus 49±4 in PHD2+/−; N=4; P=0.04; FIG. 6K,L).

Endothelial Haplodeficiency of PHD2 Recapitulates the Key Phenotype

The above in vitro data demonstrate that PHD2 haplodeficiency induces molecular changes in endothelial cells, that can explain the PHD2+/− phenotype in vivo. To confirm the role of PHD2 in endothelial cells in vivo, we generated endothelial conditional PHD2 (PHD2Cre/+) heterozygous mice, obtained by intercrossing PHD2lox/+ mice with Tie2:Cre mice. Analysis of PHD2Cre/+ mice and their corresponding control PHD2lox/+ littermates revealed that conditional haplodeficiency of PHD2 sufficed to phenocopy the key findings, observed in PHD2+/− mice. Indeed, primary tumor growth was comparable, but metastasis was reduced (FIG. 7A,B), while tumor vessel density (FIG. 7C), area (not shown) and architecture (FIG. 7D,E) were comparable. However, tumors were better oxygenated (FIG. 7F), and tumor vessels showed the cardinal morphological signs of EC normalization (FIG. 7D,E,G,H). The relevance of endothelial PHD2 was further underscored by findings that ubiquitous haplodeficiency of PHD2 did not alter the accumulation of inflammatory cells and cancer-associated fibroblasts (not shown). While these conditional knockout studies highlight a role for endothelial PHD2, they obviously do not rule out a possible role of leukocyte or fibroblast PHD2 in tumor biology.

Example 7

Anti-Tumor Treatment of PHD2+/− Mice

Figure 18:
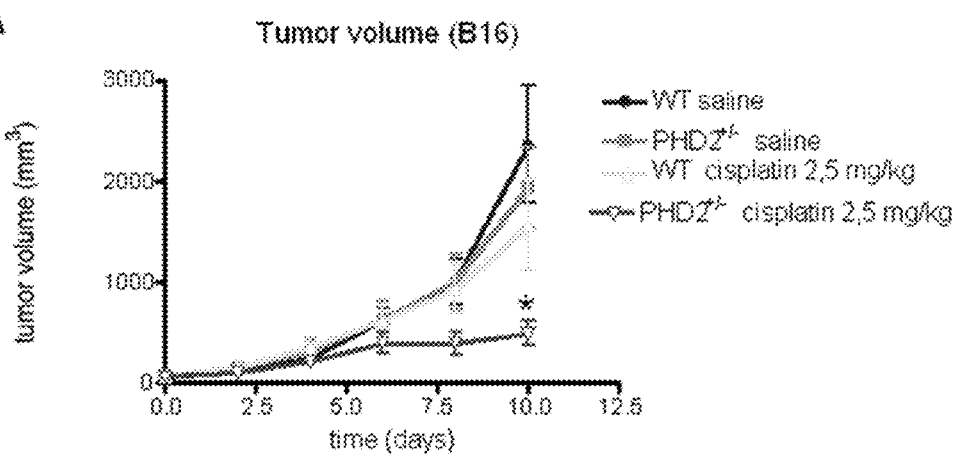
FIG. 18: RESPONSE TO CHEMOTHERAPY IN PHD2+/− MICE. Cisplatin treatment (2.5 mg/kg, 3× week) reduced the volume (A) and weight (B) of B16 tumor in PHD2+/− mice. The same dose was, however, not effective in WT tumor-bearing mice (N=10, P=0.0013). As negative control, saline solution was used. Asterisk denotes statistical significance (P<0.01 in A; P=0.05 in B). For tumor growth rate, see FIG. 4A, B; for survival see FIG. 11E.
Figure 18:
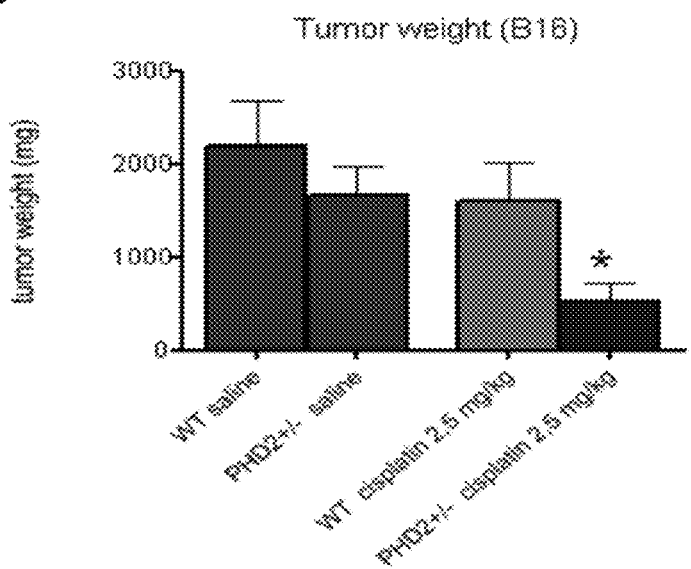
Figure 21:
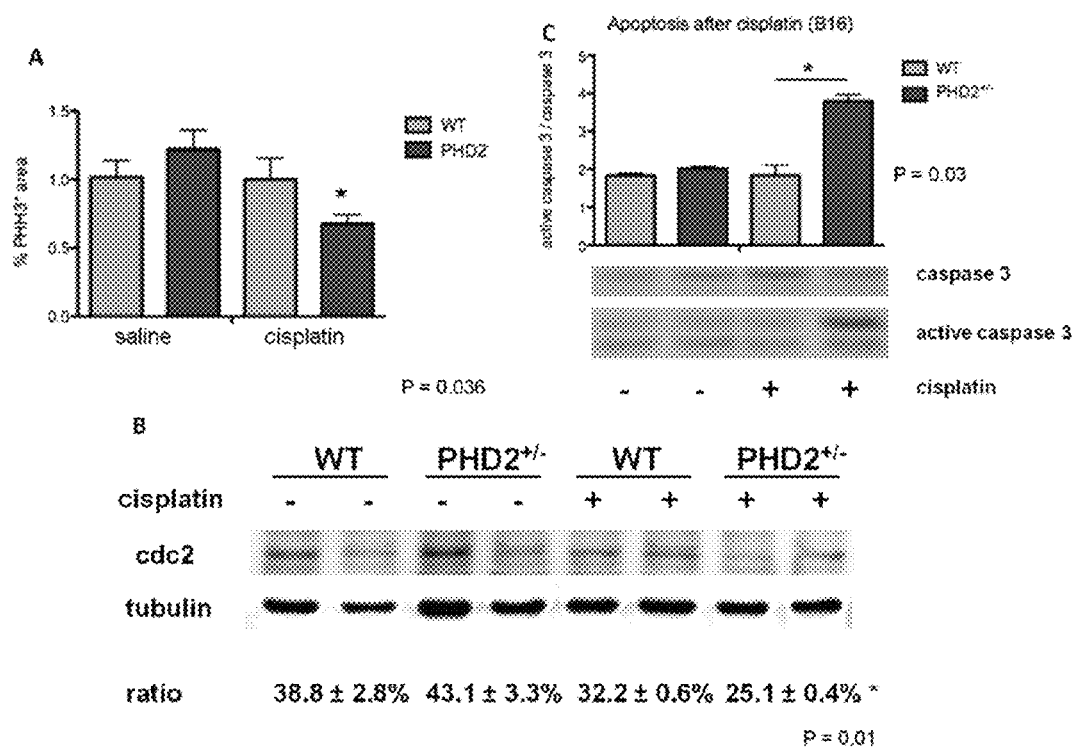
FIG. 21: LESS TUMOR PROLIFERATION AND MORE TUMOR APOPTOSIS UPON CHEMOTHERAPY IN PHD2+/− MICE. Proliferation is reduced in tumors implanted in PHD2+/− mice upon cisplatin treatment compared to WT mice, as evaluated by area of PHI-13 positive staining (A) (P=0.036) or cdc2/tubulin ratio (B) (P=0.01). The difference is due to the combination with cisplatin, as the saline control shows no effect. C, Apoptosis in tumors implanted in PHD2+/− mice is increased upon cisplatin treatment, as evaluated by the ratio active caspase3/total caspase 3 (P=0.03). Asterisk in A-C indicates statistical significance.
Figure 22:
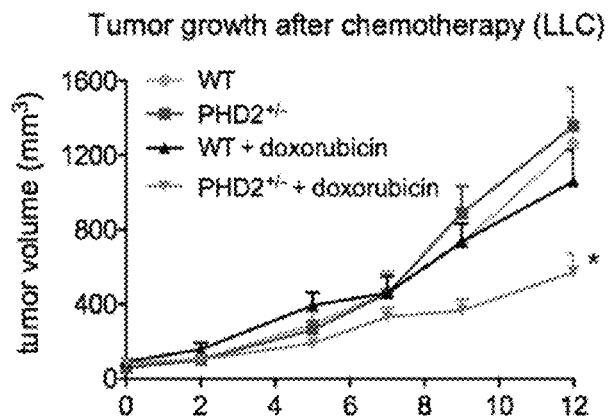
FIG. 22: RESPONSE TO CHEMOTHERAPY IN PHD2+/− MICE. Doxorubicin treatment (2.5 mg/kg, 3× week) reduced the volume of LLC (Lewis lung carcinoma) tumor in PHD2+/− mice. The same dose was, however, not effective in WT tumor-bearing mice. As negative control, saline solution was used. Asterisk indicates statistical significance. X-axis: number of days. Remark the resemblance to what is seen for another chemotherapeutic agent in another cancer model (FIG. 18A).

Since tumor cells in PHD2+/− mice are better perfused and oxygenated than in WT mice, one could speculate that they should be more responsive to chemo- and radiotherapy. Indeed, it was shown that the increased tumor perfusion in PHD2+/− mice improves the tumor response to chemotherapy. A suboptimal dose of cisplatin (2.5 mg/kg; 3×/week), which does not kill B16 tumor cells in WT mice, was effective in PHD2+/− mice. Indeed, 11 days after initiation of chemotherapy, tumors were 60% smaller in PHD2+/− than WT mice and weighed considerably less (FIGS. 18A and B). Proliferation is reduced in tumors implanted in PHD2+/− mice upon cisplatin treatment (FIG. 21 A, B), while apoptosis in tumors implanted in PHD2+/− mice is increased upon cisplatin treatment, as shown by the amount of active caspase 3 (FIG. 21C). Moreover, these findings are not due to a cisplatin-specific effect, as tumors implanted in PHD2+/− mice are also responsive to a suboptimal dose of doxorubicin (2.5 mg/kg; 3×/week) in a Lewis Lung Carcinoma (LLC) model (FIG. 22)

These findings indicate that the drugs are delivered more effectively, due to the better perfusion observed in the vessels where PHD2 is inhibited. Thus, while PHD2 inhibition alone may be useful for treatment and/or prevention of metastasis, a combined treatment with other anti-cancer drugs may be even more effective.

Example 8

Reduced Organ Damage Resulting from Chemotherapy in PHD2+/− Mice

Organ damage (e.g., renal damage, liver damage) is a known side effect of many traditional cancer treatments such as radiotherapy or chemotherapy. In fact, many therapies and diagnostic methods are known to cause iatrogenic effects; one of the best characterized examples apart from chemotherapy is the nephrotoxic effects of contrast media.

Figure 23:
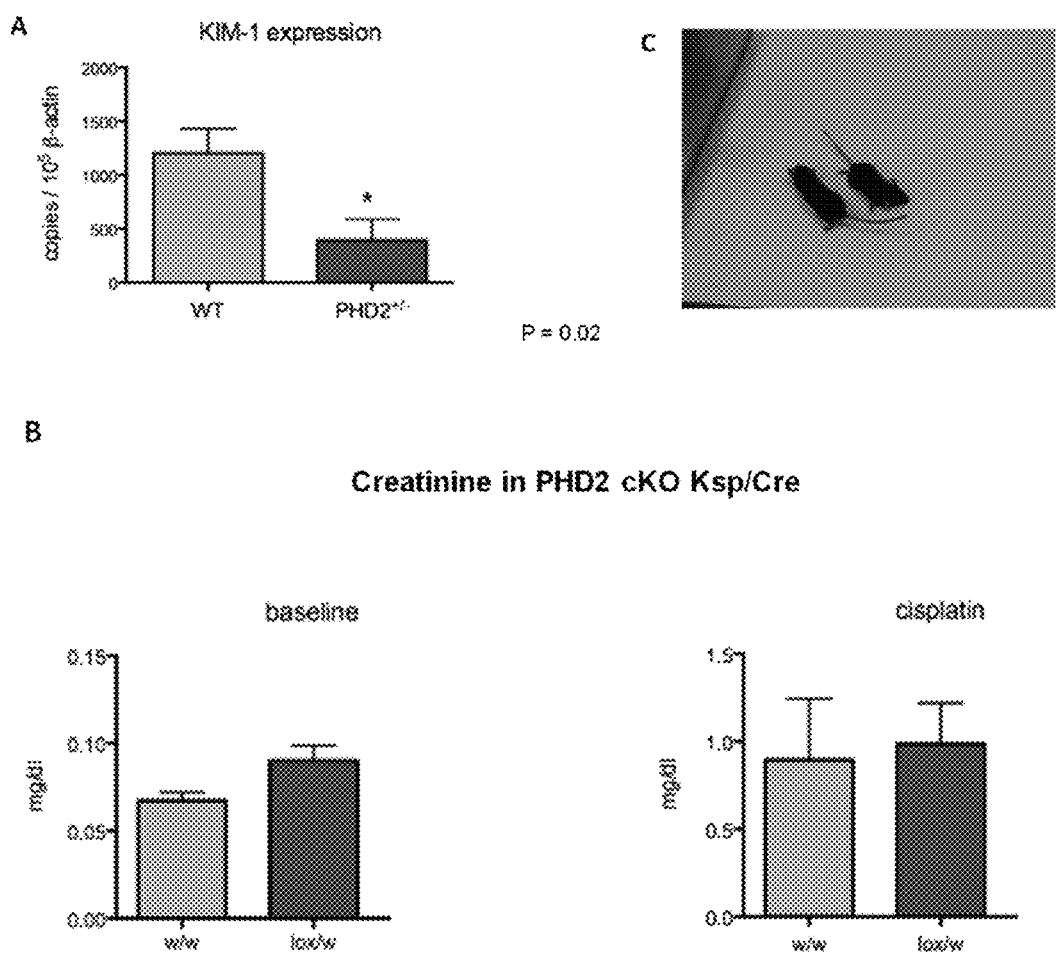
FIG. 23: RENAL DAMAGE IS REDUCED IN PHD2+/− MICE UPON CISPLATIN TREATMENT. A, levels of Kidney injury molecule-1 (KIM-1) in kidneys of PHD2+/− and WT mice after cisplatin acute treatment Asterisk denotes statistical significance (P=0.02); B, Creatinine levels in PHD2 cKO Ksp/Cre, only heterozygous for PHD2 in epithelial cells, are not different from those in WT mice in baseline conditions (left panel) or upon acute cisplatin treatment (right panel); C, video still showing an endothelial-specific heterozygous mouse (Tie2-Cre:PHD2lox/wt mouse, left) and a WT mice treated with cisplatin (right). Note the tail rigidity in WT mouse, in complete video hind leg paralysis can be observed.

Remarkably, PHD2+/− mice receiving acute cisplatin treatment (see example above) display considerably less organ damage (e.g., renal damage) than their WT counterparts treated in the same manner. This could be evaluated histologically (data not shown), but also is apparent on the molecular level. For instance, Kidney injury molecule-1 (KIM-1) is downmodulated in PHD2+/− kidneys after cisplatin acute treatment (FIG. 23A). To check whether the features observed using systemic PHD2 inhibition could be recapitulated using tissue-specific inhibition, epithelium- and endothelium-specific knock-outs were made. Protection against cisplatin nephrotoxicity is not epithelial-mediated, as shown by similar creatinine levels in PHD2 cKO Ksp/Cre and WT mice (FIG. 23B). However, endothelial-specific heterozygous mice (Tie2-Cre:PHD2lox/wt mice) are protected from renal damage, while their wild-type littermates display considerable renal damage, up to the point of showing hind leg paralysis and increased tail rigidity (FIG. 23C, complete video not included). Thus, protection against iatrogenic effects obtained by systemic PHD2 inhibition could also be obtained using endothelial-specific PHD2 inhibition.

Figure 19:
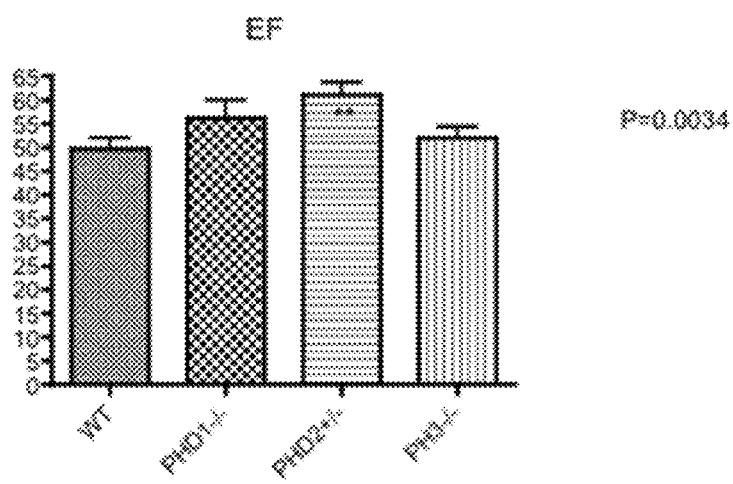
FIG. 19: LESS CARDIOTOXICITY UPON DOXORUBICIN TREATMENT IN PHD2+/− MICE. Doxorubicin treatment results in organ damage to the heart, but less so in PHD2+/− mice, as is shown by a higher ejection fraction (EF, panel A) (P=0.003), and fractional shortening (FS, panel B) (P=0.003) than observed for hearts of WT or PHD1−/− or PHD3−/− mice. Hearts of PHD1−/− and PHD3−/− mice show increased diastolic left ventricular mass (LVMd, panel D) (P=0.008 and P=0.016 respectively). Other parameters failed to reach statistical significance. LVDd: Left ventricle diastolic diameter, IVS: Interventricular septum (Wall thickness), PWd: Posterior wall (Wall thickness). EF and FS are measured in percent; all diameters or thickness are measured in mm, volume is $mm^3$. LVM is expressed as mg. This unit is converted from volume of myocardium.
Figure 19:
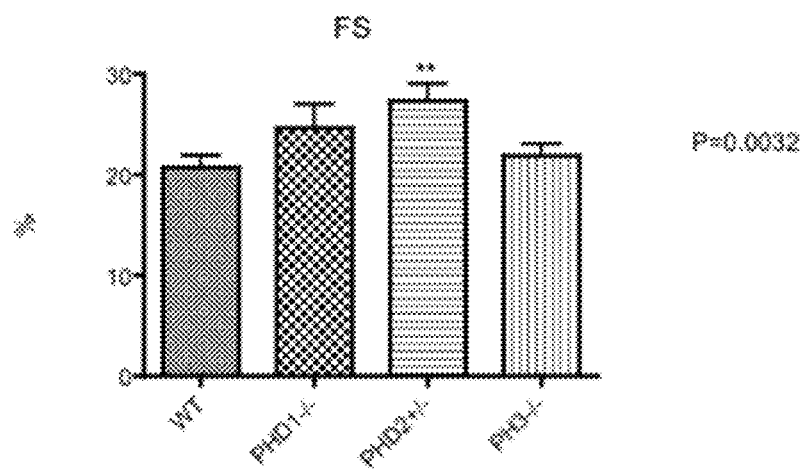
Figure 19:
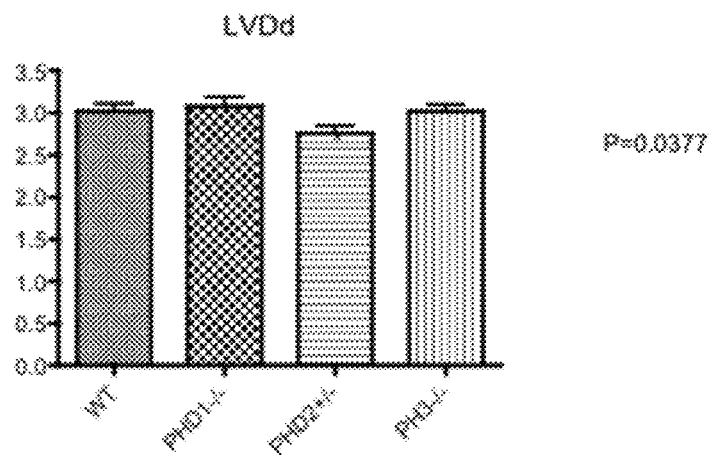
Figure 19:
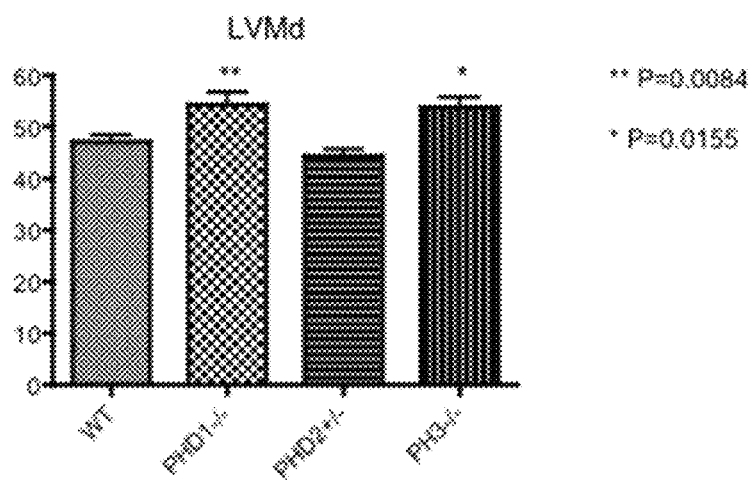
Figure 19:
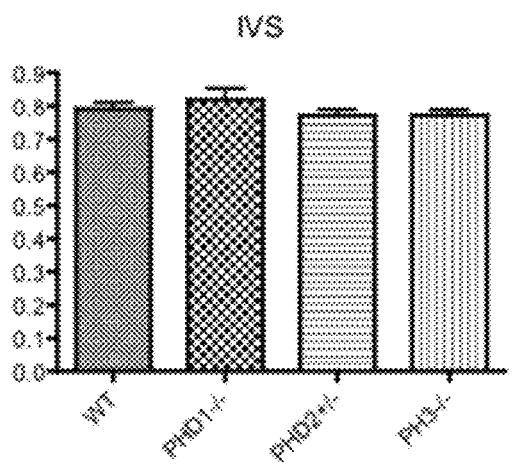
Figure 19:
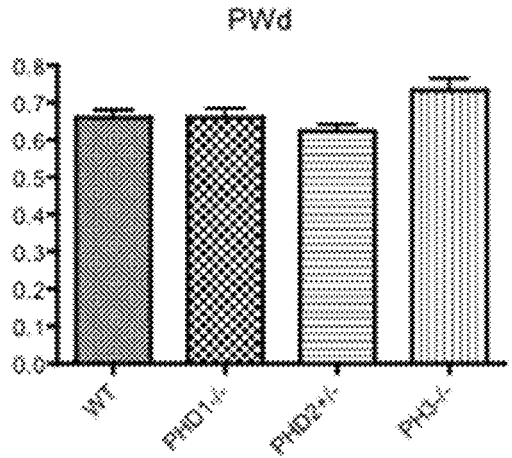
Figure 24:
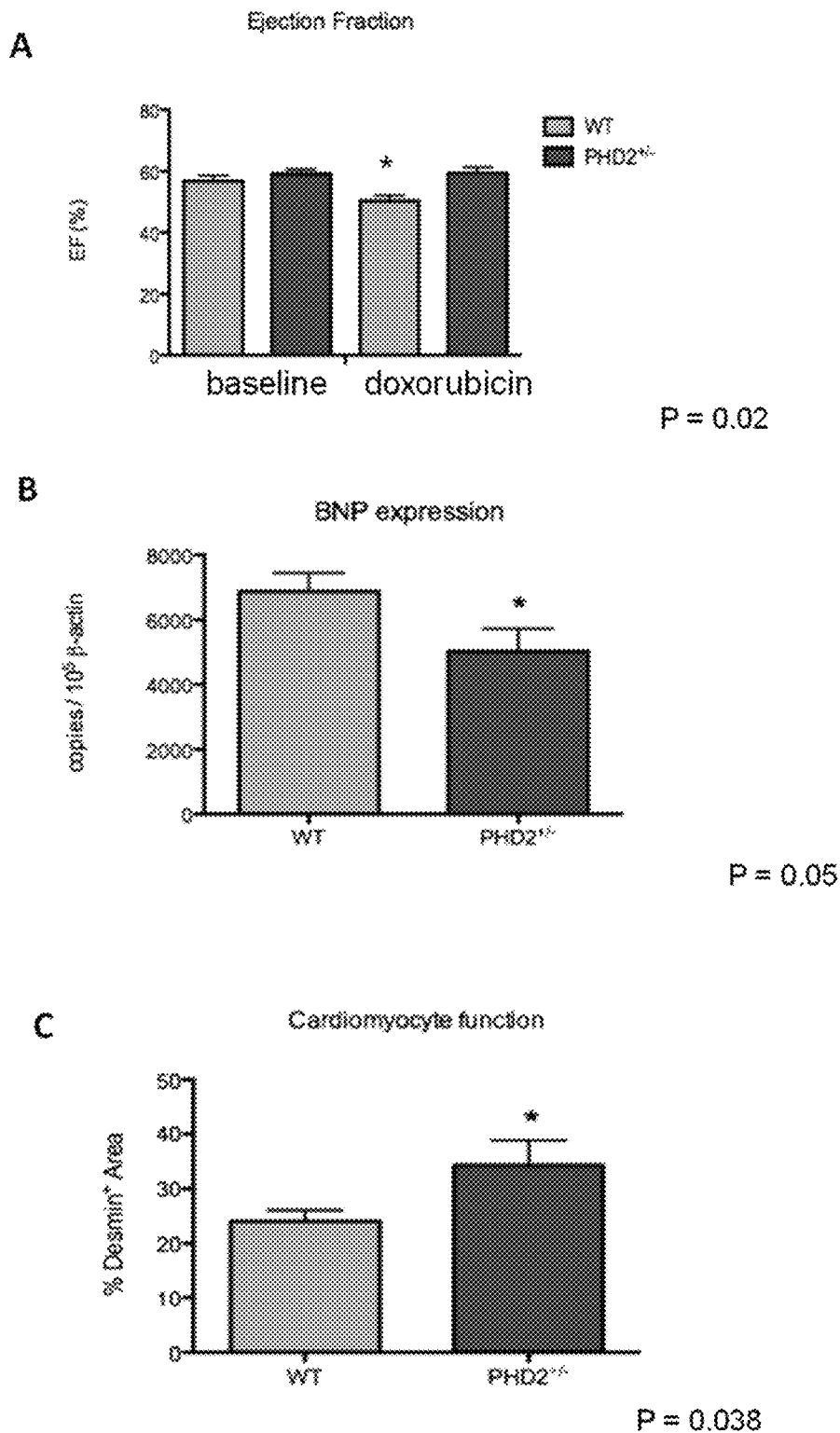
FIG. 24: CARDIOTOXICITY IS REDUCED IN PHD2+/− MICE UPON DOXORUBICIN TREATMENT. A, Ejection fraction in hearts of WT and PHD2 heterozygous mice at baseline and upon doxorubicin treatment. The decrease in WT mice upon doxorubicin treatment is significant (P=0.02); B, BNP expression in hearts of WT and PHD2 heterozygous mice upon doxorubicin treatment (P=0.05); C, Cardiomyocyte function in hearts of WT and PHD2 heterozygous mice upon doxorubicin treatment, as evaluated by area staining positive for desmin (P=0.038); D, Interstitial fibrosis in hearts of WT and PHD2 heterozygous mice upon doxorubicin treatment, as evaluated by area staining positive for Sirius Red. Asterisk in A-D denotes statistical significance.
Figure 24:
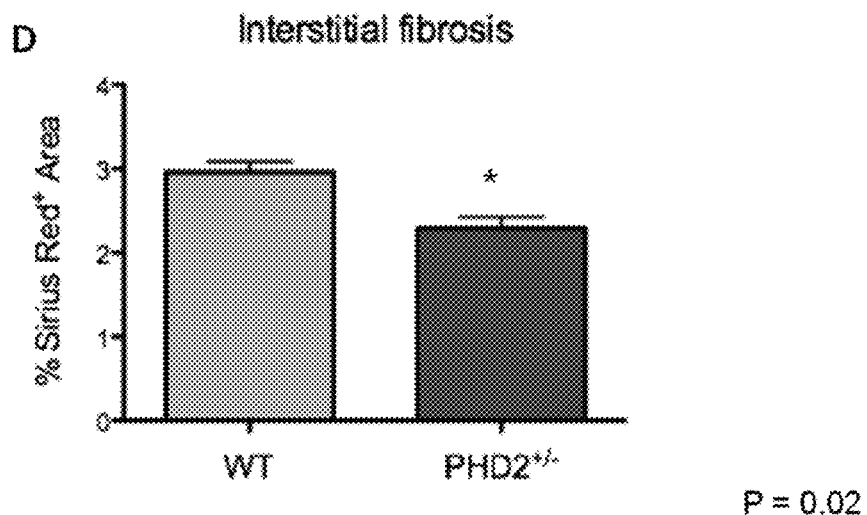

It was evaluated whether these findings could be extended using other iatrogenic agents. To this end, WT and PHD deficient mice were chronically treated with doxorubicin. Doxorubicin is an anthracyclin anti-cancer compound often used in clinical cancer treatment. However, its clinical use is limited because it leads to a cumulative, dose-related cardiotoxicity. Briefly, mice received 3×/week a 2.5 mg/kg doxorubicin dose for four weeks, up to a total cumulative dose of 30 mg/kg. It was found that PHD2+/− mice were protected against cardiac damage. These mice display a higher ejection fraction (EF, the fraction of blood ejected by the ventricle relative to its end-diastolic volume) (FIGS. 19 and 24A) and fractional shortening (FIG. 19A, B) than their WT counterparts or than PHD1 and PHD3 deficient mice. As can be seen from FIG. 24A, PHD2+/− mice maintain or preserve the baseline EF levels upon doxorubicin treatment, while the EF in wild-type mice decreases. A lower ejection fraction or fractional shortening is an indication of a weakening of the heart. In contrast to the PHD2+/− mice, PHD1 and PHD3 deficient mice display a significant cardiac hypertrophy after 2 months of treatment (e.g., FIG. 19D). PHD2+/− hearts express lower levels of Brain Natriuretic Peptide (BNP) upon doxorubicin treatment (FIG. 24B). Cardiomyocyte integrity and function is preserved in PHD2+/− hearts upon doxorubicin treatment (FIG. 24C and data not shown). Moreover, PHD2+/− hearts exhibit reduced interstitial fibrosis upon doxorubicin treatment (FIG. 24D).

Figure 25:
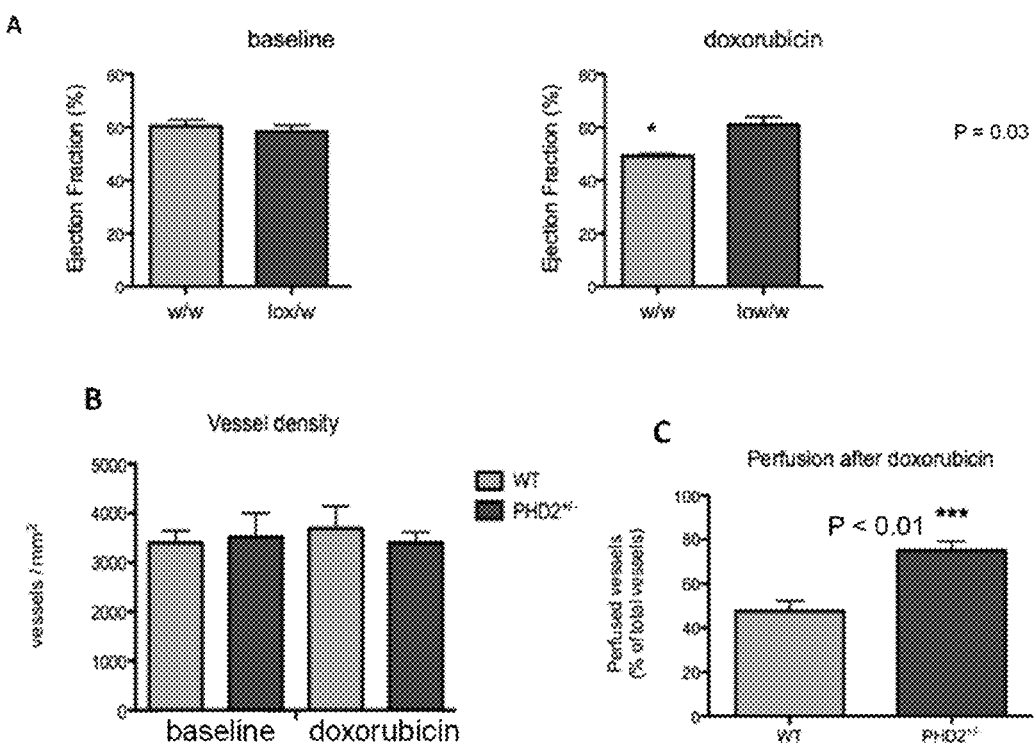
FIG. 25: MECHANISM OF CARDIOPROTECTION OBSERVED IN PHD2+/− MICE. A, Ejection fraction in hearts of WT and endothelial specific PHD2 heterozygous mice at baseline (left panel) and upon doxorubicin treatment (right panel). The decrease in WT mice upon doxorubicin treatment is significant (P=0.03); B, capillary density is the same for WT and PHD2 heterozygous mice at baseline and upon doxorubicin treatment; C, Perfused vessels as percentage of total vessels in hearts of WT and PHD2 heterozygous mice (P<0.01); D, 8-OHdG staining as marker for oxidative stress in hearts of WT and PHD2 heterozygous mice (P=0.01). Asterisks in A, C, D denote statistical significance.
Figure 25:
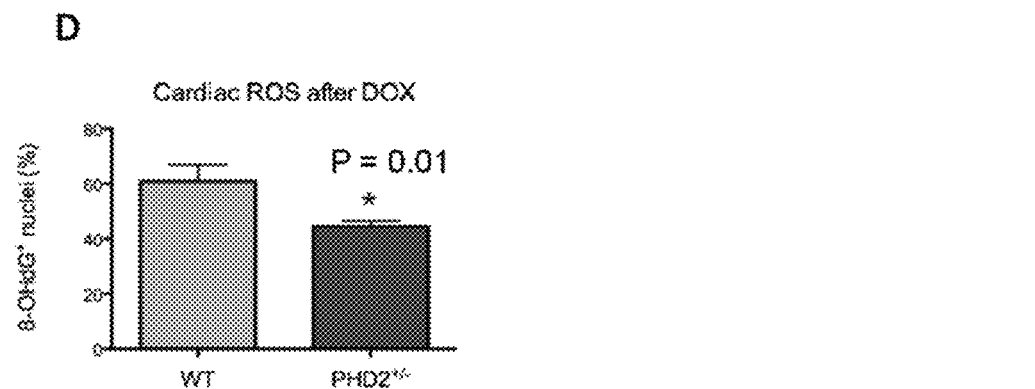

The mechanism of the PHD2+/− cardiac protection was further investigated. Protection against doxorubicin cardiotoxicity was found to be endothelium-mediated, as endothelium-specific heterozygous PHD2 mice also show preservation of baseline EF levels, contrary to WT mice (FIG. 25A). To investigate whether increased angiogenesis was the cause, capillary density was assessed, but capillary density is comparable in PHD2+/− and WT hearts upon doxorubicin treatment (FIG. 25B). However, capillary perfusion is preserved in PHD2+/− hearts upon doxorubicin treatment, while it is not preserved in WT hearts (FIG. 25C, and data not shown). In line with this, oxidative stress is reduced in PHD2+/− hearts upon doxorubicin treatment, as shown by levels of cardiac ROS (FIG. 25D). A preliminary experiment also seems to indicate that PHD2+/− hearts might express higher levels of VE-cadherin in baseline conditions. Thus, the higher perfusion observed in PHD2+/− tissues compared to WT tissue is not due to an increase in the number of vessels, but to better perfused vessels (in practice, an increase in number of functional vessels. However, it is important to note that this is not an effect of angiogenesis).

In conclusion, inhibition of PHD2 leads to less organ damage normally associated with cancer treatment (such as cardiotoxicity, renal damage, liver damage). This may for instance allow to use higher doses of chemotherapeutic drugs or radiotherapy, without the severe side effects.

Example 9

Effect on Metastases in a Spontaneous Tumor Model with Also Partial Inhibition of PHD2 in the Tumor The above-mentioned tumor models employed wild-type tumor cells placed in animals heterozygous for a null allele of PHD2, and demonstrated that a decreased level of PHD2 resulted inter alia in decreased invasion and intravasation of wild-type tumor cells (see also Mazzone et al., 2009). A recent study by Chan et al. (2009) takes the obverse approach, focusing on tumor cells with shRNA-mediated decreases in PHD2 expression, injected into wild-type (immunocompromised) hosts. The loss of PHD2 in malignant cells alone appears to accelerate tumor growth and is associated with an induction of angiogenesis and a recruitment of bone marrow-derived cells. The vascular changes observed by Chan et al. due to the loss of PHD2 are shown to be HIF-independent. It appears that the loss of PHD2 in tumors in the Chan et al. (2009) study increases vascular density, whereas the present findings show no significant change in vessel density.

To evaluate whether endothelial phalanx cells overcome the loss of PHD2 in tumor cells, PHD2+/− mice were crossed with MMTV-PyMT+/− mice. The latter strain is a mouse strain spontaneously developing breast cancers that is a reliable model for human disease (polyoma middle T oncoprotein mouse breast cancer model, Lin et al., 2003). It was found that PHD2 haplodeficiency does not alter tumor weight in this spontaneous tumor model (FIG. 26A), while PHD2 haplodeficiency did reduce intratumoral hypoxia (PIMO+ area: 16.4±3.8% in WT PyMT+/− mice vs. 0.5±0.4% in PHD2+/−PyMT+/− mice, P<0.01; data not shown). Thus, the beneficial effects seen by systemic loss of PHD2 can be recapitulated, while the potential tumor growth due to loss of tumoral PHD2 is not seen, again confirming robustness of systemic or endothelial PHD2 inhibition (as compared to tumoral inhibition).

Figure 26:
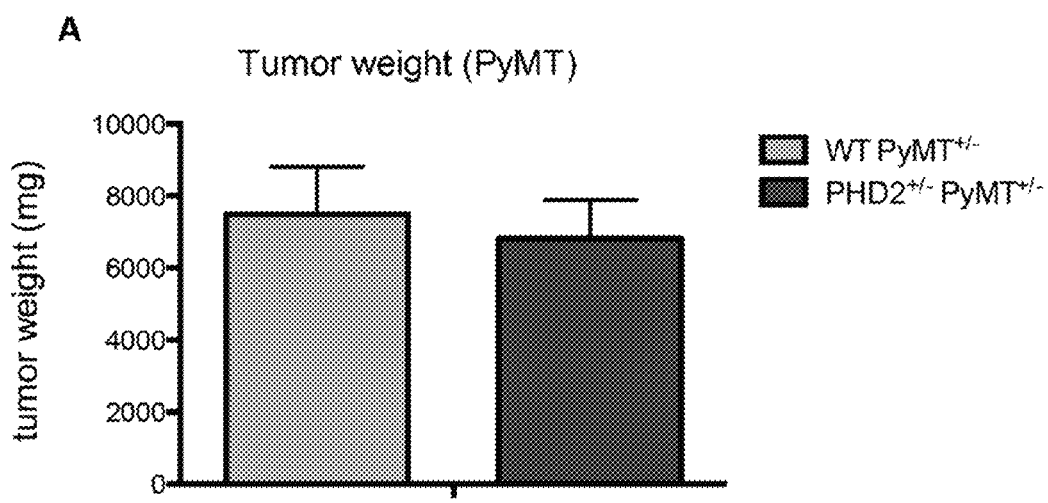
FIG. 26: TUMOR WEIGHT AND METASTASIS IN A SPONTANEOUS MOUSE BREAST CANCER MODEL. A, Tumor weight in WT PyMT+/− and PHD2+/− PyMT+/− mice; B, Tumor metastasis in WT PyMT+/− (left panel) and PHD2+/− PyMT+/− mice (right panel). Both metastatic index and metastasis are significantly reduced (P<0.01 and P=0.05, respectively).
Figure 26:
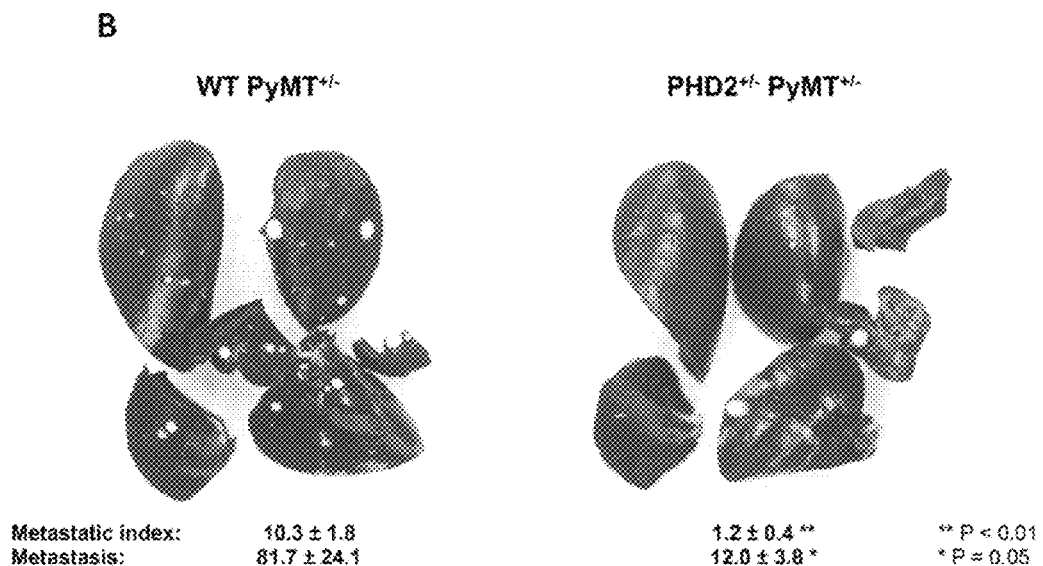

Most notably, PHD2 haplodeficiency in both tumor and stromal cells still reduces metastatic incidence, as evidenced by India ink staining. The absolute number of metastases is decreased from 81.7±24.1 in WT PyMT+/− mice to 12.0±3.8 in PHD2+/− PyMT+/− mice (P=0.05), while the metastatic index (i.e. the number of metastastes/tumor weight) is 10.3±1.8 and 1.2±0.4, respectively (P<0.01) (FIG. 26B). These data show that PHD2 inhibition significantly reduces metastasis, regardless whether PHD2 is also inhibited in the tumor or not. Again, this can be explained by the reduction in hypoxia seen with PHD2 inhibition, as hypoxia is known to increase the risk of metastasis.

Example 10

CNV Assay of EC-Specific PHD2+/− Mice

To assess whether PHD2 also mediates vessel normalization in other disorders linked to inappropriate angiogenesis such as age-related macular degeneration, a choroidal neovascularization (CNV) assay was performed.

Figure 20:
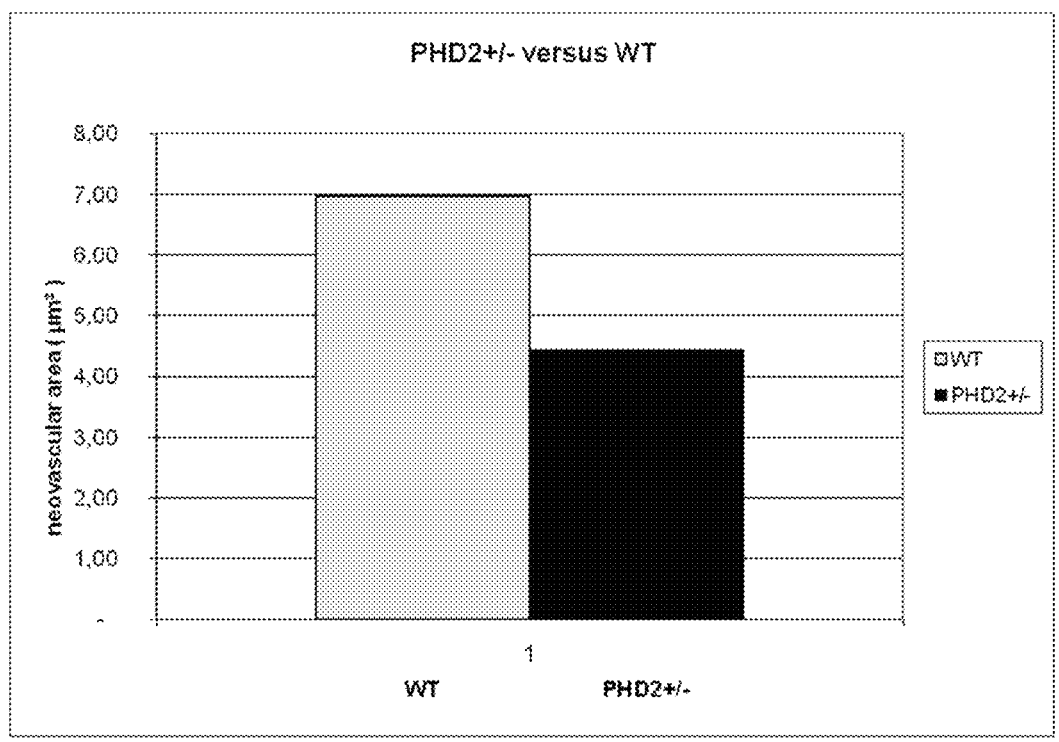
FIG. 20: CNV ASSAY IN WT AND PHD2+/− MICE. Upon inducing a lesion and quantifying neovascularization, the neoformed vessels invade the retina less in endothelial-specific PHD2 haplodeficient mice. 6 mice were used in each group.

C57BL/6 mice were anesthetized with Natrii Pentobarbitalum (Nembutal™ 1/10; Ceva Sante Animale) and the pupils were dilated with Tropicamide (Tropicol™, Thea). Three laser burns were placed with a 532 nm green Argon laser at 9, 12, and 3 o'clock positions around the optic disk using a slit lamp delivery system with a hand-held cover slide as a contact lens and Genteal Gel™ (Novartis, Belgium). Each spot was placed with a spot size of 50 μm, laser duration of 50 milliseconds and a power of 400 mW. A bubble production as a sign for the rupture of the Bruchs membrane was necessary for including the spot. After 14 days, the choroidal neovascularization is quantified within the lesion by FITC-dextran injection (2,000 KDa). The neoformed vessels invade the retina layer and damage the photoreceptors thus inducing loss of vision. Results are shown in FIG. 20. This shows that inhibition of PHD2 may counter excessive vessel growth (neovascularization). This finding could benefit patients with (CNV in) age-related macular degeneration (AMD), which is the chief cause of irreversible loss of vision in elderly patients in the western hemisphere.

Cornea Pocket Assay

We also performed cornea pocket assays and implanted pellets, containing VEGF or FGF-2, in endothelial PHD2Cre/+ mice. In response to VEGF, neovessels display signs of vessel abnormalization (but not as severe as in tumors), such as an increase in vessel tortuosity, architectural disorganization of the vascular network and increased leakiness (assayed by infusion of low molecular weight FITC-dextran, that is capable of extravasating through a leaky endothelial layer). Also in this model, vessel area and number of vascular branching points were comparable in PHD2lox/+ and PHD2Cre/+ mice (vessel area: 27.7±2.3% in PHD2lox/+ versus 23.2±1.6% in PHD2Cre/+, N=4, P=0.15; branching points per mm2: 387±52 in PHD2lox/+ versus 345±60 in PHD2Cre/+, N=4, P=0.64; FIG. 20A,B). However, the architecture of the neovascular network was less complex and showed fewer signs of leakiness in PHD2Cre/+ mice, at least when neovessels were induced by VEGF.

By contrast, the neovascularization response to FGF-2 was comparable in both genotypes, even though FGF-2 did not induce vascular leakiness (vessel area: 39.7 f 2.3% in PHD2lox/+ versus 33.4±4% in PHD2Cre/+, N=4, P=0.23; branching points per mm2: 511±48 in PHD2lox/+ versus 580±87 in PHD2Cre/+, N=4, P=0.55).

All together, haplodeficiency of PHD2 does not affect physiological vessel morphogenesis in development and health, presumably because these vessels form already in a more normalized manner. However, in the cornea pocket assay, vessel formation is induced in an artificial context by administering a high, non-physiological amount of VEGF in an ectopic location (that is otherwise avascular). We speculate that these neovessels therefore show some signs of "abnormalization". In such conditions, haplodeficiency of PHD2 counteracts vessel abnormalization. Consistent with our other analysis in cultured endothelial cells, the response to FGF-2 is not regulated by PHD2.

Example 11

Targeting PHD2 in Ischemic Diseases

Apart from its usefulness in disorders characterized by excessive angiogenesis, such as cancer and AMD, experiments demonstrate that PHD2 inhibition may be useful in the treatment of ischemia, i.e. in conditions where a restriction in blood supply exists. Although at first sight this may appear contradictory, the examples above show that heterozygous deficiency of PHD2 results in mature and more stable pathological vessels. It is thus not illogical to assume that the formation of more stable and more mature vessels would be beneficial in ischemic conditions. This was evaluated in a limb ischemia model after femoral artery ligation in WT and PHD2+/− mice. To induce limb ischemia, the right femoral artery was occluded distal to the branch site of the deep femoral and the popliteal artery. After 1 or 3 or 14 days, mice were perfused with fixative and bismuth-gelatin contrast medium for angiography. Collaterals in the adductor muscle were used for morphometry. Further details on the protocol can be found in Carmeliet et al., 2001; Luttun et al., 2002; Aragones et al., 2008 or Reiss et al., 2007.

Figure 27:
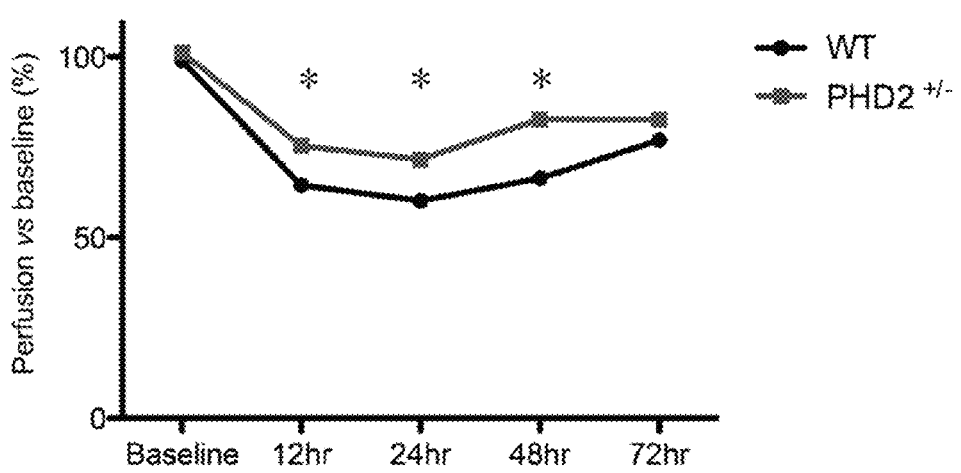
FIG. 27: LIMB PERFUSION IS HIGHER IN PHD2+/− MICE UPON ISCHEMIA. A, Limb perfusion versus baseline at different time points after femoral artery ligation in WT and PHD2 heterozygous mice as evaluated by Laser Doppler Analysis; B, hypoxia in soleus muscle in WT and PHD2 heterozygous mice as evaluated by pimonidazole staining; C, treadmill running test showing improved endurance early after femoral artery ligation in PHD2+/− mice compared to WT mice. Asterisks in A-C denote statistical significance.
Figure 27:
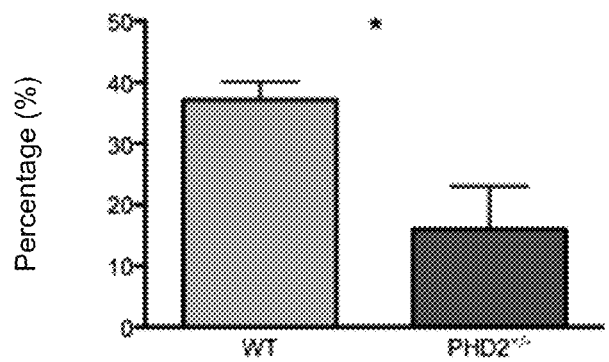
Figure 27:
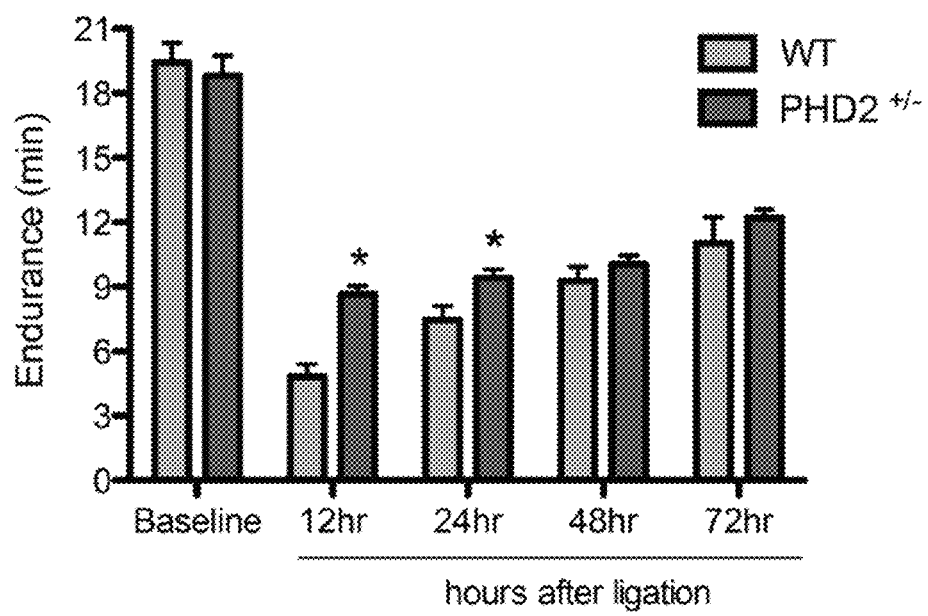

First of all, partial loss of PHD2 improves limb perfusion upon ischemia, as evaluated by laser Doppler analysis (FIG. 27A). It was then assessed whether the increased perfusion also results in better tissue oxygenation, as ischemia is typically associated with hypoxia. Using MRI fluorocarbon oxymetry, it could be shown that the oxygen tension in a ligated limb vs control is considerably higher in PHD2+/− mice vs. WT mice (54±5% vs. 34±3%, respectively, 12 hours after femoral artery occlusion)(data not shown), thus indicating that partial loss of PHD2 improves limb oxygenation upon ischemia. Partial loss of PHD2 also prevents muscle hypoxia (area of PIMO staining: 37.1±3.0% in WT mice, 16.0±7.0% in PHD2+/− mice 12 hours after femoral artery occlusion; FIG. 27B) and attenuates oxidative stress (area of 8-OHdG staining: 46±4% in WT mice, 27±3% in PHD2+/− mice 12 hours after femoral artery occlusion; data not shown). Also, 72 hours after femoral artery occlusion, muscle fibers of PHD2+/− mice were considerably better protected against ischemic necrosis than those of WT controls: 9.1±2.4% necrotic area and 19.2±1.1% necrotic area, respectively. This effect is also seen on the functional level: partial loss of PHD2 improves endurance early after femoral artery occlusion, as evidenced by a treadmill running test (FIG. 27C).

Figure 28:
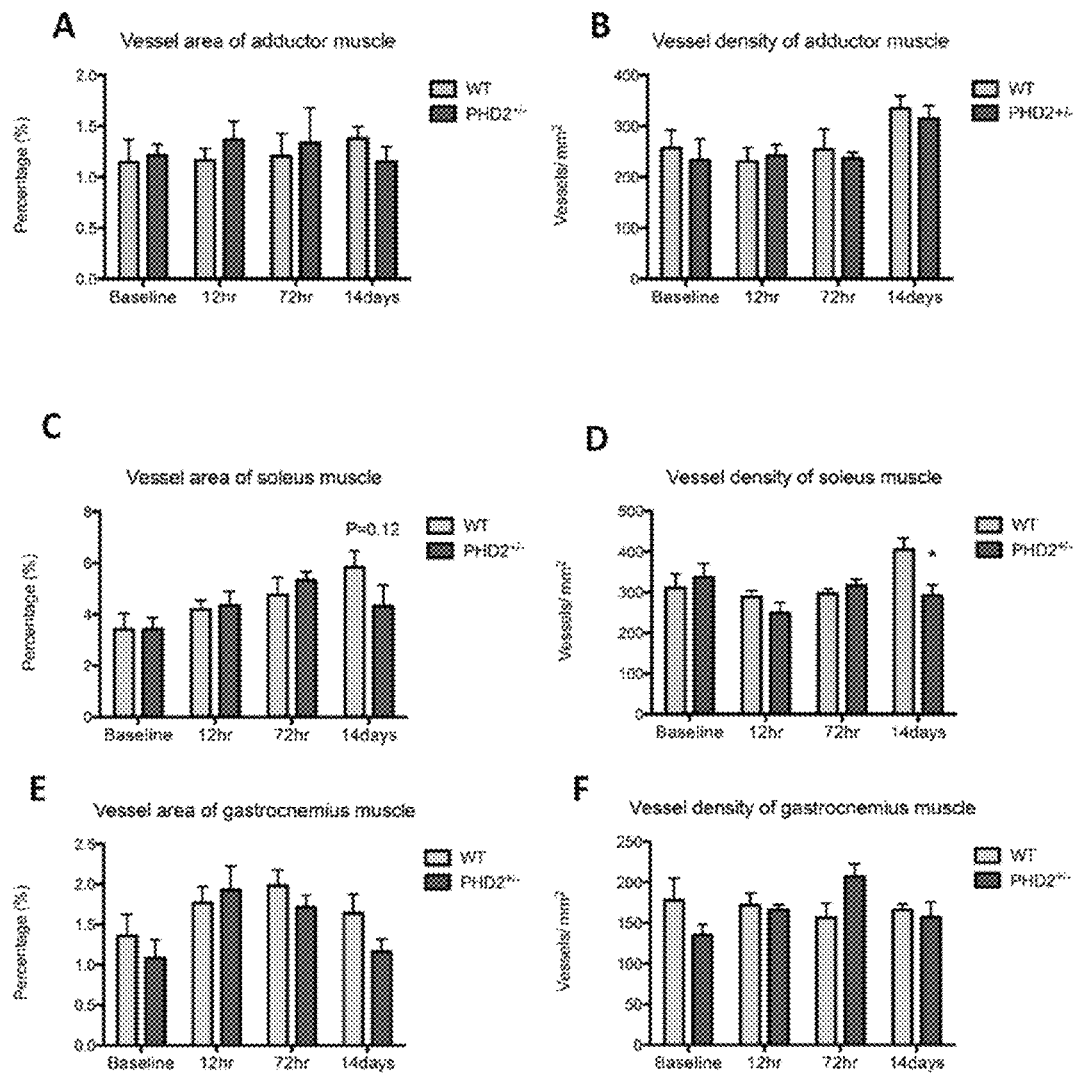
FIG. 28: VESSEL AREA AND DENSITY UPON INDUCTION OF ISCHEMIA. No significant differences exist in vessel area or density either at baseline or at different time points after femoral artery ligation in adductor muscle (A, B), soleus muscle (C, D) or gastrocnemius muscle (E, F).
Figure 29:
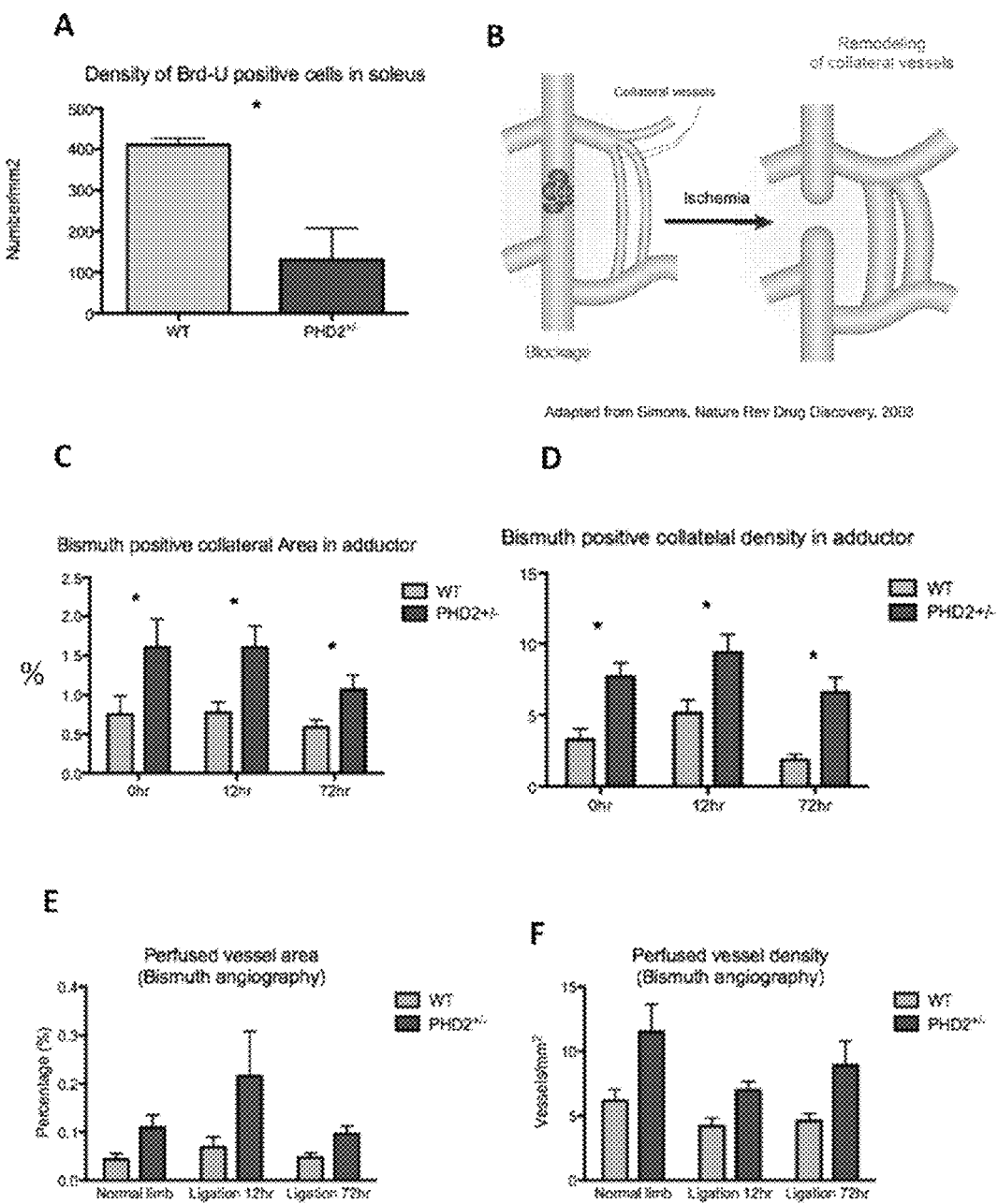
FIG. 29: DECREASED PROLIFERATION BUT INCREASED PERFUSION IN PHD2+/− MICE UPON ISCHEMIA A, Proliferation in soleus muscle in WT and PHD2 heterozygous mice as evaluated by Brd-U staining; B, Proposed mechanism by which maturation of pre-existing collateral vessels may redirect the flow to the ischemic tissue in PHD2+/− mice (adapted from Simons et al., 2003); C, D, perfused collateral area (C) and perfused collateral density (D) in adductor muscle of WT and PHD2 heterozygous mice as evaluated by bismuth angiography at baseline and different time points after ligation; E, F, perfused collateral area (E) and perfused collateral density (F) in soleus muscle of WT and PHD2 heterozygous mice as evaluated by bismuth angiography at baseline and different time points after ligation; G, Micro-CT scan of thigh and calf of WT and PHD2 heterozygous mice, showing number of perfused vessels (absolute numbers included at bottom of figure); H, number of perfused second (top) and third (bottom) generation collateral per first generation collateral in the adductor muscle of WT and PHD2 heterozygous mice as evaluated by bismuth angiography at baseline and different time points after ligation; I, number of perfused second (top) and third (bottom) generation collateral per first generation collateral in the adductor muscle of WT and endothelial specific (Tie2:Cre) PHD2 heterozygous mice as evaluated by bismuth angiography at baseline and after ligation. Asterisk in A, C, D, H, I denotes statistical significance.
Figure 29:
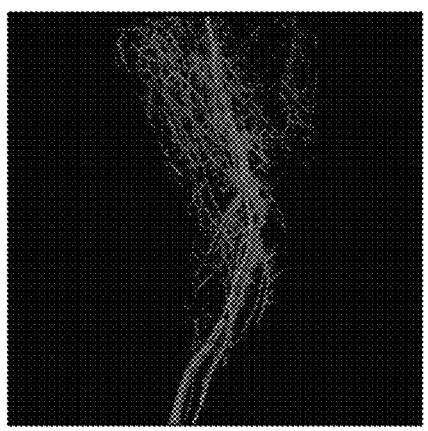
Figure 29:
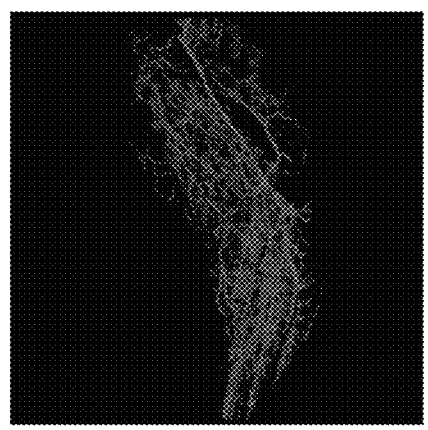
Figure 29:
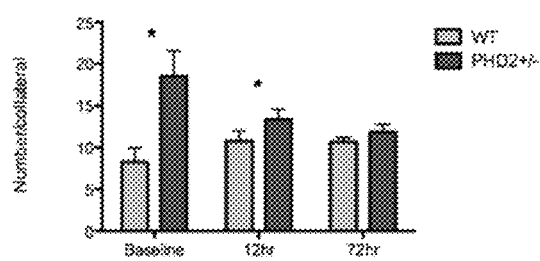
Figure 29:
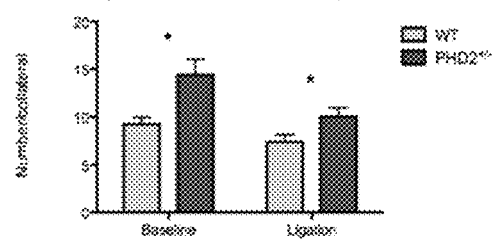
Figure 29:
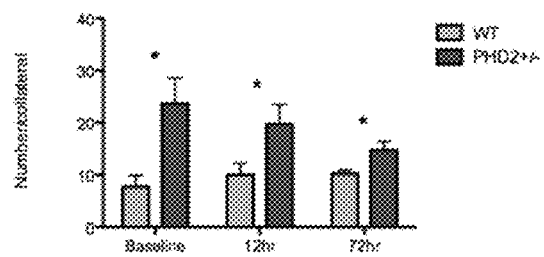
Figure 29:
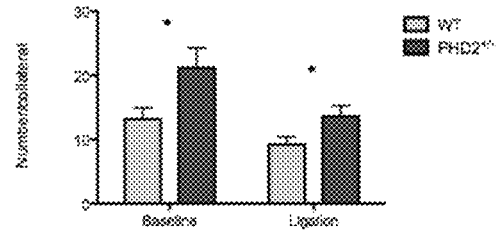

To assess how heterozygous deficiency of PHD2 prevents tissue ischemia, further experiments were performed. PHD2 does not affect the number of CD31 positive capillaries in the adductor, as can be seen from both the comparable vessel area and vessel density observed in adductor muscle of PHD2+/− and WT mice (FIG. 28A,B). The same is true for CD31 positive capillaries in the lower limb, e.g., in the soleus and gastrocnemius muscle (FIG. 28C-F). Also, PHD2 haplodeficient muscles do not encounter tissue regeneration as evaluated by BrdU staining (a proliferation marker) 72 hours after femoral artery occlusion (BrdU positive cells/$\mu m^2$: 410.5±16.3 in muscle of WT mice vs. 130.2±77.3 in muscle of PHD2+/− mice; FIG. 29A). These results indicate that no new blood vessels are formed (i.e., no angiogenesis takes place). The observed increased perfusion can be explained by the remodeling of (pre-existing) collateral vessels; these collateral vessels redirect the flow to the ischemic tissue (FIG. 29B). Indeed, partial loss of PHD2 results in enhanced functional collateralization. While there is no difference in the number of vessels, the number of functional (perfused) vessels is increased upon partial PHD2 inhibition. This can be assessed using bismuth angiography, which visualizes functional vessels only (as opposed to the endothelial marker CD31). Both the bismuth positive collateral area and the vessel density of bismuth positive vessels is markedly higher in adductor (FIG. 29C,D) and soleus muscle (FIG. 29E,F). Micro-CT analysis also reveals that the perfused vessel number is higher in PHD2+/− mice compared to WT mice (FIG. 29G). Not only the 1st generation collaterals are better perfused, but there is also an increase in the number of functional 2nd and 3rd generation collaterals (FIG. 29H). As this is an increase in the number of perfused vessels, but not in the number of vessels per se, the difference is due to increased maturation (widening) of existing vessels. In other words, the collaterals are more stable and allow better perfusion.

To again confirm that these findings are an endothelial effect, an endothelial-specific experiment was set up. Partial deletion of PHD2 by a Tie2: Cre mouse line indeed enhances collateral perfusion, as seen by bismuth angiography of 2nd and 3rd generation collaterals (FIG. 29I).

Figure 30:
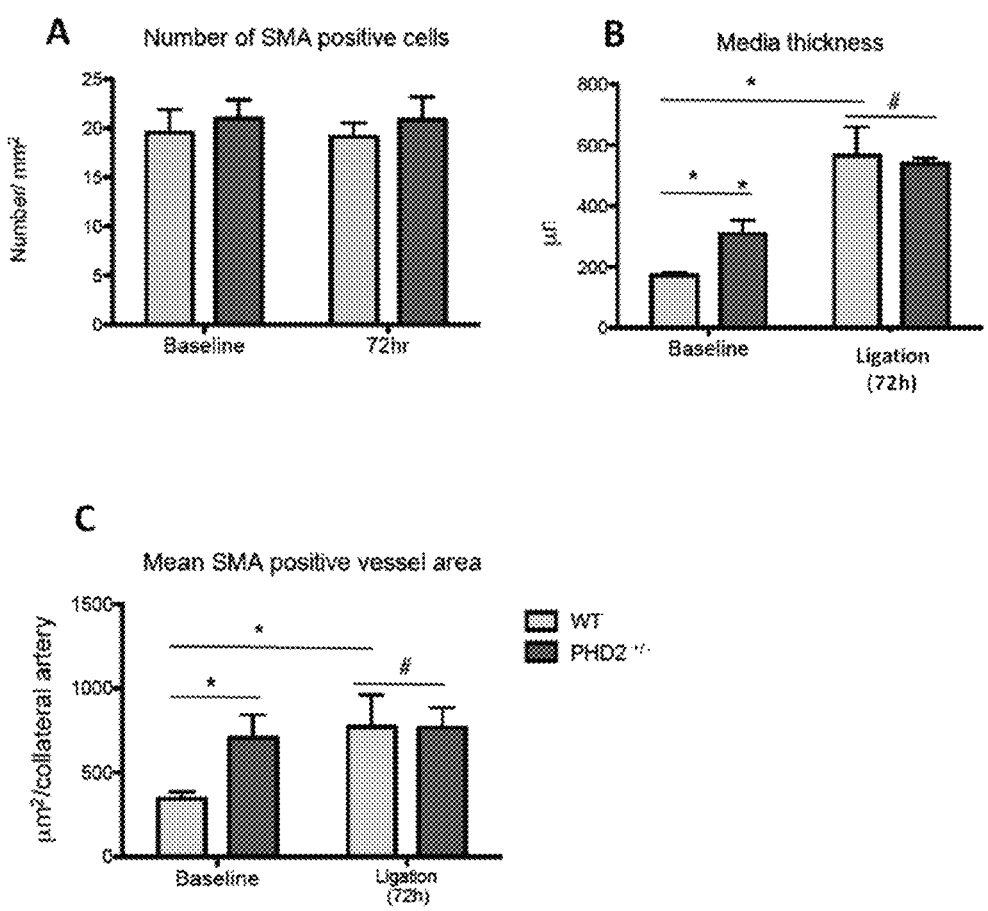
FIG. 30: SMOOTH MUSCLE RECRUITMENT INDICATES REMODELING OF COLLATERALS IN PHD2+/− MICE. A, number of smooth muscle actin (SMA) positive cells in WT and PHD2 heterozygous mice at baseline and after femoral artery ligation; B, intima media thickness in WT and PHD2 heterozygous mice at baseline and after femoral artery ligation; C, mean area covered by SMA positive cells in WT and PHD2 heterozygous mice at baseline and after femoral artery ligation. Asterisk in B, C denotes statistical significance.

Thus, all these experiments confirm that partial loss of PHD2 results in enhanced collateralization through remodeling of collaterals rather than creation of new capillaries. As collateral remodeling is an arteriogenic process, relying on recruitment of smooth muscle cells, smooth muscle parameters were also studied between PHD2+/− and WT mice. Whereas the number of SMA positive cells did not differ, PHD2+/− mice show a higher SMA positive vessel area before ligation (FIG. 30A,C). Also, the intima-media thickness of PHD2+/− mice is higher at baseline (FIG. 30B). All of these parameters are comparable between WT and PHD2+/− mice 72 hours after ligation. This experiment shows that PHD2 haplodeficiency indeed promotes collateral vessel remodeling by increased maturation. Also, it shows that PHD2 inhibition before an ischemic event may be particularly useful, e.g., in the case of ischemia-reperfusion injury. Indeed, ischemia is a common problem in surgery, thus prevention of ischemia by prior inhibition of PHD2 can certainly be envisaged.

In conclusion, these data show that the vascular normalization findings associated with PHD2 inhibition can be widely extrapolated, as PHD2 inhibition shows promising results both in tumor and macular degeneration models (where excessive angiogenesis is undesired) and in ischemia models (where a lack of angiogenesis is unwanted). It also shows that the vessel normalization strategy cannot simply be classified as a pro- or anti-angiogenic strategy, it is rather a form of therapeutic angiogenesis that corrects malshaped endothelial cells.

Note that although "therapeutic angiogenesis" is the term generally used in the art to indicate remodeling of blood vessels to restore normal oxygenation, it is perhaps more correct to refer to "therapeutic arteriogenesis" in the present case, as it refers to maturation or widening of existing blood vessels rather than the generation of new ones. 'Therapeutic angiogenesis' as used in the art is meant to cover both true angiogenesis (capillary formation) and growth or enlargement of existing vessels (arteriogenesis), see Simons et al., 2003. As used in the present application, "therapeutic angiogenesis" only intends to cover the "therapeutic arteriogenesis" part (both terms are used as synonyms here), i.e. the remodeling of blood vessels to restore normal oxygenation by changing the morphogenesis or shape of the blood vessels, but not their number. Nevertheless, despite the fact that no new blood vessels are formed, "therapeutic arteriogenesis" can also be used to restore disorders where angiogenesis has gone awry.

Conclusions

Therapeutic angiogenesis—or therapeutic arteriogenesis, see comment above—can be used in a plethora of diseases, as suggested by Jain, 2003 and Carmeliet, 2003. Diseases characterized or caused by abnormal or excessive angiogenesis in one or more organs include, but are not limited to, cancer, infectious diseases, autoimmune disorders, vascular malformations (e.g., Tie-2 mutation), DiGeorge syndrome, HHT, cavernous hemangioma, atherosclerosis, transplant arteriopathy, obesity, psoriasis, warts, allergic dermatitis, scar keloids, pyogenic granulomas, blistering disease, Kaposi sarcoma in AIDS patients, persistent hyperplastic vitreous syndrome, diabetic retinopathy, retinopathy of prematurity, choroidal neovascularization, primary pulmonary hypertension, asthma, nasal polyps, inflammatory bowel and periodontal disease, ascites, peritoneal adhesions, endometriosis, uterine bleeding, ovarian cysts, ovarian hyperstimulation, arthritis, synovitis, osteomyelitis, and osteophyte formation (see Table 1 of Carmeliet, 2003).

Diseases characterized or caused by insufficient angiogenesis or vessel regression in one or more organs (and thus typically also accompanied by ischemia) include, but are not limited to, Alzheimer disease, amyotrophic lateral sclerosis (ALS), diabetic neuropathy, stroke, atherosclerosis, hypertension, diabetes, restenosis, gastric or oral ulcerations, Crohn disease, hair loss, skin purpura, telangiectasia and venous lake formation, pre-eclampsia, menorrhagia, neonatal respiratory distress, pulmonary fibrosis, emphysema, nephropathy, osteoporosis, and impaired bone fracture healing (see Table 2 of Carmeliet, 2003).

It is envisaged that inhibition of PHD2 may be a therapeutic strategy that can help in any of the above-listed diseases, directly (by normalizing the vasculature) and/or indirectly (by allowing other drugs to reach the target site or tissue). Additionally, it may be used in tissue engineering or vascular remodeling; or indeed in any condition in which endothelial normalization is desired.

Experiments were performed with PHD2 heterozygous deficient mice, which would suggest that partial inhibition of PHD2, e.g., 50% inhibition, is particularly envisaged as therapeutic strategy. Nevertheless, it should be stressed that any inhibition of PHD2 will likely yield (at least some) positive effects, so at least 10%, at least 20% at least 25%, at least 30%, at least 40% inhibition of PHD2 is also envisaged. Note that PHD2 inhibition is part of an amplification loop: PHD2 downregulation leads to better oxygenation; since transcription of PHD2 is regulated by oxygen levels, oxygen-dependent downregulation of PHD2 will result in higher inhibition of PHD2 (see also FIG. 9G). Thus, inhibition of PHD2 of (either at least or up to) 60%, 70%, 75%, 80%, 90%, 95% and even 100% is also particularly envisaged.

TABLE S1

HEMATOLOGICAL PARAMETERS OF PHD2+/− MICE

| | FEMALES | | MALES | |
| --- | --- | --- | --- | --- |
| | WT | PHD2+/− | WT | PHD2+/− |
| WBC (K/μl) | 4.8 ± 0.6 | 5.1 ± 0.6 | 4.3 ± 0.6 | 4.2 ± 0.6 |
| RBC (M/μl) | 7.0 ± 0.1 | 7.5 ± 0.1* | 7.4 ± 0.1 | 7.8 ± 0.1* |
| HGB (g/dl) | 11.5 ± 0.2 | 12.5 ± 0.1* | 11.8 ± 0.2 | 12.8 ± 0.2* |
| HCT (%) | 51.1 ± 1.1 | 55.9 ± 0.5* | 54.7 ± 0.9 | 59.3 ± 1.7* |
| MCHC (G/dl) | 22.2 ± 0.4 | 22.3 ± 0.1 | 21.6 ± 0.3 | 21.7 ± 0.3 |
| PLT (K/μl) | 195 ± 56 | 181 ± 55 | 337 ± 99 | 338 ± 121 |

The data represent hematological parameters (mean ± SEM) in WT and PHD2+/− mice grouped by gender (N = 16-19 per group).

Abbreviations:

white blood cell (WBC), red blood cell count (RBC), hemoglobin (HGB), hematocrit (HCT), mean cell hemoglobin concentration (MCHC), and platelet count (PLT).

*P < 0.05.

TABLE S2

LIST OF PRIMERS, USED FOR RT-PCR

| GENE | PROBE | FORWARD | REVERSE |
|------|-------|---------|---------|
| ANG-1 | AAG-CAA-CAA-CTG-GAC-CTC-ATG-GAC-ACA-GT (SEQ ID NO: 1) | CAA-CAA-CAA-CGCAT-CCT-GCA (SEQ ID NO: 2) | TGC-AAA-GGC-TGACAA-GGT-TAT-G (SEQ ID NO:3) |
| COX2 | TCA-TGA-GCA-GTC-CCCTCC-CTA-GGA-CTT-AA (SEQ ID NO: 4) | TTT-CAT-CTG-AAGACG-GTC-CTC-CA (SEQ ID NO: 5) | GGC-CTG-GGA-TGGCAT-CA (SEQ ID NO:6) |
| EGFR | AGC-AAC-AAT-TCC-ACT-GTGGCT-TGC-ATT (SEQ ID NO: 7) | CCT-CCT-GAG-TTCTCT-GAG-TGC-AAC (SEQ ID NO: 8) | CAC-GGC-AGC-TCCCAT-TTC-TA (SEQ ID NO: 9) |
| ENOS | ACT-ATA-ACT-CCA-TCA-AAA-GGA-GTG-GCT-CCC-AG (SEQ ID NO: 10) | AGC-CCG-GGA-CTTCAT-CAA-TC (SEQ ID NO: 11) | TGA-AGC-CGC-TGCTCA-TGA-G (SEQ ID NO: 12) |
| N-CADHERIN | TCT-GTA-TGC-CGC-ATT-CCA-GGC-CG (SEQ ID NO: 13) | GGA-CGT-CAT-TGTAGC-CAA-CCT-AA (SEQ ID NO: 14) | CCT-GTA-GGG-TCTCCA-CCA-CTG-A (SEQ ID NO: 15) |
| PDGF-B | CCC-ATC-TTC-AAG-AAG-GCC-ACA-GTG-ACC-T (SEQ ID NO: 16) | CGG-TCC-AGG-TGA-GAA-AGA-TTG (SEQ ID NO: 17) | CGT-CTT-GGC-TCGCTG-CTC (SEQ ID NO:18) |
| PFK | ACC-CGT-GGC-TCT-CGTCTC-AAC-ATC-A (SEQ ID NO: 19) | GCC-GGC-TCA-GTGAGA-CAA-G (SEQ ID NO: 20) | TGG-CAC-CTT-TCAGCA-ACA-ATG (SEQ ID NO: 21) |
| PHD2 | ACG-AAA-GCC-ATG-GTTGCT-TGT-TAC-CCA (SEQ ID NO: 22) | GCT-GGG-CAA-CTACAG-GAT-AAA-C (SEQ ID NO: 23) | CAT-AGC-CTG-TTCGTT-GCC-T (SEQ ID NO: 24) |
| ROBO4 | CAC-GAC-TGC-CAG-GCTCCT-ATT-GTG-TG (SEQ ID NO: 25) | ACA-GAC-CCA-GCTGGA-GAT-CG (SEQ ID NO: 26) | TCC-AGT-GAC-TGCAGC-CAC-TT (SEQ ID NO: 27) |
| SFLT1 | TTT-GCC-GCA-GTG-CTCACC-TCT-AAC-G (SEQ ID NO: 28) | GAA-GAC-ATC-CTTCGG-AAG-CAC-GAA (SEQ ID NO: 29) | TTG-GAG-ATC-CGAGAG-AAA-ATG-G (SEQ ID NO: 30) |
| TIE-2 | TGC-CTC-CTA-AGC-TAA-CAATCT-CCC-AGA-GCA-ATA (SEQ ID NO: 31) | AAC-CAA-CAG-TGATGT-CTG-GTC-CTA-T (SEQ ID NO: 32) | GCA-CGT-CAT-GCCGCA-GTA (SEQ ID NO: 33) |
| UNC5B | CCA-TTC-CCC-AGG-GCAAGT-TCT-ATG-ACC (SEQ ID NO: 34) | AGC-CTG-TTG-GTACCA-AAT-GGA (SEQ ID NO: 35) | TTT-CGG-CCT-TGTTGA-TAT-GTA-GAT-AC (SEQ ID NO: 36) |
| UPA | TGC-TGT-CTA-GAG-CCCAGC-GGC-A (SEQ ID NO: 37) | CCG-CTG-CAG-TCACCG-AA (SEQ ID NO: 38) | GCC-AGC-CAG-ACT-TTC-ATG-GT (SEQ ID NO: 39) |
| VEGFR-3 | CGG-CGA-GCC-CCA-CTTGTC-CA (SEQ ID NO: 40) | GGT-TCC-TGA-TGGGCA-AAG-G (SEQ ID NO: 41) | TCA-GTG-GGC-TCAGCC-ATA-GG (SEQ ID NO: 42) |

For the following genes with sequence ID (enclosed between brackets), commercially available primers were ordered from Applied Biosystems: alpha-5 (MM00434506_m1), alpha-V (MM00439797_m1), angiomotin (MM00462731_m1), β-actin (MM00607939-s1), CXCR4 (MM01292123_m1), Dll4 (MM00444619_m1), E-cadherin (MM00486906_m1), FOXO-1 (MM00490672_m1), GLUT-1 (MM00441473_m1), Hes-1 (MM00468601_m1), Hey-1 (MM00468865_m1), Hey-2 (MM00469280_m1), HGFR (MM00434924_m1), IGF1R (MM00802831_m1), Jagged-1 (MM00496902 ml), LOX (MM00495386_m1), MMP2 (MM00439506_m1), MMP9 (MM00442991_m1), Notch-1 (MM00435245_m1), Notch-2 (MM00803077_m1), Notch-4 (MM00440510_m1), Npn-1 (MM01253210_m1), Nrarp (MM00482529_m1), PDK1 (MM00554306_m1), PDK4 (MM00443325_m1), PlGF (MM00435613_m1), Rgs5 (MM00501393_m1), Sirt-1 (MM00490758 ml), TSP-1 (MM01335418_m1), VE-cadherin (MM00486938_M1), VEGF-A (MM00437306_m1), VEGF-B (MM00442102_m1), mFlt1 (MM01210866_m1) and VEGFR-2 (MM01222419_m1).

REFERENCES

Aase, K., Ernkvist, M., Ebarasi, L., Jakobsson, L., Majumdar, A., Yi, C., Birot, O., Ming, Y., Kvanta, A., Edholm, D., et al. (2007). Angiomotin regulates endothelial cell migration during embryonic angiogenesis. Genes Dev 21, 2055-2068.

Appelhoff, R. J., Tian, Y. M., Raval, R. R., Turley, H., Harris, A. L., Pugh, C. W., Ratcliffe, P. J., and Gleadle, J. M. (2004). Differential function of the prolyl hydroxylases PHD1, PHD2, and PHD3 in the regulation of hypoxia-inducible factor. J Biol Chem 279, 38458-38465.

Aragones, J., Schneider, M., Van Geyte, K., Fraisl, P., Dresselaers, T., Mazzone, M., Dirkx, R., Zacchigna, S., Lemieux, H., Jeoung, N. H., et al. (2008). Deficiency or inhibition of oxygen sensor Phd1 induces hypoxia tolerance by reprogramming basal metabolism. Nat Genet. 40, 170-180.

Baluk, P., Hashizume, H., and McDonald, D. M. (2005). Cellular abnormalities of blood vessels as targets in cancer. Current opinion in genetics & development 15, 102-111.

Bergers, G., and Hanahan, D. (2008). Modes of resistance to anti-angiogenic therapy. Nat Rev Cancer 8, 592-603.

Boucher, Y., and Jain, R. K. (1992). Microvascular pressure is the principal driving force for interstitial hypertension in solid tumors: implications for vascular collapse. Cancer Res 52, 5110-5114.

Carmeliet, P., Lampugnani, M. G., Moons, L., Breviario, F., Compernolle, V., Bono, F., Balconi, G., Spagnuolo, R., Oostuyse, B., Dewerchin, M., et al. (1999). Targeted deficiency or cytosolic truncation of the VE-cadherin gene in mice impairs VEGF-mediated endothelial survival and angiogenesis. Cell 98, 147-157.

Carmeliet P, Moons L, Luttun A, Vincenti V, Compernolle V, De Mol M, Wu Y, Bono F, Devy L, Beck H, Scholz D, Acker T, DiPalma T, Dewerchin M, Noel A, Stalmans I, Barra A, Blacher S, Vandendriessche T, Ponten A, Eriksson U, Plate K H, Foidart J M, Schaper W, Charnock-Jones D S, Hicklin D J, Herbert J M, Collen D, Persico M G. (2001). Synergism between vascular endothelial growth factor and placental growth factor contributes to angiogenesis and plasma extravasation in pathological conditions. Nat. Med.; 7(5):575-83.

Carmeliet P. (2003) Angiogenesis in health and disease. Nat. Med.; 9(6):653-60.

Casanovas, O., Hicklin, D. J., Bergers, G., and Hanahan, D. (2005). Drug resistance by evasion of antiangiogenic targeting of VEGF signaling in late-stage pancreatic islet tumors. Cancer Cell 8, 299-309.

Chan, D. A., Sutphin, P. D., Yen, S. E., and Giaccia, A. J. (2005). Coordinate regulation of the oxygen-dependent degradation domains of hypoxia-inducible factor 1 alpha. Mol Cell Biol 25, 6415-6426.

Chan D A, Kawahara T L, Sutphin P D, Chang H Y, Chi J T, Giaccia A J. (2009). Tumor vasculature is regulated by PHD2-mediated angiogenesis and bone marrow-derived cell recruitment. Cancer Cell.; 15(6):527-38.

Couvelard, A., Deschamps, L., Rebours, V., Sauvanet, A., Gatter, K., Pezzella, F., Ruszniewski, P., and Bedossa, P. (2008). Overexpression of the oxygen sensors PHD-1, PHD-2, PHD-3, and FIH Is associated with tumor aggressiveness in pancreatic endocrine tumors. Clin Cancer Res 14, 6634-6639.

Cramer, T., Yamanishi, Y., Clausen, B. E., Forster, I., Pawlinski, R., Mackman, N., Haase, V. H., Jaenisch, R., Corr, M., Nizet, V., et al. (2003). HIF-1alpha is essential for myeloid cell-mediated inflammation. Cell 112, 645-657.

Dutta, D., Ray, S., Vivian, J. L., and Paul, S. (2008). Activation of the VEGFR1 chromatin domain: An angiogenic signal-ETS1/HIF-2alpha regulatory axis. J Biol. Chem.***

Epstein, A. C., Gleadle, J. M., McNeill, L. A., Hewitson, K. S., O'Rourke, J., Mole, D. R., Mukherji, M., Metzen, E., Wilson, M. I., Dhanda, A., et al. (2001). *C. elegans* EGL-9 and mammalian homologs define a family of dioxygenases that regulate HIF by prolyl hydroxylation. Cell 107, 43-54.

Erler, J. T., Bennewith, K. L., Nicolau, M., Dornhofer, N., Kong, C., Le, Q. T., Chi, J. T., Jeffrey, S. S., and Giaccia, A. J. (2006). Lysyl oxidase is essential for hypoxia-induced metastasis. Nature 440, 1222-1226.

Fenton, B. M., and Paoni, S. F. (2007). The addition of AG-013736 to fractionated radiation improves tumor response without functionally normalizing the tumor vasculature. Cancer Res 67, 9921-9928.

Fischer, C., Jonckx, B., Mazzone, M., Zacchigna, S., Loges, S., Pattarini, L., Chorianopoulos, E., Liesenborghs, L., Koch, M., De Mol, M., et al. (2007). Anti-PlGF inhibits growth of VEGF(R)-inhibitor-resistant tumors without affecting healthy vessels. Cell 131, 463-475.

Forsythe, J. A., Jiang, B. H., Iyer, N. V., Agani, F., Leung, S. W., Koos, R. D., and Semenza, G. L. (1996). Activation of vascular endothelial growth factor gene transcription by hypoxiainducible factor 1. Mol Cell Biol 16, 4604-4613.

Franco, M., Man, S., Chen, L., Emmenegger, U., Shaked, Y., Cheung, A. M., Brown, A. S., Hicklin, D. J., Foster, F. S., and Kerbel, R. S. (2006). Targeted anti-vascular endothelial growth factor receptor-2 therapy leads to short-term and long-term impairment of vascular function and increase in tumor hypoxia. Cancer Res 66, 3639-3648.

Gao, D., Nolan, D. J., Mellick, A. S., Bambino, K., McDonnell, K., and Mittal, V. (2008). Endothelial progenitor cells control the angiogenic switch in mouse lung metastasis. Science (New York, N.Y. 319, 195-198.

Gatenby, R. A., and Gillies, R. J. (2004). Why do cancers have high aerobic glycolysis? Nat Rev Cancer 4, 891-899.

Gerhardt, H., Golding, M., Fruttiger, M., Ruhrberg, C., Lundkvist, A., Abramsson, A., Jeltsch, M., Mitchell, C., Alitalo, K., Shima, D., et al. (2003). VEGF guides angiogenic sprouting utilizing endothelial tip cell filopodia. J Cell Biol 161, 1163-1177.

Gerhardt, H., Ruhrberg, C., Abramsson, A., Fujisawa, H., Shima, D., and Betsholtz, C. (2004). Neuropilin-1 is required for endothelial tip cell guidance in the developing central nervous system. Dev Dyn 231, 503-509.

Gerhardt, H., and Semb, H. (2008). Pericytes: gatekeepers in tumour cell metastasis? Journal of molecular medicine (Berlin, Germany) 86, 135-144.

Ginouvès A, Ilc K, Macias N, Pouysségur J, Berra E. (2008). PHDs overactivation during chronic hypoxia "desensitizes" HIFalpha and protects cells from necrosis. Proc Natl Acad Sci USA. 105(12):4745-50.

Grazia Lampugnani, M., Zanetti, A., Corada, M., Takahashi, T., Balconi, G., Breviario, F., Orsenigo, F., Cattelino, A., Kemler, R., Daniel, T. O., et al. (2003). Contact inhibition of VEGF-induced proliferation requires vascular endothelial cadherin, beta-catenin, and the phosphatase DEP-1/CD148. J Cell Biol 161, 793-804.

Greenberg, J. I., Shields, D. J., Barillas, S. G., Acevedo, L. M., Murphy, E., Huang, J., Scheppke, L., Stockmann, C., Johnson, R. S., Angle, N., et al. (2008). A role for VEGF as a negative regulator of pericyte function and vessel maturation. Nature.***

Hamzah, J., Jugold, M., Kiessling, F., Rigby, P., Manzur, M., Marti, H. H., Rabie, T., Kaden, S., Grone, H. J., Hammerling, G. J., et al. (2008). Vascular normalization in Rgs5-deficient tumours promotes immune destruction. Nature 453, 410-414.

Hellstrom, M., Phng, L. K., Hofmann, J. J., Wallgard, E., Coultas, L., Lindblom, P., Alva, J., Nilsson, A. K., Karlsson, L., Gaiano, N., et al. (2007). Dll4 signalling through Notch1 regulates formation of tip cells during angiogenesis. Nature 445, 776-780.

Jain R K. (2003). Molecular regulation of vessel maturation. Nat. Med. 9(6):685-93.

Jain, R. K. (2005). Normalization of tumor vasculature: an emerging concept in antiangiogenic therapy. Science 307, 58-62.

Jones, C. A., London, N. R., Chen, H., Park, K. W., Sauvaget, D., Stockton, R. A., Wythe, J. D., Suh, W., Larrieu-Lahargue, F., Mukouyama, Y. S., et al. (2008). Robo4 stabilizes the vascular network by inhibiting pathologic angiogenesis and endothelial hyperpermeability. Nat Med 14, 448-453.

Kaelin, W. G., Jr., and Ratcliffe, P. J. (2008). Oxygen sensing by metazoans: the central role of the HIF hydroxylase pathway. Mol Cell 30, 393-402.

Kappas, N. C., Zeng, G., Chappell, J. C., Kearney, J. B., Hazarika, S., Kallianos, K. G., Patterson, C., Annex, B. H., and Bautch, V. L. (2008). The VEGF receptor Flt-1 spatially modulates Flk-1 signaling and blood vessel branching. J Cell Biol 181, 847-858.

Kashiwagi, S., Tsukada, K., Xu, L., Miyazaki, J., Kozin, S. V., Tyrrell, J. A., Sessa, W. C., Gerweck, L. E., Jain, R. K., and Fukumura, D. (2008). Perivascular nitric oxide gradients normalize tumor vasculature. Nat Med 14, 255-257.

Kato, H., Inoue, T., Asanoma, K., Nishimura, C., Matsuda, T., and Wake, N. (2006). Induction of human endometrial cancer cell senescence through modulation of HIF-1alpha activity by EGLN1. Int J Cancer 118, 1144-1153.

Kearney, J. B., Ambler, C. A., Monaco, K. A., Johnson, N., Rapoport, R. G., and Bautch, V. L. (2002). Vascular endothelial growth factor receptor Flt-1 negatively regulates developmental blood vessel formation by modulating endothelial cell division. Blood 99, 2397-2407.

Kitamura, T., Asai, N., Enomoto, A., Maeda, K., Kato, T., Ishida, M., Jiang, P., Watanabe, T., Usukura, J., Kondo, T., et al. (2008). Regulation of VEGF-mediated angiogenesis by the Akt/PKB substrate Girdin. Nat. Cell Biol 10, 329-337.

Kuhlencordt, P. J., Rosel, E., Gersztern, R. E., Morales-Ruiz, M., Dombkowski, D., Atkinson, W. J., Han, F., Preffer, F., Rosenzweig, A., Sessa, W. C., et al. (2004). Role of endothelial nitric oxide synthase in endothelial activation: insights from eNOS knockout endothelial cells. Am J Physiol Cell Physiol 286, C1195-1202.

Le Bras, A., Lionneton, F., Mattot, V., Lelievre, E., Caetano, B., Spruyt, N., and Soncin, F. (2007). HIF-2alpha specifically activates the VE-cadherin promoter independently of hypoxia and in synergy with Ets-1 through two essential ETS-binding sites. Oncogene 26, 7480-7489.

Lee, K. A., Lynd, J. D., O'Reilly, S., Kiupel, M., McCormick, J. J., and LaPres, J. J. (2008). The biphasic role of the hypoxia-inducible factor prolyl-4-hydroxylase, PHD2, in modulating tumor-forming potential. Mol Cancer Res 6, 829-842.

Lin E Y, Jones J G, Li P, Zhu L, Whitney K D, Muller W J, Pollard J W. (2003). Progression to malignancy in the polyoma middle T oncoprotein mouse breast cancer model provides a reliable model for human diseases. Am. J. Pathol.; 163(5):2113-26.

Lofstedt, T., Fredlund, E., Holmquist-Mengelbier, L., Pietras, A., Ovenberger, M., Poellinger, L., and Pahlman, S. (2007). Hypoxia inducible factor-2alpha in cancer. Cell Cycle 6, 919-926.

Lu, X., Le Noble, F., Yuan, L., Jiang, Q., De Lafarge, B., Sugiyama, D., Breant, C., Claes, F., De Smet, F., Thomas, J. L., et al. (2004). The netrin receptor UNC5B mediates guidance events controlling morphogenesis of the vascular system. Nature 432, 179-186.

Luttun, A., Tjwa, M., Moons, L., Wu, Y., Angelillo-Scherrer A., Liao, F., Nagy, J. A., Hooper, A., Priller, J., De Klerck, B., et al. (2002). Revascularization of ischemic tissues by PlGF treatment, and inhibition of tumor angiogenesis, arthritis and atherosclerosis by anti-Flt1. Nature medicine 8, 831-840.

Marxsen, J. H., Stengel, P., Doege, K., Heikkinen, P., Jokilehto, T., Wagner, T., Jelkmann, W., Jaakkola, P., and Metzen, E. (2004). Hypoxia-inducible factor-1 (HIF-1) promotes its degradation by induction of HIF-alpha-prolyl-4-hydroxylases. The Biochemical journal 381, 761-767.

Mazzone M, Basilico C, Cavassa S, Pennacchietti S, Risio M, Naldini L, Comoglio P M, Michieli P. (2004). An uncleavable form of pro-scatter factor suppresses tumor growth and dissemination in mice. J Clin Invest.; 114(10):1418-32.

Mazzone M, Dettori D, Leite de Oliveira R, Loges S, Schmidt T, Jonckx B, Tian Y M, Lanahan A A, Pollard P, Ruiz de Almodovar C, De Smet F, Vinckier S, Aragonés J, Debackere K, Luttun A, Wyns S, Jordan B, Pisacane A, Gallez B, Lampugnani M G, Dejana E, Simons M, Ratcliffe P, Maxwell P, Carmeliet P. (2009). Heterozygous deficiency of PHD2 restores tumor oxygenation and inhibits metastasis via endothelial normalization. Cell. 6; 136(5):839-51.

McDonald, D. M., and Choyke, P. L. (2003). Imaging of angiogenesis: from microscope to clinic. Nat Med 9, 713-725.

Michieli, P., Mazzone, M., Basilico, C., Cavassa, S., Sottile, A., Naldini, L., and Comoglio, P. M. (2004). Targeting the tumor and its microenvironment by a dual-function decoy Met receptor. Cancer cell 6, 61-73.

Milkiewicz, M., Pugh, C. W., and Egginton, S. (2004). Inhibition of endogenous HIF inactivation induces angiogenesis in ischaemic skeletal muscles of mice. J Physiol 560, 21-26.

Minamishima, Y. A., Moslehi, J., Bardeesy, N., Cullen, D., Bronson, R. T., and Kaelin, W. G., Jr. (2008). Somatic inactivation of the PHD2 prolyl hydroxylase causes polycythemia and congestive heart failure. Blood 111, 3236-3244.

Nangaku, M., Izuhara, Y., Takizawa, S., Yamashita, T., Fujii-Kuriyama, Y., Ohneda, O., Yamamoto, M., van Ypersele de Strihou, C., Hirayama, N., and Miyata, T. (2007). A novel class of prolyl hydroxylase inhibitors induces angiogenesis and exerts organ protection against ischemia. Arterioscler Thromb Vasc Biol 27, 2548-2554.

Noguera-Troise, I., Daly, C., Papadopoulos, N. J., Coetzee, S., Boland, P., Gale, N. W., Lin, H. C., Yancopoulos, G. D., and Thurston, G. (2006). Blockade of Dll4 inhibits tumour growth by promoting non-productive angiogenesis. Nature 444, 1032-1037.

Noll, F. (1981). L-(+)-Lactate. Methods of enzymatic analysis 6, 582-588.

Pan, Y., Mansfield, K. D., Bertozzi, C. C., Rudenko, V., Chan, D. A., Giaccia, A. J., and Simon, M. C. (2007). Multiple factors affecting cellular redox status and energy metabolism modulate hypoxia-inducible factor prolyl hydroxylase activity in vivo and in vitro. Mol Cell Biol 27, 912-925.

Passalidou, E., Stewart, M., Trivella, M., Steers, G., Pillai, G., Dogan, A., Leigh, I., Hatton, C., Harris, A., Gatter, K., et al. (2003). Vascular patterns in reactive lymphoid tissue and in non-Hodgkin's lymphoma. Br J Cancer 88, 553-559.

Peng, J., Zhang, L., Drysdale, L., and Fong, G. H. (2000). The transcription factor EPAS-1/hypoxia-inducible factor 2alpha plays an important role in vascular remodeling. Proc Natl Acad Sci USA 97, 8386-8391.

Pennacchietti, S., Michieli, P., Galluzzo, M., Mazzone, M., Giordano, S., and Comoglio, P. M. (2003). Hypoxia promotes invasive growth by transcriptional activation of the met protooncogene. Cancer Cell 3, 347-361.

Pospisilik, J. A., Knauf, C., Joza, N., Benit, P., Orthofer, M., Cani, P. D., Ebersberger, I., Nakashima, T., Sarao, R., Neely, G., et al. (2007). Targeted deletion of AIF decreases mitochondrial oxidative phosphorylation and protects from obesity and diabetes. Cell 131, 476-491.

Reiss Y, Droste J, Heil M, Tribulova S, Schmidt M H, Schaper W, Dumont D J, Plate K H. (2007). Angiopoietin-2 impairs revascularization after limb ischemia. Circ Res.; 101(1): 88-96.

Rolny, C., Nilsson, I., Magnusson, P., Armulik, A., Jakobsson, L., Wentzel, P., Lindblom, P., Norlin, J., Betsholtz, C., Heuchel, R., et al. (2006). Platelet-derived growth factor receptor-beta promotes early endothelial cell differentiation. Blood 108, 1877-1886.

Semenza, G. L. (2003). Targeting HIF-1 for cancer therapy. Nat Rev Cancer 3, 721-732.

Sheldon, H., Andre, M., Legg, J. A., Heal, P., Herbert, J. M., Sainson, R., Sharma, A. S., Kitajewski, J. K., Heath, V. L., and Bicknell, R. (2008). Active involvement of Robo1 and Robo4 in filopodia formation and endothelial cell motility mediated via WASP and other actin nucleation-promoting factors. Faseb J.

Simons M, Ware J A. (2003). Therapeutic angiogenesis in cardiovascular disease. Nat Rev Drug Discov.; 2(11):863-71.

Sowter, H. M., Raval, R. R., Moore, J. W., Ratcliffe, P. J., and Harris, A. L. (2003). Predominant role of hypoxia-inducible transcription factor (Hif)-1alpha versus Hif-2alpha in regulation of the transcriptional response to hypoxia. Cancer research 63, 6130-6134.

Sterling K A, Tehrani T, Rudnick M R. (2008). Clinical significance and preventive strategies for contrast-induced nephropathy. Curr Opin Nephrol Hypertens. 17(6):616-23.

Stockmann, C., Doedens, A., Weidemann, A., Zhang, N., Takeda, N., Greenberg, J. I., Cheresh, D. A., and Johnson, R. S. (2008). Deletion of vascular endothelial growth factor in myeloid cells accelerates tumorigenesis. Nature.***

Stolze, I. P., Tian, Y. M., Appelhoff, R. J., Turley, H., Wykoff, C. C., Gleadle, J. M., and Ratcliffe, P. J. (2004). Genetic analysis of the role of the asparaginyl hydroxylase factor inhibiting hypoxia-inducible factor (HIF) in regulating HIF transcriptional target genes. The Journal of biological chemistry 279, 42719-42725.

Sullivan, R., and Graham, C. H. (2007). Hypoxia-driven selection of the metastatic phenotype. Cancer Metastasis Rev 26, 319-331.

Taddei, A., Giampietro, C., Conti, A., Orsenigo, F., Breviario, F., Pirazzoli, V., Potente, M., Daly, C., Dimmeler, S., and Dejana, E. (2008). Endothelial adherens junctions control tight junctions by VE-cadherin-mediated upregulation of claudin-5. Nat Cell Biol.***

Takeda, K., Aguila, H. L., Parnell, N. S., Li, X., Lamothe, K., Duan, L. J., Takeda, H., Lee, F. S., and Fong, G. H. (2008). Regulation of adult erythropoiesis by prolyl hydroxylase domain proteins. Blood 111, 3229-3235.

Takeda, K., Cowan, A., and Fong, G. H. (2007). Essential role for prolyl hydroxylase domain protein 2 in oxygen homeostasis of the adult vascular system. Circulation 116, 774-781.

Takeda, K., and Fong, G. H. (2007). Prolyl hydroxylase domain 2 protein suppresses hypoxia-induced endothelial cell proliferation. Hypertension 49, 178-184.

Tammela, T., Zarkada, G., Wallgard, E., Murtomaki, A., Suchting, S., Wirzenius, M., Waltari, M., Hellstrom, M., Schomber, T., Peltonen, R., et al. (2008). Blocking VEGFR-3 suppresses angiogenic sprouting and vascular network formation. Nature.***

Tang, N., Wang, L., Esko, J., Giordano, F. J., Huang, Y., Gerber, H. P., Ferrara, N., and Johnson, R. S. (2004). Loss of HIF-1alpha in endothelial cells disrupts a hypoxia-driven VEGF autocrine loop necessary for tumorigenesis. Cancer cell 6, 485-495.

Teicher, B. A. (1994). Hypoxia and drug resistance. Cancer Metastasis Rev 13, 139-168.

ten Dam M A, Wetzels J F. (2008) Toxicity of contrast media: an update. Neth J. Med. 66(10):416-22.

Vaupel P, Harrison L. (2004). Tumor hypoxia: causative factors, compensatory mechanisms, and cellular response. Oncologist.; 9 Suppl 5:4-9.

Wiesener, M. S., Turley, H., Allen, W. E., Willam, C., Eckardt, K. U., Talks, K. L., Wood, S. M., Gatter, K. C., Harris, A. L., Pugh, C. W., et al. (1998). Induction of endothelial PAS domain protein-1 by hypoxia: characterization and comparison with hypoxia-inducible factor-1alpha. Blood 92, 2260-2268.

Winkler, F., Kozin, S. V., Tong, R. T., Chae, S. S., Booth, M. F., Garkavtsev, I., Xu, L., Hicklin, D. J., Fukumura, D., di Tomaso, E., et al. (2004). Kinetics of vascular normalization by VEGFR2 blockade governs brain tumor response to radiation: role of oxygenation, angiopoietin-1, and matrix metalloproteinases. Cancer Cell 6, 553-563.

Wu, S., Nishiyama, N., Kano, M. R., Morishita, Y., Miyazono, K., Itaka, K., Chung, U. I., and Kataoka, K. (2008). Enhancement of angiogenesis through stabilization of hypoxiainducible factor-1 by silencing prolyl hydroxylase domain-2 gene. Mol Ther 16, 1227-1234.

Xian, X., Hakansson, J., Stahlberg, A., Lindblom, P., Betsholtz, C., Gerhardt, H., and Semb, H. (2006). Pericytes limit tumor cell metastasis. J Clin Invest 116, 642-651.

Yamashita, T., Ohneda, K., Nagano, M., Miyoshi, C., Kaneko, N., Miwa, Y., Yamamoto, M., Ohneda, O., and Fujii-Kuriyama, Y. (2008). HIF-2alpha in endothelial cells regulates tumor neovascularization through activation of ephrin A1. J Biol. Chem.***

The invention claimed is:

1. A method of increasing perfusion in a tissue, the method comprising:

inhibiting PHD2 in tissue in need thereof so as to increase perfusion in the tissue, wherein inhibition of PHD2 is achieved at the DNA or RNA level.

2. The method according to claim 1, wherein the inhibition of PHD2 is partial.

3. The method according to claim 1, wherein the inhibition is specific to endothelial cells.

4. The method according to claim 1, wherein inhibition of PHD2 is utilized in combination with means for causing iatrogenic effects.

5. The method according to claim 4, wherein the iatrogenic effects comprise iatrogenic tissue damage.

6. The method according to claim 5, wherein the means for causing iatrogenic tissue damage is selected from a contrast agent, radiotherapy or chemotherapy.

7. The method according to claim 1, for the treatment of cancer in the tissue.

8. The method according to claim 7, wherein the cancer is metastatic cancer or cancer with an increased risk of metastasis.

9. The method according to claim 4, wherein the means for causing iatrogenic effects is an anti-cancer therapy selected from radiotherapy or chemotherapy.

10. The method according to claim 9, wherein the means for causing iatrogenic effects is chemotherapy comprising treatment with a platinum-based chemotherapeutic drug and/or an anthracycline antibiotic.

11. The method according to claim 1, to treat macular degeneration or ischemia or to induce vascular remodeling.

12. The method according to claim 11, wherein ischemia occurs in limb ischemia, chronic obstructive pulmonary disease, ischemia-reperfusion injury, post-operative ischemia, diabetic ischemic disease, ischemic cardiovascular disease, restenosis, acute myocardial infarction, chronic ischemic heart disease, atherosclerosis, ischemic stroke, ischemic cerebral infarction or ischemic bowel disease.

13. The method according to claim 1, wherein the perfusion is increased due to a change in morphogenesis or shape of blood vessels, but not due to a change in number of vessels.

14. A method of increasing perfusion in a subject, the method comprising:
administering a PHD2 inhibitor to the subject to increase perfusion by changing shape of blood vessels in the subject, wherein inhibition of PHD2 is achieved at the DNA or RNA level.

15. The method according to claim 14, wherein the PHD2 inhibitor is siRNA specific to PHD2.

16. The method according to claim 1, wherein inhibiting PHD2 comprises administering an siRNA specific to PHD2 to the tissue so as to inhibit PHD2 in the tissue and change the subject's blood vessels' morphogenesis or shape, thus increasing perfusion thereof, wherein increased tissue perfusion in the tissue is not due to a change in number of blood vessels.

17. The method according to claim 15, wherein increased tissue perfusion in the subject is not due to a change in number of the subject's blood vessels.

18. The method according to claim 15, wherein the subject is undergoing therapy with cisplatin.

19. The method according to claim 15, wherein the subject is undergoing therapy with doxorubicin.

* * * * *

SEQUENCE LISTING

<160> NUMBER OF SEQ ID NOS: 47

<210> SEQ ID NO 1
<211> LENGTH: 29
<212> TYPE: DNA
<213> ORGANISM: Artificial sequence
<220> FEATURE:
<223> OTHER INFORMATION: Primer

<400> SEQUENCE: 1
aagcaacaac tggacctcat ggacacagt					29

```
<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2
caacaacaac gcatcctgca                                                  20

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
tgcaaaggct gacaaggtta tg                                               22

<210> SEQ ID NO 4
<211> LENGTH: 29
<212> TYPE: DNA
<213> ORGANISM: Artificial sequence
<220> FEATURE:
<223> OTHER INFORMATION: Primer

<400> SEQUENCE: 4
tcatgagcag tccsctccct aggacttaa                                        29

<210> SEQ ID NO 5
<211> LENGTH: 23
<212> TYPE: DNA
<213> ORGANISM: Artificial sequence
<220> FEATURE:
<223> OTHER INFORMATION: Primer

<400> SEQUENCE: 5
tttcatctga agacggtcct cca                                              23

<210> SEQ ID NO 6
<211> LENGTH: 17
<212> TYPE: DNA
<213> ORGANISM: Artificial sequence
<220> FEATURE:
<223> OTHER INFORMATION: Primer

<400> SEQUENCE: 6
ggcctgggat ggcatca                                                     17

<210> SEQ ID NO 7
<211> LENGTH: 27
<212> TYPE: DNA
<213> ORGANISM: Artificial sequence
<220> FEATURE:
<223> OTHER INFORMATION: Primer

<400> SEQUENCE: 7
agcaacaatt ccactgtggc ttgcatt                                          27

<210> SEQ ID NO 8
<211> LENGTH: 24
<212> TYPE: DNA
<213> ORGANISM: Artificial sequence
<220> FEATURE:
<223> OTHER INFORMATION: Primer

<400> SEQUENCE: 8
```

```
cctcctgagt tctctgagtg caac                                          24

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
cacggcagct cccatttcta                                               20

<210> SEQ ID NO 10
<211> LENGTH: 32
<212> TYPE: DNA
<213> ORGANISM: Artificial sequence
<220> FEATURE:
<223> OTHER INFORMATION: Primer

<400> SEQUENCE: 10
actataactc catcaaaagg agtggctccc ag                                 32

<210> SEQ ID NO 11
<211> LENGTH: 20
<212> TYPE: DNA
<213> ORGANISM: Artificial sequence
<220> FEATURE:
<223> OTHER INFORMATION: Primer

<400> SEQUENCE: 11
agcccgggac ttcatcaatc                                               20

<210> SEQ ID NO 12
<211> LENGTH: 19
<212> TYPE: DNA
<213> ORGANISM: Artificial sequence
<220> FEATURE:
<223> OTHER INFORMATION: Primer

<400> SEQUENCE: 12
tgaagccgct gctcatgag                                                19

<210> SEQ ID NO 13
<211> LENGTH: 23
<212> TYPE: DNA
<213> ORGANISM: Artificial sequence
<220> FEATURE:
<223> OTHER INFORMATION: Primer

<400> SEQUENCE: 13
tctgtatgcc gcattccagg ccg                                           23

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
ggacgtcatt gtagccaacc taa                                           23

<210> SEQ ID NO 15
<211> LENGTH: 22
<212> TYPE: DNA
<213> ORGANISM: Artificial sequence
```

```
<220> FEATURE:
<223> OTHER INFORMATION: Primer

<400> SEQUENCE: 15
cctgtagggt ctccaccact ga                                              22

<210> SEQ ID NO 16
<211> LENGTH: 28
<212> TYPE: DNA
<213> ORGANISM: Artificial sequence
<220> FEATURE:
<223> OTHER INFORMATION: Primer

<400> SEQUENCE: 16
cccatcttca agaaggccac agtgacct                                        28

<210> SEQ ID NO 17
<211> LENGTH: 21
<212> TYPE: DNA
<213> ORGANISM: Artificial sequence
<220> FEATURE:
<223> OTHER INFORMATION: Primer

<400> SEQUENCE: 17
cggtccaggt gagaaagatt g                                               21

<210> SEQ ID NO 18
<211> LENGTH: 18
<212> TYPE: DNA
<213> ORGANISM: Artificial sequence
<220> FEATURE:
<223> OTHER INFORMATION: Primer

<400> SEQUENCE: 18
cgtcttggct cgctgctc                                                   18

<210> SEQ ID NO 19
<211> LENGTH: 25
<212> TYPE: DNA
<213> ORGANISM: Artificial sequence
<220> FEATURE:
<223> OTHER INFORMATION: Primer

<400> SEQUENCE: 19
acccgtggct ctcgtctcaa catca                                           25

<210> SEQ ID NO 20
<211> LENGTH: 19
<212> TYPE: DNA
<213> ORGANISM: Artificial sequence
<220> FEATURE:
<223> OTHER INFORMATION: Primer

<400> SEQUENCE: 20
gccggctcag tgagacaag                                                  19

<210> SEQ ID NO 21
<211> LENGTH: 21
<212> TYPE: DNA
<213> ORGANISM: Artificial sequence
<220> FEATURE:
<223> OTHER INFORMATION: Primer

<400> SEQUENCE: 21
tggcaccttt cagcaacaat g                                               21
```

```
<210> SEQ ID NO 22
<211> LENGTH: 27
<212> TYPE: DNA
<213> ORGANISM: Artificial sequence
<220> FEATURE:
<223> OTHER INFORMATION: Primer

<400> SEQUENCE: 22
acgaaagcca tggttgcttg ttaccca                                          27

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
gctgggcaac tacaggataa ac                                               22

<210> SEQ ID NO 24
<211> LENGTH: 19
<212> TYPE: DNA
<213> ORGANISM: Artificial sequence
<220> FEATURE:
<223> OTHER INFORMATION: Primer

<400> SEQUENCE: 24
catagcctgt tcgttgcct                                                   19

<210> SEQ ID NO 25
<211> LENGTH: 26
<212> TYPE: DNA
<213> ORGANISM: Artificial sequence
<220> FEATURE:
<223> OTHER INFORMATION: Primer

<400> SEQUENCE: 25
cacgactgcc aggctcctat tgtgtg                                           26

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
acagacccag ctggagatcg                                                  20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
tccagtgact gcagccactt                                                  20

<210> SEQ ID NO 28
<211> LENGTH: 25
<212> TYPE: DNA
<213> ORGANISM: Artificial sequence
<220> FEATURE:
<223> OTHER INFORMATION: Primer

<400> SEQUENCE: 28
```
tttgccgcag tgctcacctc taacg                                         25

<210> SEQ ID NO 29
<211> LENGTH: 24
<212> TYPE: DNA
<213> ORGANISM: Artificial sequence
<220> FEATURE:
<223> OTHER INFORMATION: Primer

<400> SEQUENCE: 29
gaagacatcc ttcggaagca cgaa                                          24

<210> SEQ ID NO 30
<211> LENGTH: 22
<212> TYPE: DNA
<213> ORGANISM: Artificial sequence
<220> FEATURE:
<223> OTHER INFORMATION: Primer

<400> SEQUENCE: 30
ttggagatcc gagagaaaat gg                                            22

<210> SEQ ID NO 31
<211> LENGTH: 33
<212> TYPE: DNA
<213> ORGANISM: Artificial sequence
<220> FEATURE:
<223> OTHER INFORMATION: Primer

<400> SEQUENCE: 31
tgcctcctaa gctaacaatc tcccagagca ata                                33

<210> SEQ ID NO 32
<211> LENGTH: 25
<212> TYPE: DNA
<213> ORGANISM: Artificial sequence
<220> FEATURE:
<223> OTHER INFORMATION: Primer

<400> SEQUENCE: 32
aaccaacagt gatgtctggt cctat                                         25

<210> SEQ ID NO 33
<211> LENGTH: 18
<212> TYPE: DNA
<213> ORGANISM: Artificial sequence
<220> FEATURE:
<223> OTHER INFORMATION: Primer

<400> SEQUENCE: 33
gcacgtcatg ccgcagta                                                 18

<210> SEQ ID NO 34
<211> LENGTH: 27
<212> TYPE: DNA
<213> ORGANISM: Artificial sequence
<220> FEATURE:
<223> OTHER INFORMATION: Primer

<400> SEQUENCE: 34
ccattcccca gggcaagttc tatgacc                                       27

<210> SEQ ID NO 35
<211> LENGTH: 21
<212> TYPE: DNA
<213> ORGANISM: Artificial sequence

```
<220> FEATURE:
<223> OTHER INFORMATION: Primer

<400> SEQUENCE: 35
agcctgttgg taccaaatgg a                                              21

<210> SEQ ID NO 36
<211> LENGTH: 26
<212> TYPE: DNA
<213> ORGANISM: Artificial sequence
<220> FEATURE:
<223> OTHER INFORMATION: Primer

<400> SEQUENCE: 36
tttcggcctt gttgatatgt agatac                                         26

<210> SEQ ID NO 37
<211> LENGTH: 22
<212> TYPE: DNA
<213> ORGANISM: Artificial sequence
<220> FEATURE:
<223> OTHER INFORMATION: Primer

<400> SEQUENCE: 37
tgctgtctag agcccagcgg ca                                             22

<210> SEQ ID NO 38
<211> LENGTH: 17
<212> TYPE: DNA
<213> ORGANISM: Artificial sequence
<220> FEATURE:
<223> OTHER INFORMATION: Primer

<400> SEQUENCE: 38
ccgctgcagt caccgaa                                                   17

<210> SEQ ID NO 39
<211> LENGTH: 20
<212> TYPE: DNA
<213> ORGANISM: Artificial sequence
<220> FEATURE:
<223> OTHER INFORMATION: Primer

<400> SEQUENCE: 39
gccagccaga ctttcatggt                                                20

<210> SEQ ID NO 40
<211> LENGTH: 20
<212> TYPE: DNA
<213> ORGANISM: Artificial sequence
<220> FEATURE:
<223> OTHER INFORMATION: Primer

<400> SEQUENCE: 40
cggcgagccc cacttgtcca                                                20

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
ggttcctgat gggcaaagg                                                 19
```

```
<210> SEQ ID NO 42
<211> LENGTH: 20
<212> TYPE: DNA
<213> ORGANISM: Artificial sequence
<220> FEATURE:
<223> OTHER INFORMATION: Primer

<400> SEQUENCE: 42
tcagtgggct cagccatagg                                               20

<210> SEQ ID NO 43
<211> LENGTH: 19
<212> TYPE: DNA
<213> ORGANISM: Artificial Sequence
<220> FEATURE:
<223> OTHER INFORMATION: HIF-1 RNAi (position 933)

<400> SEQUENCE: 43
cccattcctc atccgtcaa                                                19

<210> SEQ ID NO 44
<211> LENGTH: 19
<212> TYPE: DNA
<213> ORGANISM: Artificial Sequence
<220> FEATURE:
<223> OTHER INFORMATION: HIF-1 RNAi (position 1832)

<400> SEQUENCE: 44
gcctaacagt cccagtgaa                                                19

<210> SEQ ID NO 45
<211> LENGTH: 19
<212> TYPE: DNA
<213> ORGANISM: Artificial Sequence
<220> FEATURE:
<223> OTHER INFORMATION: HIF-2 RNAi (position 566)

<400> SEQUENCE: 45
gcuuccuucg gacacauaa                                                19

<210> SEQ ID NO 46
<211> LENGTH: 19
<212> TYPE: RNA
<213> ORGANISM: Artificial Sequence
<220> FEATURE:
<223> OTHER INFORMATION: HIF-2 RNAi (position 1121)

<400> SEQUENCE: 46
gccacagcau ggacaugaa                                                19

<210> SEQ ID NO 47
<211> LENGTH: 18
<212> TYPE: RNA
<213> ORGANISM: Artificial Sequence
<220> FEATURE:
<223> OTHER INFORMATION: control RNAi

<400> SEQUENCE: 47
gcccgaguac aguaacga                                                 18
```